US012558418B2

(12) United States Patent
Matsunaga et al.

(10) Patent No.: US 12,558,418 B2
(45) Date of Patent: Feb. 24, 2026

(54) EGG ALLERGY ANTIGEN

(71) Applicant: HOYU CO., LTD., Aichi (JP)

(72) Inventors: Kayoko Matsunaga, Aichi (JP); Akiko Yagami, Aichi (JP); Masashi Nakamura, Aichi (JP); Yuji Aoki, Aichi (JP); Erika Kondo, Aichi (JP)

(73) Assignee: HOYU CO., LTD., Aichi (JP)

( * ) Notice: Subject to any disclaimer, the term of this patent is extended or adjusted under 35 U.S.C. 154(b) by 0 days.

(21) Appl. No.: 18/364,884

(22) Filed: Aug. 3, 2023

(65) Prior Publication Data

US 2024/0000924 A1 Jan. 4, 2024

Related U.S. Application Data

(62) Division of application No. 16/305,470, filed as application No. PCT/JP2017/020654 on Jun. 2, 2017, now abandoned.

(30) Foreign Application Priority Data

Jun. 2, 2016 (JP) ................................. 2016-111308

(51) Int. Cl.
*G01N 33/53* (2006.01)
*A61K 39/35* (2006.01)
(Continued)

(52) U.S. Cl.
CPC .............. *A61K 39/35* (2013.01); *A61P 37/08* (2018.01); *C07K 14/465* (2013.01); *C07K 16/18* (2013.01);
(Continued)

(58) Field of Classification Search
None
See application file for complete search history.

(56) References Cited

U.S. PATENT DOCUMENTS 6,143,559 A 11/2000 Michael et al.
11,298,419 B2 4/2022 Matsunaga et al.
(Continued)

FOREIGN PATENT DOCUMENTS

EP 1440978 A1 7/2004
JP 2001-318092 A 11/2001
(Continued)

OTHER PUBLICATIONS

NCBI BLAST Search Result of SEQ ID No. 2 in NR database (Year: 2025).*
(Continued)

*Primary Examiner* — M Franco G Salvoza
(74) *Attorney, Agent, or Firm* — McCarter & English, LLP; Yu Lu

(57) ABSTRACT

The present invention provides a novel antigen for an egg allergy, a method for diagnosing an egg allergy and a kit for diagnosing an egg allergy, a pharmaceutical composition comprising the antigen, an egg, a processed product of an egg, or a bird which lays or has hatched from the egg in which the antigen is eliminated or reduced, a method for producing a processed product of an egg in which the antigen is eliminated or reduced, and a tester for determining the presence or absence of an egg antigen in an object of interest.

7 Claims, 3 Drawing Sheets

Specification includes a Sequence Listing.

2D-PAGE (egg yolk, chicken egg (raw egg))

(51) Int. Cl.

| | |
|---|---|
| *A61P 37/08* | (2006.01) |
| *C07K 14/465* | (2006.01) |
| *C07K 16/18* | (2006.01) |
| *G01N 33/68* | (2006.01) |

(52) U.S. Cl.
CPC ..... *G01N 33/6854* (2013.01); *G01N 33/6893* (2013.01); *G01N 2333/465* (2013.01); *G01N 2333/775* (2013.01); *G01N 2800/24* (2013.01)

(56) References Cited

U.S. PATENT DOCUMENTS

| | | | |
|---|---|---|---|
| 2004/0265234 A1* | 12/2004 | Morimatsu | G01N 33/5308 424/9.81 |
| 2006/0205823 A1 | 9/2006 | Bodmer et al. | |
| 2007/0231448 A1* | 10/2007 | Takahashi | A23L 15/00 426/614 |
| 2009/0029005 A1 | 1/2009 | Van Amerongen et al. | |
| 2010/0210033 A1 | 8/2010 | Scott | |
| 2018/0193449 A1 | 7/2018 | Matsunaga et al. | |
| 2018/0355020 A1 | 12/2018 | Anchel | |
| 2021/0322543 A1 | 10/2021 | Matsunaga et al. | |
| 2023/0190924 A1 | 6/2023 | Matsunaga et al. | |

FOREIGN PATENT DOCUMENTS

| | | |
|---|---|---|
| JP | 2002/256000 A | 9/2002 |
| JP | 2002-286716 A | 10/2002 |
| JP | 2006-115761 A | 5/2006 |
| JP | 2008-507270 A | 3/2008 |
| JP | 2011-033544 A | 2/2011 |
| JP | 2011-033546 A | 2/2011 |
| JP | 2011-033547 A | 2/2011 |
| JP | 2011-033548 A | 2/2011 |
| JP | 2014-525745 A | 10/2014 |
| JP | 5894695 B1 | 3/2016 |
| JP | 2016-141666 A | 8/2016 |
| WO | WO-2016/190376 A1 | 12/2016 |

OTHER PUBLICATIONS

Amo et al., Gal d 6 is the second allergen characterized from egg yolk. J Agric Food Chem. Jun. 23, 2010;58(12):7453-7.

De Silva et al., Molecular and immunological analysis of hen's egg yolk allergens with a focus on YGP42 (Gal d 6). Mol Immunol. Mar. 2016;71:152-60.

GeneSeq Accession No. BDK15102, Chicken derived vitellogenin-2/major vitellogenein protein. 2 pages, Jan. 12, 2017.

Hildebrandt et al., In vitro determination of the allergenic potential of technologically altered hen's egg. J Agric Food Chem. Mar. 12, 2008;56(5):1727-33.

Hughes, Life-history evolution at the molecular level: adaptive amino acid composition of avian vitellogenins. Proc Biol Sci. Aug. 7, 2015;282(1812):20151105, 7 pages.

Matsuo et al., Identification of the IgE-binding Epitope in v-5 Gliadin, a major allergen in wheat-dependent exercise-induced anaphylaxis. J Biol Chem. 2004;279(13):12135-40.

NCBI Accession No. XP_015146355, Predicted: vitellogenin-3 [Gallus gallus]. Jan. 4, 2016, 2 pages.

NCBI Blast: Protein Sequence. Retrieved online at: https://blast.ncbi.hlm.nih.gov/Blast.cgi. 46 pages, Jun. 18, 2022.

REFSEQ Accession No. NP_001385236, Vitellogenin-3 precursor [Gallus gallus]. 2 pages, Apr. 12, 2022.

Silva et al., The major and minor chicken vitellogenin genes are each adjacent to partially deleted pseudogene copies of the other. Mol Cell Biol. Aug. 1989;9(8):3557-62.

Tamiya, Biosensorchip and antibody engineering. Bio Industry. Jul. 12, 2003;20(7):60-7.

UniParc RefSeq XP_422371, UniParc—UPI0000448988. 3 pages, Jan. 6, 2007.

UniProtKB/TrEMBL, Accession No. Q197X2. Apolipoprotein B. 3 pages, Jun. 8, 2016.

Wang et al., A zebrafish vitellogenin gene (vg3) encodes a novel vitellogenin without a phosvitin domain and may represent a primitive vertebrate vitellogenin gene. Gene. Oct. 3, 2000;256(1-2):303-10.

WHO/IUIS Allergen Nomenclature Sub-Committee, Allergen Nomenclature. 3 pages, (2016).

International Search Report for Application No. PCT/JP2017/020654, dated Aug. 29, 2017, 5 pages.

International Search Report for Application No. PCT/JP2017/043877, dated Feb. 20, 2018, 2 pages.

Supplementary Partial European Search Report for Application No. 17806837.5, dated Oct. 10, 2019, 17 pages.

U.S. Appl. No. 16/305,470, filed Nov. 29, 2018, 2021-0322543.

U.S. Appl. No. 16/617,860, filed Nov. 27, 2019, 2023-0190924.

Prickett et al., Immunoregulatory T cell epitope peptides: the new frontier in allergy therapy. Clinical & Experimental Allergy. 2015;45:1015-1026.

* cited by examiner

2D-PAGE (egg yolk, chicken egg (raw egg))

Immunoblot (patient with egg allergy)

Patient 1

2D-PAGE (egg yolk, chicken egg (raw egg))

Patient 2

EGG ALLERGY ANTIGEN

CROSS-REFERENCE TO RELATED APPLICATIONS

This application is a divisional application of U.S. patent application Ser. No. 16/305,470, filed on Nov. 29, 2018, which is a U.S. national stage filing, under 35 U.S.C. § 371(c), of International Application No. PCT/JP2017/020654, filed on Jun. 2, 2017, which claims priority to Japanese Patent Application No. 2016-111308, filed on Jun. 2, 2016. The entire contents of each of the aforementioned In the process of production of conventional allergy testing agents, antigen reagents are commonly prepared simply by grinding a candidate allergenic food, food material or the like (Patent Literature 1). For this reason, the only case where conventional allergy tests have permitted detection of a positive allergic reaction is when the allergen component contained in a conventional antigen reagent is present in an amount exceeding a threshold that allows determination of a positive reaction for binding to an IgE antibody and the diagnostic efficiency has been too low to be considered to be sufficient.

The allergens set forth in Table 1 below are currently known as egg allergens (Non Patent Literature 1).

TABLE 1

| Species | Allergen | Biochemical name | MW(SDS-PAGE) | Food Allergen | Entry Date | Modified Date |
|---|---|---|---|---|---|---|
| Gallus | Gal d 1 | Ovomucoid | 28 | Yes | 2016 Apr. 04 | 2010 Apr. 29 |
| domesticus | Gal d 2 | Ovalbumin | 44 | Yes | 2016 Apr. 04 | 2010 Apr. 29 |
| (chicken) | Gal d 3 | Ovotransferrin | 78 | Yes | 2016 Apr. 04 | 2010 Apr. 29 |
| | Gal d 4 | Lysozyme C | 14 | Yes | 2016 Apr. 04 | 2010 Apr. 29 |
| | Gal d 5 | Serum albumin | 69 | Yes | 2016 Apr. 04 | 2015 Dec. 19 |
| | Gal d 6 | YGP42 | 35 kDa | Yes | 2016 Apr. 04 | 2011 Aug. 04 |
| | Gal d 7 | Myosin light chain 1f | 22 kDa | Yes | 2016 Apr. 04 | 2015 Aug. 17 |
| | Gal d 8 | alpha-parvalbumin | 11.8 kDa | Yes | 2016 Apr. 04 | 2016 Feb. 22 |
| | Gal d 9 | Enolase | 50 kDa | Yes | 2016 Apr. 04 | 2016 Feb. 22 |
| | Gal d 10 | Aldolase | | Yes | 2016 Apr. 04 | 2016 Feb. 22 | applications, including all drawings and sequence listings, are incorporated herein by reference.

REFERENCE TO SEQUENCE LISTING

The instant application contains a Sequence Listing XML file which has been submitted electronically in XML format and is hereby incorporated by reference in its entirety. Said Sequence Listing XML copy, created on Aug. 3, 2023, is named Seglisting_129249-00303.XML and is 259,858 bytes in size. The sequence listing is part of the specification and is incorporated by reference herein in its entirety.

TECHNICAL FIELD

The present invention relates to a novel antigen of an egg allergy. The present invention also relates to a kit, a composition, and a method for diagnosing an egg allergy. The present invention also relates to a pharmaceutical composition comprising the antigen and an egg or a processed product of an egg in which the antigen is eliminated or reduced, or a bird which lays or has hatched from the egg. The present invention also relates to a method for producing a processed product of an egg in which the antigen is eliminated or reduced. The present invention also relates to a tester for determining the presence or absence of an egg antigen in an object of interest.

BACKGROUND ART

In serum and tissues of allergic patients, IgE antibodies specific to particular antigens (hereinafter, also referred to as "allergens") are produced. Physiological consequences caused by interaction between such IgE antibodies and such particular antigens elicit allergic reactions. The term "antigen" refers in its broad sense to a food or a food material which causes an allergic symptom and in its narrow sense to a protein contained in a food or a food material to which a specific IgE antibody binds (also referred to as the following, an allergenic component).

Some allergen components are suggested to exist in foods and food materials which are allergen candidates, and test kits for such allergen components have been commercialized. However, while it is necessary to exhaustively identify allergen components in order to enhance the reliability of allergy tests, the patient detection rate by the measurement of such allergen components is far insufficient. Identification of novel allergens in eggs is very important not only for increasing the precision of diagnostic agent, but also for determining targets of low allergic foods, low allergenic food materials, and therapeutic agents.

On the separation and purification of proteins, a method for separating and purifying many different proteins from a small amount of sample has been used in recent years, which is more specifically a two-dimensional electrophoresis consisting of isoelectric focusing in the first dimension, followed by SDS-PAGE (Sodium Dodecyl Sulfate-Polyacrylamide Gel Electrophoresis) in the second dimension. The present applicant has conventionally developed some 2D electrophoresis methods with high separation ability (Patent Literature 2-5).

CITATION LIST

Patent Literature

PTL1: Japanese Patent Application Publication No. JP 2002-286716

PTL2: Japanese Patent Application Publication No. JP 2011-33544

PTL3: Japanese Patent Application Publication No. JP 2011-33546

PTL4: Japanese Patent Application Publication No. JP 2011-33547

PTL5: Japanese Patent Application Publication No. JP 2011-33548

Non Patent Literature

NPL1: Allergen Nomenclature, WHO/IUIS Allergen Nomenclature Sub-Committee, [search on May 31, 2016]

SUMMARY OF INVENTION

Technical Problem

The present invention provides novel antigens of an allergy to egg. The present invention also provides methods and kits for diagnosing allergy to egg. The present invention also provides a pharmaceutical composition comprising the antigen and an egg or a processed product of an egg in which the antigen is eliminated or reduced, or a bird which lays or has hatched from the egg. The present invention further provides testers for determining the presence or absence of an egg antigen in an object of interest.

Solution to Problem

In order to solve the aforementioned problems, the present inventors had made intensive studies to identify causative antigens of an allergy to egg. As a result, the inventors succeeded in identifying novel antigens to which an IgE antibody in the serum of an egg-allergic patient specifically binds. The present invention has been completed based on this finding.

Thus, in one embodiment, the present invention can be as defined below.

[1] A kit for diagnosing an allergy to an egg, the kit comprising, as an antigen, at least one of proteins defined below in any of the following (1) to (3):

(1) (1A) a protein comprising a C-terminal portion of Vitellogenin-3 or a variant thereof, which is defined below in any of (1A-a) to (1A-e) which is an antigen for the egg allergy:

(1A-a) a protein comprising an amino acid sequence with deletion, substitution, insertion or addition of one or several amino acids in SEQ ID NO: 2;

(1A-b) a protein comprising an amino acid sequence having at least 70% identity to the amino acid sequence of SEQ ID NO: 2;

(1A-c) a protein comprising an amino acid sequence encoded by a nucleotide sequence with deletion, substitution, insertion or addition of one or several nucleotides in SEQ ID NO: 1;

(1A-d) a protein comprising an amino acid sequence encoded by a nucleotide sequence having at least 70% identity to the nucleotide sequence of SEQ ID NO: 1; or (1A-e) a protein comprising an amino acid sequence encoded by a nucleic acid that hybridizes under stringent conditions with a nucleic acid having a nucleotide sequence complementary to the nucleotide sequence of SEQ ID NO: 1; or (1B) a protein comprising at least one amino acid sequence selected from the group consisting of SEQ ID NOs: 2-11;

(2) (2A) a protein comprising a C-terminal portion of Vitellogenin-3 or a variant thereof, which is defined below in any of (2A-a) to (2A-e) which is an antigen for the egg allergy:

(2A-a) a protein comprising an amino acid sequence with deletion, substitution, insertion or addition of one or several amino acids in SEQ ID NO: 13;

(2A-b) a protein comprising an amino acid sequence having at least 70% identity to the amino acid sequence of SEQ ID NO: 13;

(2A-c) a protein comprising an amino acid sequence encoded by a nucleotide sequence with deletion, substitution, insertion or addition of one or several nucleotides in SEQ ID NO: 12;

(2A-d) a protein comprising an amino acid sequence encoded by a nucleotide sequence having at least 70% identity to the nucleotide sequence of SEQ ID NO: 12; or (2A-e) a protein comprising an amino acid sequence encoded by a nucleic acid that hybridizes under stringent conditions with a nucleic acid having a nucleotide sequence complementary to the nucleotide sequence of SEQ ID NO: 12; or (2B) a protein comprising at least one amino acid sequence selected from the group consisting of SEQ ID NOs: 9-11, 13, 14, and 16;

(3) (3A) A protein comprising a middle portion of Vitellogenin-1 or a C-terminal portion of lipovitelin-1 or a variant thereof, which is defined below in any of (3A-a) to (3A-e) which is an antigen for the egg allergy:

(3A-a) a protein comprising an amino acid sequence with deletion, substitution, insertion or addition of one or several amino acids in SEQ ID NO: 18;

(3A-b) a protein comprising an amino acid sequence having at least 70% identity to the amino acid sequence of SEQ ID NO: 18;

(3A-c) a protein comprising an amino acid sequence encoded by a nucleotide sequence with deletion, substitution, insertion or addition of one or several nucleotides in SEQ ID NO: 17;

(3A-d) a protein comprising an amino acid sequence encoded by a nucleotide sequence having at least 70% identity to the nucleotide sequence of SEQ ID NO: 17; or (3A-e) a protein comprising an amino acid sequence encoded by a nucleic acid that hybridizes under stringent conditions with a nucleic acid having a nucleotide sequence complementary to the nucleotide sequence of SEQ ID NO: 17; or (3B) a protein comprising at least one amino acid sequence selected from the group consisting of SEQ ID NOs: 18-45.

[2] A composition for diagnosing an allergy to an egg, comprising, as an antigen, at least one of proteins as defined above in any of (1) to (3) of [1].

[3] A method for providing an indicator for diagnosing an allergy to an egg in a subject, the method comprising the steps of:

(i) contacting a sample obtained from the subject with an antigen, wherein the sample is a solution comprising an IgE antibody;

(ii) detecting binding between the IgE antibody present in the sample from the subject and the antigen; and (iii) when the binding between the IgE antibody in the subject and the antigen is detected, an indicator of the fact that the subject is allergic to an egg is provided;

wherein the antigen is at least one of proteins as defined above in any of (1) to (3) of [1].

[4] A pharmaceutical composition comprising at least one of proteins as defined above in any of (1) to (3) of [1].

[5] The pharmaceutical composition as set forth in [4], wherein the pharmaceutical composition is intended for the treatment of an allergy to an egg.

[6] An egg, a processed product of an egg, or a bird which lays or has hatched from the egg in which an antigen is eliminated or reduced, wherein the antigen is at least one of the proteins as defined in (1) to (3) of [1].

[7] A tester for determining the presence or absence of an egg antigen in an object of interest, comprising an antibody that binds to at least one of proteins as defined above in any of (1) to (3) of [1].

[8] A tester for determining the presence or absence of an antigen for an egg allergy in an object of interest, comprising a primer having a nucleotide sequence complementary to at least one of the nucleotide sequences set forth in SEQ ID NO: 1, 12, or 17.

[9] A kit for diagnosing an egg allergy, the kit comprising, as an antigen, at least one protein defined in any one of the following (4) to (10):

(4) (4A) a protein comprising Vitellogenin-3 or a variant thereof, which is defined below in any of (4A-a) to (4A-e) which is an antigen for the egg allergy:
   (4A-a) a protein comprising an amino acid sequence with deletion, substitution, insertion or addition of one or several amino acids in SEQ ID NO: 47;
   (4A-b) a protein comprising an amino acid sequence having at least 70% identity to the amino acid sequence of SEQ ID NO: 47;
   (4A-c) a protein comprising an amino acid sequence encoded by a nucleotide sequence with deletion, substitution, insertion or addition of one or several nucleotides in SEQ ID NO: 46;
   (4A-d) a protein comprising an amino acid sequence encoded by a nucleotide sequence having at least 70% identity to the nucleotide sequence of SEQ ID NO: 46; or
   (4A-e) a protein comprising an amino acid sequence encoded by a nucleic acid that hybridizes under stringent conditions with a nucleic acid having a nucleotide sequence complementary to the nucleotide sequence of SEQ ID NO: 46; or
   (4B) a protein comprising at least one amino acid sequence selected from the group consisting of SEQ ID NOs: 47-57;

(5) (5A) a protein comprising a Vitellogenin-2 precursor or a variant thereof, which is defined below in any of (5A-a) to (5A-e) which is an antigen for the egg allergy:
   (5A-a) a protein comprising an amino acid sequence with deletion, substitution, insertion or addition of one or several amino acids in SEQ ID NO: 59;
   (5A-b) a protein comprising an amino acid sequence having at least 70% identity to the amino acid sequence of SEQ ID NO: 59;
   (5A-c) a protein comprising an amino acid sequence encoded by a nucleotide sequence with deletion, substitution, insertion or addition of one or several nucleotides in SEQ ID NO: 58;
   (5A-d) a protein comprising an amino acid sequence encoded by a nucleotide sequence having at least 70% identity to the nucleotide sequence of SEQ ID NO: 58; or
   (5A-e) a protein comprising an amino acid sequence encoded by a nucleic acid that hybridizes under stringent conditions with a nucleic acid having a nucleotide sequence complementary to the nucleotide sequence of SEQ ID NO: 58; or
   (5B) a protein comprising at least one amino acid sequence selected from the group consisting of SEQ ID NOs: 59-104;

(6) (6A) a Vitellogenin-2 precursor or a variant thereof, which is defined below in any of (6A-a) to (6A-e) which is an antigen for the egg allergy:

6

(6A-a) a protein comprising an amino acid sequence with deletion, substitution, insertion or addition of one or several amino acids in SEQ ID NO: 106;
   (6A-b) a protein comprising an amino acid sequence having at least 70% identity to the amino acid sequence of SEQ ID NO: 106;
   (6A-c) a protein comprising an amino acid sequence encoded by a nucleotide sequence with deletion, substitution, insertion or addition of one or several nucleotides in SEQ ID NO: 105;
   (6A-d) a protein comprising an amino acid sequence encoded by a nucleotide sequence having at least 70% identity to the nucleotide sequence of SEQ ID NO: 105; or
   (6A-e) a protein comprising an amino acid sequence encoded by a nucleic acid that hybridizes under stringent conditions with a nucleic acid having a nucleotide sequence complementary to the nucleotide sequence of SEQ ID NO: 105; or
   (6B) a protein comprising at least one amino acid sequence selected from the group consisting of SEQ ID NOs: 106-150;

(7) (7A) an Apolipoprotein B precursor or a variant thereof, which is defined below in any of (7A-a) to (7A-e) which is an antigen for the egg allergy:
   (7A-a) a protein comprising an amino acid sequence with deletion, substitution, insertion or addition of one or several amino acids in SEQ ID NO: 152;
   (7A-b) a protein comprising an amino acid sequence having at least 70% identity to the amino acid sequence of SEQ ID NO: 152;
   (7A-c) a protein comprising an amino acid sequence encoded by a nucleotide sequence with deletion, substitution, insertion or addition of one or several nucleotides in SEQ ID NO: 151;
   (7A-d) a protein comprising an amino acid sequence encoded by a nucleotide sequence having at least 70% identity to the nucleotide sequence of SEQ ID NO: 151; or
   (7A-e) a protein comprising an amino acid sequence encoded by a nucleic acid that hybridizes under stringent conditions with a nucleic acid having a nucleotide sequence complementary to the nucleotide sequence of SEQ ID NO: 151; or
   (7B) a protein comprising at least one amino acid sequence selected from the group consisting of SEQ ID NOs: 152-235;

(8) (8A) an Apolipoprotein B precursor or a variant thereof, which is defined below in any of (8A-a) to (8A-e) which is an antigen for the egg allergy:
   (8A-a) a protein comprising an amino acid sequence with deletion, substitution, insertion or addition of one or several amino acids in SEQ ID NO: 237;
   (8A-b) a protein comprising an amino acid sequence having at least 70% identity to the amino acid sequence of SEQ ID NO: 237;
   (8A-c) a protein comprising an amino acid sequence encoded by a nucleotide sequence with deletion, substitution, insertion or addition of one or several nucleotides in SEQ ID NO: 236;
   (8A-d) a protein comprising an amino acid sequence encoded by a nucleotide sequence having at least 70% identity to the nucleotide sequence of SEQ ID NO: 236; or
   (8A-e) a protein comprising an amino acid sequence encoded by a nucleic acid that hybridizes under stringent conditions with a nucleic acid having a nucleotide sequence complementary to the nucleotide sequence of SEQ ID NO: 236; or (8B) a protein comprising at least one amino acid sequence selected from the group consisting of SEQ ID NOs: 237-249;

(9) (9A) an Apolipoprotein B precursor or a variant thereof, which is defined below in any of (9A-a) to (9A-e) which is an antigen for the egg allergy:

(9A-a) a protein comprising an amino acid sequence with deletion, substitution, insertion or addition of one or several amino acids in SEQ ID NO: 251;

(9A-b) a protein comprising an amino acid sequence having at least 70% identity to the amino acid sequence of SEQ ID NO: 251;

(9A-c) a protein comprising an amino acid sequence encoded by a nucleotide sequence with deletion, substitution, insertion or addition of one or several nucleotides in SEQ ID NO: 250;

(9A-d) a protein comprising an amino acid sequence encoded by a nucleotide sequence having at least 70% identity to the nucleotide sequence of SEQ ID NO: 250; or (9A-e) a protein comprising an amino acid sequence encoded by a nucleic acid that hybridizes under stringent conditions with a nucleic acid having a nucleotide sequence complementary to the nucleotide sequence of SEQ ID NO: 250; or (9B) a protein comprising at least one amino acid sequence selected from the group consisting of SEQ ID NOs: 251-260;

(10) (10A) a Vitellogenin-2 precursor or a variant thereof, which is defined below in any of (10A-a) to (10A-e) which is an antigen for the egg allergy:

(10A-a) a protein comprising an amino acid sequence with deletion, substitution, insertion or addition of one or several amino acids in SEQ ID NO: 262;

(10A-b) a protein comprising an amino acid sequence having at least 70% identity to the amino acid sequence of SEQ ID NO: 262;

(10A-c) a protein comprising an amino acid sequence encoded by a nucleotide sequence with deletion, substitution, insertion or addition of one or several nucleotides in SEQ ID NO: 261;

(10A-d) a protein comprising an amino acid sequence encoded by a nucleotide sequence having at least 70% identity to the nucleotide sequence of SEQ ID NO: 261; or (10A-e) a protein comprising an amino acid sequence encoded by a nucleic acid that hybridizes under stringent conditions with a nucleic acid having a nucleotide sequence complementary to the nucleotide sequence of SEQ ID NO: 261; or (10B) a protein comprising at least one amino acid sequence selected from the group consisting of SEQ ID NOs: 262-271.

[10] A composition for diagnosing an allergy to an egg, comprising, as an antigen, at least one of proteins as defined above in any of (4) to (10) of [9].

[11] A method for providing an indicator for diagnosing an allergy to an egg in a subject, the method comprising the steps of:

(i) contacting a sample obtained from the subject with an antigen, wherein the sample is a solution comprising an IgE antibody;

(ii) detecting binding between the IgE antibody present in the sample from the subject and the antigen; and (iii) when the binding between the IgE antibody in the subject and the antigen is detected, an indicator of the fact that the subject is allergic to an egg is provided;

wherein the antigen is at least one of proteins as defined above in any of (4) to (10) of [9].

[12] A pharmaceutical composition comprising at least one of proteins as defined above in any of (4) to (10) of [9].

[13] The pharmaceutical composition as set forth in [12], wherein the pharmaceutical composition is intended for the treatment of an allergy to an egg.

[14] An egg, a processed product of an egg, or a bird which lays or has hatched from the egg in which an antigen is eliminated or reduced, wherein the antigen is at least one of the proteins as defined in (4) to (10) of [9].

[15] A tester for determining the presence or absence of an egg antigen in an object of interest, comprising an antibody that binds to at least one of proteins as defined above in any of (4) to (10) of [9].

[16] A tester for determining the presence or absence of an antigen for an egg allergy in an object of interest, comprising a primer having a nucleotide sequence complementary to at least one of the nucleotide sequences set forth in SEQ ID NO: 46, 58, 105, 151, 236, 250, or 261.

[17] A method for producing a processed product of an egg in which an antigen is eliminated or reduced, comprising the step of confirming that the antigen is eliminated or reduced in the process of producing the processed product, wherein the antigen is at least one of the proteins as defined in any of (1) to (3) of [1] or at least one of the proteins as defined in any of (4) to (10) of [9].

[18] An antigen derived from an egg, wherein the antigen is at least one of the proteins as defined in any of (1) to (3) of [1] or at least one of the proteins as defined in any of (4) to (10) of [9] and causative of an egg allergy.

Advantageous Effects of Invention

The present invention can provide novel antigens of an allergy to egg. Since the novel antigens (allergen components) that trigger an egg allergy were identified in the present invention, it is possible to provide highly sensitive methods and kits for diagnosing an egg allergy, pharmaceutical compositions comprising such an antigen, eggs or processed products of eggs in which such an antigen is eliminated or reduced, or birds that lay or have hatched from the eggs, methods for producing a processed product of an egg in which the antigen is eliminated or reduced, and testers for determining the presence or absence of an egg antigen in an object of interest.

US 12,558,418 B2

9 specifically reacted with the serum of Egg-allergic patient 1 are indicated with respective surrounding boxes.

Figure 4:
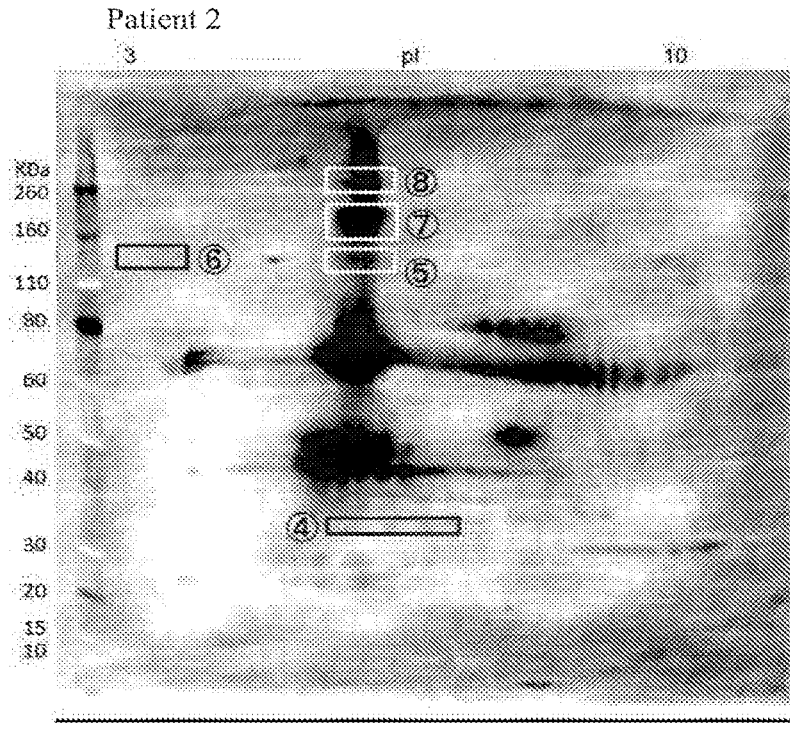

FIG. 4 is a photograph of an immunoblot of a two-dimensional electrophoretic pattern of proteins contained in egg yolk of a chicken egg (raw egg) stained using serum of Egg-allergic patient 2. Spots 4 to 8 that have specifically reacted with the serum of Egg-allergic patient 2 are indicated with respective surrounding boxes.

Figure 5:
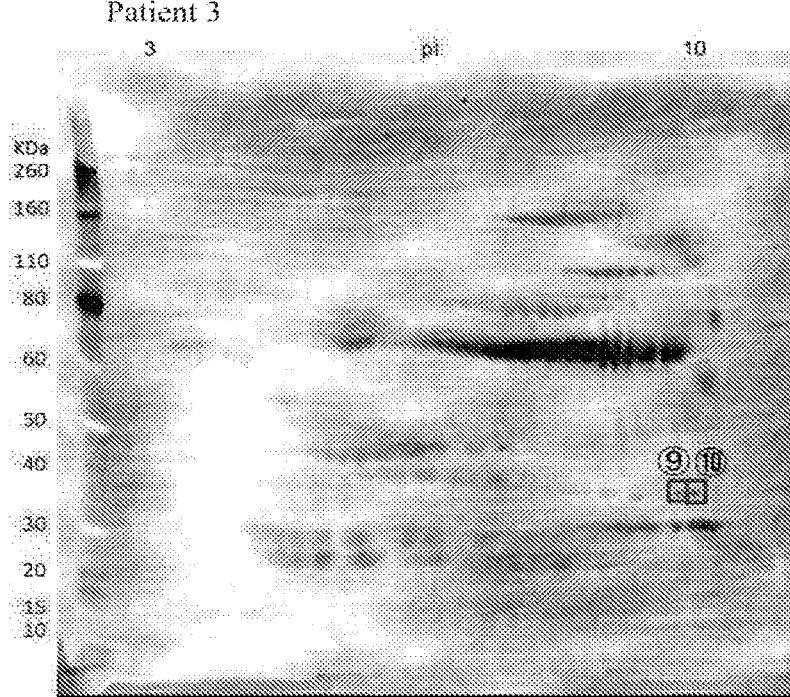

FIG. 5 is a photograph of an immunoblot of a two-dimensional electrophoretic pattern of proteins contained in egg yolk of a chicken egg (raw egg) stained using serum of Egg-allergic patient 3. Spots 9 and 10 that have specifically reacted with the serum of Egg-allergic patient 3 are indicated with respective surrounding boxes.

Figure 6:
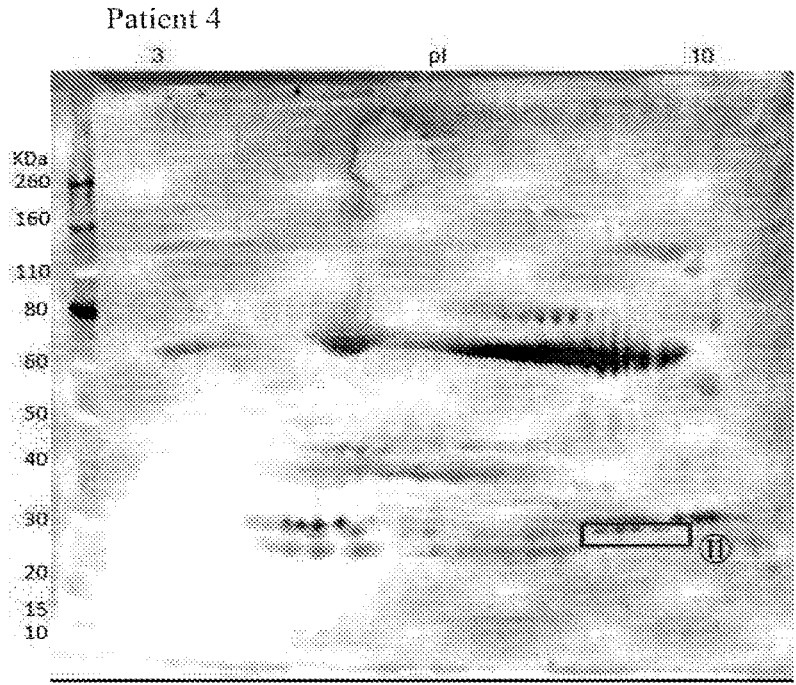

FIG. 6 is a photograph of an immunoblot of a two-dimensional electrophoretic pattern of proteins contained in egg yolk of a chicken egg (raw egg) stained using serum of Egg-allergic patient 4. Spot 11 that has specifically reacted with the serum of Egg-allergic patient 4 is indicated with a surrounding box.

DESCRIPTION OF EMBODIMENTS

The present invention will be described in detail below, but the present invention is not limited to them.

Unless otherwise defined herein, all scientific and technical terms used in relation to the present invention shall have meanings commonly understood by those skilled in the art.

As referred to herein, the "allergy" refers to the state in which, when a certain antigen enters the body of a living individual sensitized to said antigen, the living individual shows a hypersensitive reaction detrimental to him/her. In blood and tissues of individuals with many food-allergic diseases, IgE antibodies specific to antigens are produced. IgE antibodies bind to mast cells or basophils. When an antigen specific to such an IgE antibody enters again the body of a patient with an allergic disease, said antigen combines with the IgE antibody bound to mast cells or basophils, and the IgE antibody crosslinks said antigen on the cell surface, resulting in physiological effects of IgE antibody-antigen interaction. Examples of such physiological effects include release of histamine, serotonin, heparin, eosinophil chemotactic factors, leucotrienes, or the like. These released substances provoke an allergic reaction resulting from the combination of an IgE antibody with particular antigens. Such allergic reactions caused by particular antigens occur through the aforementioned pathway.

As referred herein, the "egg" refers to an egg of a bird, preferably a chicken egg.

As referred to herein, the "allergy to egg" refers to the state in which an individual has an allergic reaction caused by proteins, etc. present in egg which act as an antigen. The allergy to egg can produce an allergic reaction upon contact with, or consumption of, an antigen present in egg. In general, allergic reactions caused by consumption of foods are particularly referred to as "food allergies". The allergy to egg may be a food allergy.

As referred to herein, the "antigen" refers to a substance that provokes an allergic reaction, and is also referred to as an "allergen component". The antigen is preferably a protein.

As referred to herein, the "protein" refers to a molecule having a structure in which naturally occurring amino acids are joined together by peptide bond. The number of amino acids present in a protein is not particularly limited, but proteins having about 2 to 50 amino acids joined together by peptide bond are in some cases called "peptides". In the case where amino acids can form different enantiomers, the amino acids are understood to form an L-enantiomer, unless otherwise indicated. The amino acid sequences of proteins or peptides as used herein are represented by one-letter symbols of amino acids in accordance with standard usage and the notational convention commonly used in the art. The leftward direction represents the amino-terminal direction, and the rightward direction represents the carboxy-terminal direction.

Identification of Antigens

Proteins contained in egg were analyzed by the aforementioned technique to identify causative antigens of an allergy to egg. To be specific, raw chicken eggs were separated into egg yolk and egg white and the egg proteins contained in each of them were subjected to two-dimensional electrophoresis under the conditions described below.

The electrophoresis in the first dimension was isoelectric focusing, which was performed using isoelectric focusing gels with a gel-strip length of 5 to 10 cm and a gel pH range of 3 to 10. The pH gradient of the gels in the direction of electrophoresis was as follows: with the total gel-strip length being taken as 1, the gel-strip length up to pH 5 was "a=0.15 to 0.3", the gel-strip length from pH 5 to 7 was "b=0.4 to 0.7", and the gel-strip length above pH 7 was "c=0.15 to 0.3". More specifically, the isoelectric focusing was performed using the IPG gels, Immobiline Drystrip (pH3-10NL), produced by GE Healthcare Bio-Sciences Corporation (hereinafter abbreviated as "GE"). The electrophoresis system used was IPGphor produced by GE. The maximum current of the electrophoresis system was limited to 75 μA per gel strip. The voltage program adopted to perform the first-dimensional isoelectric focusing was as follows: (1) a constant voltage step was performed at a constant voltage of 300 V until the volt-hours reached 750 Vhr (the current variation width during electrophoresis for 30 minutes before the end of this step was 5 μA); (2) the voltage was increased gradually to 1000 V for 300 Vhr; (3) the voltage was further increased gradually to 5000 V for 4500 Vhr; and then (4) the voltage was held at a constant voltage of 5000 V until the total Vhr reached 12000.

The electrophoresis in the second dimension was SDS-PAGE, which was performed using polyacrylamide gels whose gel concentration at the distal end in the direction of electrophoresis was set to 3 to 6% and whose gel concentration at the proximal end was set to a higher value than that at the distal end. More specifically, the SDS-PAGE was performed using NuPAGE 4-12% Bris-Tris Gels (IPG well, Mini, 1 mm) produced by Life Technologies. The electrophoresis system used was XCell SureLock Mini-Cell produced by Life Technologies. The electrophoresis was run at a constant voltage of 200 V for about 45 minutes using an electrophoresis buffer composed of 50 mM MOPS, 50 mM Tris base, 0.1% (w/v) SDS and 1 mM EDTA.

Figure 3:
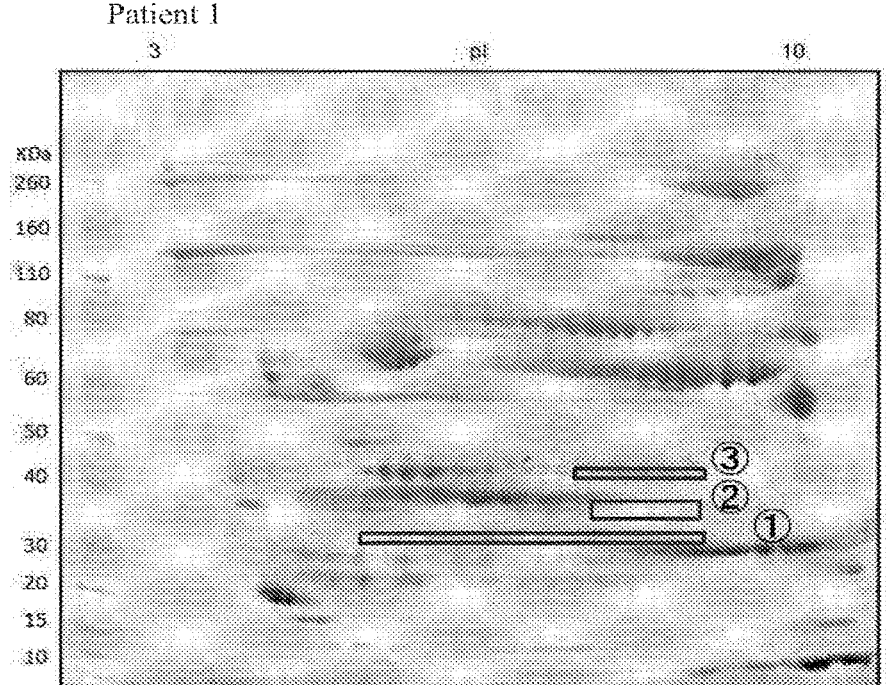
FIG. 3 is a photograph of a gel of a two-dimensional electrophoretic pattern of proteins contained in egg yolk of a chicken egg (raw egg). Spots 1, 2, and 3 that have

As a result, the antigens of Spots 1 to 3 in the gel in which the chicken egg proteins have been separated by two-dimensional electrophoresis under the conditions described above have been revealed to exhibit specific binding to IgE antibodies from an egg-allergic patient diagnosed to be have food-dependent exercise-induced anaphylaxis (FIG. 3). Moreover, the antigens of Spots 4 to 11 have been revealed to exhibit specific binding to IgE antibodies from other egg-allergic patients (FIGS. 4 to 6).

Antigen (1) Antigen in Spot 1

As the result of sequence identification of the antigen in spot 1 by mass spectroscopy, the amino acid sequences of SEQ ID NOs: 3-11 were detected.

Also, the mass spectroscopic data obtained for spot 1 (SEQ ID NOs: 3-11) on a mass spectrometer was analyzed by comparing the data against the NCBI protein data, and as a result, a C-terminal portion of Vitellogenin-3 (amino acid sequence: SEQ ID NO: 2, encoding nucleotide sequence: SEQ ID NO: 1) was identified.

Accordingly, in the present invention, the antigen in spot 1 can be any of (1A-a) to (1A-e) and (1B) as defined below:

(1A-a) a protein comprising an amino acid sequence with deletion, substitution, insertion or addition of one or several amino acids in SEQ ID NO: 2;

(1A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 2;

(1A-c) a protein comprising an amino acid sequence encoded by a nucleotide sequence with deletion, substitution, insertion or addition of one or several nucleotides in SEQ ID NO: 1;

(1A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 1;

(1A-e) a protein comprising an amino acid sequence encoded by a nucleic acid that hybridizes under stringent conditions with a nucleic acid having a nucleotide sequence complementary to the nucleotide sequence of SEQ ID NO: 1;

(1B) a protein comprising at least one amino acid sequence selected from the group consisting of SEQ ID NOs: 2-11, preferably a protein comprising at least 2, 3, 4, 5, 6, 7, 8, 9 or all sequences of the amino acid sequences; more preferably a protein comprising at least one amino acid sequence selected from the group consisting of SEQ ID NOs: 2, 4 and 9-11, preferably a protein comprising at least 2, 3, 4 or all sequences of the amino acid sequences. As referred to above, the amino acid sequence of any of SEQ ID NOs: 3-11 may be an amino acid sequence derived therefrom by deletion, substitution, insertion or addition of one or several amino acids.

The proteins of (1A-a) to (1A-e) and (1B) as defined above can be proteins that are found in a protein spot with a molecular weight of around 20 to 40 kDa, preferably around 30 to 35 kDa and an isoelectric point of 4.0 to 10.0, preferably an isoelectric point of 4.0 to 9.0 on gels used in the two-dimensional electrophoresis performed under the conditions described above in the subsection titled "Identification of antigens".

(2) Antigen in Spot 2

As the result of sequence identification of the antigen in spot 2 by mass spectroscopy, the amino acid sequences of SEQ ID NOs: 9-11, 14, 16 were detected.

Also, the mass spectroscopic data obtained for spot 2 (SEQ ID NOs: 9-11, 14, 16) on a mass spectrometer was analyzed by comparing the data against the NCBI protein data, and as a result, a C-terminal portion of Vitellogenin-3 (amino acid sequence: SEQ ID NO: 13, encoding nucleotide sequence: SEQ ID NO: 12) was identified.

Accordingly, in the present invention, the antigen in spot 2 can be any of (2A-a) to (2A-e) and (2B) as defined below:

(2A-a) a protein comprising an amino acid sequence with deletion, substitution, insertion or addition of one or several amino acids in SEQ ID NO: 13;

(2A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 13;

(2A-c) a protein comprising an amino acid sequence encoded by a nucleotide sequence with deletion, substitution, insertion or addition of one or several nucleotides in SEQ ID NO: 12;

(2A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 12;

(2A-e) a protein comprising an amino acid sequence encoded by a nucleic acid that hybridizes under stringent conditions with a nucleic acid having a nucleotide sequence complementary to the nucleotide sequence of SEQ ID NO: 12;

(2B) a protein comprising at least one amino acid sequence selected from the group consisting of SEQ ID NOs: 9-11, 13, 14 and 16, preferably a protein comprising at least 2, 3, 4, 5 or all sequences of the amino acid sequences. More preferably, a protein comprising at least one amino acid sequence selected from the group consisting of SEQ ID NOs: 9-11, 13, and 16, preferably a protein comprising at least 2, 3, 4, or all sequences of the amino acid sequences. As referred to above, the amino acid sequence of any of SEQ ID NOs: 9-11, 13, 14, 16 may be an amino acid sequence derived therefrom by deletion, substitution, insertion or addition of one or several amino acids.

The proteins of (2A-a) to (2A-e) and (2B) as defined above can be proteins that are found in a protein spot with a molecular weight of around 30 to 60 kDa, preferably around 35 to 40 kDa and an isoelectric point of 5.0 to 10.0, preferably 6.0 to 9.0 on gels used in the two-dimensional electrophoresis performed under the conditions described above in the subsection titled "Identification of antigens".

(3) Antigen in Spot 3

As the result of sequence identification of the antigen in spot 3 by mass spectroscopy, the amino acid sequences of SEQ ID NOs: 19-45 were detected.

Also, the mass spectroscopic data obtained for spot 3 (SEQ ID NOs: 19-45) on a mass spectrometer was analyzed by comparing the data against the UniProt protein data, and as a result, a middle portion of Vitellogenin-1 or a C-terminal portion of Lipovitelin-1 (amino acid sequence: SEQ ID NO: 18, encoding nucleotide sequence: SEQ ID NO: 17) generated by N-terminal truncation of the protein was identified.

Accordingly, in the present invention, the antigen in spot 3 can be any of (3A-a) to (3A-e) and (3B) as defined below:

(3A-a) a protein comprising an amino acid sequence with deletion, substitution, insertion or addition of one or several amino acids in SEQ ID NO: 18;

(3A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 18;

(3A-c) a protein comprising an amino acid sequence encoded by a nucleotide sequence with deletion, substitution, insertion or addition of one or several nucleotides in SEQ ID NO: 17;

(3A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 17.

(3A-e) a protein comprising an amino acid sequence encoded by a nucleic acid that hybridizes under stringent conditions with a nucleic acid having a nucleotide sequence complementary to the nucleotide sequence of SEQ ID NO: 17;

(3B) A protein comprising at least one amino acid sequence selected from the group consisting of SEQ ID NOs: 18-45, preferably a protein comprising at least 2, 3, 4, 5, 6, 7, 8, 9, 10, 11, 12, 13, 14, 15, 16, 17, 18, 19, 20, 21, 22, 23, 24, 25, 26, 27, or all sequences of the amino acid sequences. More preferably, a protein comprising at least one amino acid sequence selected from the group consisting of SEQ ID NOs: 18, 19, 22-31, 33-35, 37, 39, 40, 42, 43, and 45, preferably, a protein comprising at least 2, 3, 4, 5, 6, 7, 8, 9, 10, 11, 12, 13, 14, 15, 16, 17, 18, 19, 20, or all sequences of the amino acid sequences. As referred to above, the amino acid sequence of any of SEQ ID NOs:18-45 may be an amino acid sequence derived therefrom by deletion, substitution, insertion or addition of one or several amino acids.

The proteins of (3A-a) to (3A-e) and (3B) as defined above can be proteins that are found in a protein spot with a molecular weight of around 35 to 60 kDa, preferably around 40 to 50 kDa and an isoelectric point of 5.0 to 10.0, preferably 6.0 to 9.0 on gels used in the two-dimensional electrophoresis performed under the conditions described above in the subsection titled "Identification of antigens".

(4) Antigen in Spot 4

As the result of sequence identification of the antigen in spot 4 by mass spectroscopy, the amino acid sequences of SEQ ID NOs: 48-57 were detected.

Also, the mass spectroscopic data (SEQ ID NOs: 48-57) obtained for spot 4 on a mass spectrometer was analyzed by comparing the data against the NCBI protein data, and as a result, the antigen in question was identified as Vitellogenin-3 (amino acid sequence: SEQ ID NO: 47, encoding nucleotide sequence: SEQ ID NO: 46).

Accordingly, in the present invention, the antigen in spot 4 can be any of (4A-a) to (4A-e) and (4B) as defined below:

(4A-a) a protein comprising an amino acid sequence with deletion, substitution, insertion or addition of one or several amino acids in SEQ ID NO: 47;

(4A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 47;

(4A-c) a protein comprising an amino acid sequence encoded by a nucleotide sequence with deletion, substitution, insertion or addition of one or several nucleotides in SEQ ID NO: 46;

(4A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 46;

(4A-e) a protein comprising an amino acid sequence encoded by a nucleic acid that hybridizes under stringent conditions with a nucleic acid having a nucleotide sequence complementary to the nucleotide sequence of SEQ ID NO: 46;

(4B) a protein comprising at least one amino acid sequence selected from the group consisting of SEQ ID NOs: 47-57, preferably a protein comprising at least 2, 3, 4, 5, 6, 7, 8, 9, 10, or all sequences of the amino acid sequences. More preferably, a protein comprising at least one amino acid sequence selected from the group consisting of SEQ ID NOs: 47, 50, 51, 53, and 54, preferably a protein comprising at least 2, 3, 4, or all sequences of the amino acid sequences. As referred to above, the amino acid sequence of any of SEQ ID NOs:47-57 may be an amino acid sequence derived therefrom by deletion, substitution, insertion or addition of one or several amino acids.

The proteins of (4A-a) to (4A-e) and (4B) as defined above can be proteins that are found in a protein spot with a molecular weight of around 20 to 50 kDa, preferably around 25 to 40 kDa, more preferably around 30 to 35 kDa and an isoelectric point of 3.0 to 8.0, preferably 3.5 to 7.0, more preferably 4.0 to 6.0 on gels used in the two-dimensional electrophoresis performed under the conditions described above in the subsection titled "Identification of antigens".

(5) Antigen in Spots 5 and 6

As the result of sequence identification of the antigen in spots 5 and 6 by mass spectroscopy, the amino acid sequences of SEQ ID NOs: 60-104 were detected.

Also, the mass spectroscopic data (SEQ ID NOs: 60-104) obtained for spots 5 and 6 on a mass spectrometer was analyzed by comparing the data against the NCBI protein data, and as a result, the antigen in question was identified as Vitellogenin-2 precursor (amino acid sequence: SEQ ID NO: 59, encoding nucleotide sequence: SEQ ID NO: 58).

Accordingly, in the present invention, the antigen in spots 5 and 6 can be any of (5A-a) to (5A-e) and (5B) as defined below:

(5A-a) a protein comprising an amino acid sequence with deletion, substitution, insertion or addition of one or several amino acids in SEQ ID NO: 59;

(5A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 59;

(5A-c) a protein comprising an amino acid sequence encoded by a nucleotide sequence with deletion, substitution, insertion or addition of one or several nucleotides in SEQ ID NO: 58;

(5A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 58;

(5A-e) a protein comprising an amino acid sequence encoded by a nucleic acid that hybridizes under stringent conditions with a nucleic acid having a nucleotide sequence complementary to the nucleotide sequence of SEQ ID NO: 58;

(5B) a protein comprising at least one amino acid sequence selected from the group consisting of SEQ ID NOs: 59-104, preferably a protein comprising at least 2, 3, 4, 5, 6, 7, 8, 9, 10, 15, 20, 25, 30, 35, 40, 45, or all sequences of the amino acid sequences. More preferably, a protein comprising at least one amino acid sequence selected from the group consisting of SEQ ID NOs: 59, 60, 63, 65, 68, 69, 71, 73, 75-79, 81, 83-88, 91-94, 96-99, and 101-103, preferably, a protein comprising at least 2, 3, 4, 5, 6, 7, 8, 9, 10, 15, 20, 25, 30, or all sequences of the amino acid sequences. As referred to above, the amino acid sequence of any of SEQ ID NOs:59 to 104 may be an amino acid sequence derived therefrom by deletion, substitution, insertion or addition of one or several amino acids.

The proteins of (5A-a) to (5A-e) and (5B) as defined above can be proteins that are found in a protein spot with a molecular weight of around 80 to 260 kDa, preferably around 90 to 200 kDa, more preferably around 110 to 160 kDa and an isoelectric point of 1.0 to 8.0, preferably 2.0 to 7.0, more preferably 3.0 to 6.0 on gels used in the two-dimensional electrophoresis performed under the conditions described above in the subsection titled "Identification of antigens".

(6) Antigen in Spot 7

As the result of sequence identification of the antigen in spot 7 by mass spectroscopy, the amino acid sequences of SEQ ID NOs: 107-150 were detected.

Also, the mass spectroscopic data (SEQ ID NOs: 107-150) obtained for spot 7 on a mass spectrometer was analyzed by comparing the data against the NCBI protein data, and as a result, the antigen in question was identified as Vitellogenin-2 precursor (amino acid sequence: SEQ ID NO: 106, encoding nucleotide sequence: SEQ ID NO: 105).

Accordingly, in the present invention, the antigen in spot 7 can be any of (6A-a) to (6A-e) and (6B) as defined below:

(6A-a) a protein comprising an amino acid sequence with deletion, substitution, insertion or addition of one or several amino acids in SEQ ID NO: 106;

(6A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 106;

(6A-c) a protein comprising an amino acid sequence encoded by a nucleotide sequence with deletion, substitution, insertion or addition of one or several nucleotides in SEQ ID NO: 105;

(6A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 105;

(6A-e) a protein comprising an amino acid sequence encoded by a nucleic acid that hybridizes under stringent conditions with a nucleic acid having a nucleotide sequence complementary to the nucleotide sequence of SEQ ID NO: 105;

(6B) a protein comprising at least one amino acid sequence selected from the group consisting of SEQ ID NOs: 106-150, preferably a protein comprising at least 2, 3, 4, 5, 6, 7, 8, 9, 10, 15, 20, 25, 30, 35, 40, 44 or all sequences of the amino acid sequences. More preferably, a protein comprising at least one amino acid sequence selected from the group consisting of SEQ ID NOs: 106, 108, 110, 111, 113, 114, 116, 117, 120-124, 126-131, 133, 134, 136-138, 140-143, 145-147, and 149, preferably, a protein comprising at least 2, 3, 4, 5, 6, 7, 8, 9, 10, 15, 20, 25, 30, 31, or all sequences of the amino acid sequences. As referred to above, the amino acid sequence of any of SEQ ID NOs: 106-150 may be an amino acid sequence derived therefrom by deletion, substitution, insertion or addition of one or several amino acids.

The proteins of (6A-a) to (6A-e) and (6B) as defined above can be proteins that are found in a protein spot with a molecular weight of around 110 to 300 kDa, preferably around 130 to 280 kDa, more preferably around 160 to 260 kDa and an isoelectric point of 3.0 to 8.0, preferably 3.5 to 7.0, more preferably 4.0 to 6.0 on gels used in the two-dimensional electrophoresis performed under the conditions described above in the subsection titled "Identification of antigens".

(7) Antigen in Spot 8

As the result of sequence identification of the antigen in spot 8 by mass spectroscopy, the amino acid sequences of SEQ ID NOs: 153-235 were detected.

Also, the mass spectroscopic data (SEQ ID NOs: 153-235) obtained for spot 8 on a mass spectrometer was analyzed by comparing the data against the NCBI protein data, and as a result, the antigen in question was identified as Apolipoprotein B precursor (amino acid sequence: SEQ ID NO: 152, encoding nucleotide sequence: SEQ ID NO: 151).

Accordingly, in the present invention, the antigen in spot 8 can be any of (7A-a) to (7A-e) and (7B) as defined below:

(7A-a) a protein comprising an amino acid sequence with deletion, substitution, insertion or addition of one or several amino acids in SEQ ID NO: 152;

(7A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 152;

(7A-c) a protein comprising an amino acid sequence encoded by a nucleotide sequence with deletion, substitution, insertion or addition of one or several nucleotides in SEQ ID NO: 151;

(7A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 151;

(7A-e) a protein comprising an amino acid sequence encoded by a nucleic acid that hybridizes under stringent conditions with a nucleic acid having a nucleotide sequence complementary to the nucleotide sequence of SEQ ID NO: 151;

(7B) a protein comprising at least one amino acid sequence selected from the group consisting of SEQ ID NOs: 152-235, preferably a protein comprising at least 2, 3, 4, 5, 6, 7, 8, 9, 10, 15, 20, 25, 30, 35, 40, 45, 50, 55, 60, 65, 70, 75, 80, 83 or all sequences of the amino acid sequences; more preferably a protein comprising at least one amino acid sequence selected from the group consisting of SEQ ID NOs: 152, 154, 157-160, 163, 164, 167-172, 174, 175, 177, 178, 180, 182-185, 187, 189, 190, 192, 194-196, 198-200, 203-207, 209, 211, 212, 214-216, 220-229, 231 and 232, preferably a protein comprising at least 2, 3, 4, 5, 6, 7, 8, 9, 10, 15, 20, 25, 30, 35, 40, 45, 50, 55 or all sequences of the amino acid sequences. As referred to above, the amino acid sequence of any of SEQ ID NOs: 152-235 may be an amino acid sequence derived therefrom by deletion, substitution, insertion or addition of one or several amino acids.

The proteins of (7A-a) to (7A-e) and (7B) as defined above can be proteins that are found in a protein spot with a molecular weight of around 160 to 550 kDa, preferably around 180 to 400 kDa, more preferably around 200 to 300 kDa and an isoelectric point of 3.0 to 8.0, preferably 3.5 to 7.0, more preferably 4.0 to 6.0 on gels used in the two-dimensional electrophoresis performed under the conditions described above in the subsection titled "Identification of antigens".

(8) Antigen in Spot 9

As the result of sequence identification of the antigen in spot 9 by mass spectroscopy, the amino acid sequences of SEQ ID NOs: 238-249 were detected.

Also, the mass spectroscopic data (SEQ ID NOs: 238-249) obtained for spot 9 on a mass spectrometer was analyzed by comparing the data against the NCBI protein data, and as a result, the antigen in question was identified as Apolipoprotein B precursor (amino acid sequence: SEQ ID NO: 237, encoding nucleotide sequence: SEQ ID NO: 236).

Accordingly, in the present invention, the antigen in spot 9 can be any of (8A-a) to (8A-e) and (8B) as defined below:

(8A-a) a protein comprising an amino acid sequence with deletion, substitution, insertion or addition of one or several amino acids in SEQ ID NO: 237;

(8A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 237;

(8A-c) a protein comprising an amino acid sequence encoded by a nucleotide sequence with deletion, substitution, insertion or addition of one or several nucleotides in SEQ ID NO: 236;

(8A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 236;

(8A-e) a protein comprising an amino acid sequence encoded by a nucleic acid that hybridizes under stringent conditions with a nucleic acid having a nucleotide sequence complementary to the nucleotide sequence of SEQ ID NO: 236;

(8B) a protein comprising at least one amino acid sequence selected from the group consisting of SEQ ID NOs: 237-249, preferably a protein comprising at least 2, 3, 4, 5, 6, 7, 8, 9, 10, 11, 12 or all sequences of the amino acid sequences. More preferably, a protein comprising at least one amino acid sequence selected from the group consisting of SEQ ID NOs: 237-239, 241, 242, 244, and 246-249; preferably a protein comprising at least 2, 3, 4, 5, 6, 7, 8, 9, or all sequences of the amino acid sequences. As referred to above, the amino acid sequence of any of SEQ ID NOs: 237-249 may be an amino acid sequence derived therefrom by deletion, substitution, insertion or addition of one or several amino acids.

The proteins of (8A-a) to (8A-e) and (8B) as defined above can be proteins that are found in a protein spot with a molecular weight of around 20 to 50 kDa, preferably around 25 to 45 kDa, more preferably around 30 to 40 kDa and an isoelectric point of 7.0 to 11.0, preferably 8.0 to 10.0, more preferably 9.0 to 10.0 on gels used in the two-dimensional electrophoresis performed under the conditions described above in the subsection titled "Identification of antigens".

(9) Antigen in Spot 10

As the result of sequence identification of the antigen in spot 10 by mass spectroscopy, the amino acid sequences of SEQ ID NOs: 252-260 were detected.

Also, the mass spectroscopic data (SEQ ID NOs: 252-260) obtained for spot 10 on a mass spectrometer was analyzed by comparing the data against the NCBI protein data, and as a result, Apolipoprotein B precursor (amino acid sequence: SEQ ID NO: 251, encoding nucleotide sequence: SEQ ID NO: 250) was identified was identified.

Accordingly, the antigen in spot 10 in the present invention can be any of proteins selected from the group consisting of the proteins as defined below in (9A-a) to (9A-e), and (9B):

(9A-a) a protein comprising an amino acid sequence with deletion, substitution, insertion or addition of one or several amino acids in SEQ ID NO: 251;

(9A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 251;

(9A-c) a protein comprising an amino acid sequence encoded by a nucleotide sequence with deletion, substitution, insertion or addition of one or several nucleotides in SEQ ID NO: 250;

(9A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 250;

(9A-e) a protein comprising an amino acid sequence encoded by a nucleic acid that hybridizes under stringent conditions with a nucleic acid having a nucleotide sequence complementary to the nucleotide sequence of SEQ ID NO: 250;

(9B) a protein comprising at least one amino acid sequence selected from the group consisting of SEQ ID NOs: 251-260, preferably a protein comprising at least 2, 3, 4, 5, 6, 7, 8, 9 or all sequences of the amino acid sequences. More preferably, a protein comprising at least one amino acid sequence selected from the group consisting of SEQ ID NOs: 251-254, 256, 257, and 260; preferably a protein comprising at least 2, 3, 4, 5, 6, or all sequences of the amino acid sequences. As referred to above, the amino acid sequence of any of SEQ ID NOs: 251-260 may be an amino acid sequence derived therefrom by deletion, substitution, insertion or addition of one or several amino acids;

The proteins of (9A-a) to (9A-e) and (9B) as defined above can be proteins that are found in a protein spot with a molecular weight of around 20 to 50 kDa, preferably 25 to 40 kDa, more preferably 30 to 40 kDa and an isoelectric point of 7.0 to 11.0, preferably 8.0 to 10.0, more preferably 9.0 to 10.0 on gels used in the two-dimensional electrophoresis performed under the conditions described above in the subsection titled "Identification of antigens".

(10) Antigen in Spot 11

As the result of sequence identification of the antigen in spot 11 by mass spectroscopy, the amino acid sequences of SEQ ID NOs: 263-271 were detected.

Also, the mass spectroscopic data (SEQ ID NOs: 263-271) obtained for spot 11 on a mass spectrometer was analyzed by comparing the data against the NCBI protein data, and as a result, Vitellogenin-2 precursor (amino acid sequence: SEQ ID NO: 262, encoding nucleotide sequence: SEQ ID NO: 261) was identified.

Accordingly, the antigen in spot 11 in the present invention can be any of proteins selected from the group consisting of the proteins as defined below in (10A-a) to (10A-e) and (10B):

(10A-a) a protein comprising an amino acid sequence with deletion, substitution, insertion or addition of one or several amino acids in SEQ ID NO: 262;

(10A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 262;

(10A-c) a protein comprising an amino acid sequence encoded by a nucleotide sequence with deletion, substitution, insertion or addition of one or several nucleotides in SEQ ID NO: 261;

(10A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 261;

(10A-e) a protein comprising an amino acid sequence encoded by a nucleic acid that hybridizes under stringent conditions with a nucleic acid having a nucleotide sequence complementary to the nucleotide sequence of SEQ ID NO: 261; (10B) a protein comprising at least one amino acid sequence selected from the group consisting of SEQ ID NOs: 262-271, preferably a protein comprising at least 2, 3, 4, 5, 6, 7, 8, 9 or all sequences of the amino acid sequences. More preferably, a protein comprising at least one amino acid sequence selected from the group consisting of SEQ ID NOs: 262-265, 268, and 269; preferably a protein comprising at least 2, 3, 4, 5, or all sequences of the amino acid sequences. As referred to above, the amino acid sequence of any of SEQ ID NOs:262 to 271 may be an amino acid sequence derived therefrom by deletion, substitution, insertion or addition of one or several amino acids.

The proteins of (10A-a) to (10A-e) and (10B) as defined above can be proteins that are found in a protein spot with a molecular weight of around 15 to 40 kDa, preferably 17 to 35 kDa, more preferably 20 to 30 kDa and an isoelectric point of 6.0 to 11.0, preferably 7.0 to 10.0, more preferably 8.0 to 10.0 on gels used in the two-dimensional electrophoresis performed under the conditions described above in the subsection titled "Identification of antigens".

The antigen proteins of (1) to (3) and (4) to (10) as defined above also include those proteins whose amino acid residues are modified by phosphorylation, sugar chain modification, aminoacylation, ring-opening, deamination or the like.

Preferably, the antigen proteins of (1) to (3) and (4) to (10) as defined above are antigens for an egg allergy.

By stating herein "deletion, substitution, insertion or addition of one or several amino acids" in relation to amino acid sequence, it is meant that in an amino acid sequence of interest, one or several amino acids (e.g., 30%, preferably 25%, 20%, 15%, 10%, 5%, 3%, 2%, or 1% of amino acids with respect to the total length of the amino acid sequence) are deleted, one or several amino acids are substituted by any other amino acids, any other amino acids are inserted, and/or any other amino acids are added.

Among the aforementioned modifications, substitution is preferably conservative substitution. The "conservative substitution" refers to the substitution of a certain amino acid residue by a different amino acid residue having similar physicochemical characteristics, and can be any type of substitution as long as it does not substantially change the characteristics of the structure of the original sequence for example, any type of substitution is acceptable as long as any substituted amino acids do not disrupt the helical structure of the original sequence or other secondary structures that characterize the original sequence. The following gives examples of separate groups of amino acid residues that are conservatively substitutable with each other, but substitutable amino acid residues are not limited to the examples given below.

Group A: leucine, isoleucine, valine, alanine, methionine

Group B: aspartic acid, glutamic acid

Group C: asparagine, glutamine

Group D: lysine, arginine

Group E: serine, threonine

Group F: phenylalanine, tyrosine

In the case of non-conservative substitution, one member belonging to one of the aforementioned groups can be replaced with a member belonging to any other group. For example, in order to eliminate the possibility of unwanted sugar-chain modification, amino acids of group B, D or E as listed above may be substituted by those of any other group. Also, cysteines may be deleted or substituted by any other amino acids to prevent them from being folded into a protein in its tertiary structure. Also, in order to maintain the balance between hydrophilicity and hydrophobicity or to increase hydrophilicity for the purpose of facilitating synthesis, any amino acids may be substituted in consideration of the hydropathy scales of amino acids, which are a measure of the hydrophilic and hydrophobic properties of amino acids (J. Kyte and R. Doolittle, J. Mol. Biol., Vol. 157, p. 105-132, 1982).

As referred to herein, the percent identity between two amino acid sequences can be determined by visual inspection and mathematical calculation. Alternatively, the percent identity can be determined using a computer program. Examples of such computer programs include BLAST and ClustalW. In particular, various conditions (parameters) for identity searches with the BLAST program are described in Altschul, et al. (Nucl. Acids. Res., 25, p. 3389-3402, 1997), and are publicly available on the websites of the National Center for Biotechnology Information (NCBI) and DNA Data Bank of Japan (DDBJ) (Altschul, et al., BLAST Handbook, Altschul, et al., NCB/NLM/NIH Bethesda, MD 20894). Also, the percent identity can be determined using a genetic information processing software program, such as GENETYX Ver. 7 (Genetyx Corporation), DINASIS Pro (Hitachi Software Engineering Co., Ltd.), or Vector NTI (Infomax Inc.).

By stating herein "deletion, substitution, insertion or addition of one or several nucleotides" in relation to nucleotide sequence, it is meant that in a nucleotide sequence of interest, one or several nucleotides (e.g., 30%, preferably 25%, 20%, 15%, 10%, 5%, 3%, 2% or 1%, of nucleotides with respect to the total length of the nucleotide sequence) are deleted, one or several nucleotides are substituted by any other nucleotides, any other nucleotides are inserted, and/or any other nucleotides are added. It is preferable that such a nucleotide deletion, substitution, insertion or addition should not give rise to a frame shift in an amino acid coding sequence.

As referred to herein, the percent identity between two nucleotide sequences can be determined by visual inspection and mathematical calculation. Alternatively, the percent identity can be determined using a computer program. Examples of such sequence comparison computer programs include the BLASTN program available on the website of the National Library of Medicine (Altschul et al. (1990) J. Mol. Biol. 215: 403-10), and it can be determined by using default parameters.

As referred to herein, "under stringent conditions" means that hybridization takes place under moderately or highly stringent conditions. To be specific, the moderately stringent conditions can be easily determined by those having ordinary skill in the art on the basis of, for example, the length of DNA. Basic conditions are described in Sambrook, et al., Molecular Cloning: A Laboratory Manual, 3rd ed., ch. 6-7, Cold Spring Harbor Laboratory Press, 2001. The moderately stringent conditions include hybridization under the conditions of preferably 1×SSC to 6×SSC at 42° C. to 55° C., more preferably 1×SSC to 3×SSC at 45° C. to 50° C., most preferably 2×SSC at 50° C. In the case of using a hybridization solution containing, for example, about 50% formamide, a temperature around 5 to 15° C. lower than the foregoing should be adopted. Washing is also carried out under the conditions of 0.5×SSC to 6×SSC at 40° C. to 60° C. In the process of hybridization and washing, generally 0.05% to 0.2% SDS, preferably about 0.1% SDS, may be added. Likewise, the highly stringent conditions can be easily determined by those having ordinary skill in the art on the basis of, for example, the length of DNA. Generally, the highly stringent (high stringent) conditions include hybridization and/or washing at a higher temperature and/or a lower salt concentration than those adopted under the moderately stringent conditions. For example, hybridization is carried out under the conditions of 0.1×SSC to 2×SSC at 55° C. to 65° C., more preferably 0.1×SSC to 1×SSC at 60° C. to 65° C., most preferably 0.2×SSC at 63° C. Washing is carried out under the conditions of 0.2×SSC to 2×SSC at 50° C. to 68° C., more preferably 0.2×SSC at 60 to 65° C.

Antigens may be obtained by separating and purifying them from eggs (preferably chicken eggs) using a combination of protein purification methods well known to those skilled in the art. Also, antigens may be obtained by expressing them as recombinant proteins using a genetic recombination technique well known to those skilled in the art and by separating and purifying them using protein purification methods well known to those skilled in the art.

Exemplary protein purification methods include: solubility-based purification methods such as salt precipitation and solvent precipitation; purification methods based on molecular weight difference, such as dialysis, ultrafiltration, gel filtration and SDS-PAGE; charge-based purification methods such as ion exchange chromatography and hydroxylapatite chromatography; specific affinity-based purification methods such as affinity chromatography; purification methods based on hydrophobicity difference, such as reverse-phase high-performance liquid chromatography; and purification methods based on isoelectric point difference, such as isoelectric focusing.

Preparation of a protein by a genetic recombination technique is carried out by preparing an expression vector comprising an antigen-encoding nucleic acid, introducing the expression vector into appropriate host cells by gene transfer or genetic transformation, culturing the host cells under suitable conditions for expression of a recombinant protein, and recovering the recombinant protein expressed in the host cells.

The "vector" refers to a nucleic acid that can be used to introduce a nucleic acid attached thereto into host cells. The "expression vector" is a vector that can induce the expression of a protein encoded by a nucleic acid introduced therethrough. Exemplary vectors include plasmid vectors and viral vectors. Those skilled in the art can select an appropriate expression vector for the expression of a recombinant protein depending on the type of host cells to be used.

The "host cells" refers to cells that undergo gene transfer or genetic transformation by a vector. The host cells can be appropriately selected by those skilled in the art depending on the type of the vector to be used. The host cells can be derived from prokaryotes such as E. coli. When prokaryotic cells like E. coli. are used as host cells, the antigen of the present invention may be designed to contain an N-terminal methionine residue in order to facilitate the expression of a recombinant protein in the prokaryotic cells. The N-terminal methionine can be cleaved from the recombinant protein after expression. Also, the host cells may be cells derived from eukaryotes, such as single-cell eukaryotes like yeast, plant cells and animal cells (e.g., human cells, monkey cells, hamster cells, rat cells, murine cells or insect cells) or silkworm.

Gene transfer or genetic transformation of an expression vector into host cells can be carried out as appropriate by following a technique known to those skilled in the art. Those skilled in the art can make possible the expression of a recombinant protein by selecting suitable conditions for the expression of the recombinant protein as appropriate depending on the type of host cells and culturing the host cells under the selected conditions. Then, those skilled in the art can homogenize the host cells having the expressed recombinant protein, and separate and purify an antigen expressed as the recombinant protein from the resulting homogenate by using an appropriate combination of such protein purification methods as mentioned above.

Diagnosis Kit and Method

The present invention provides a method for providing an indicator for diagnosing an allergy to an egg in a subject, the method comprising the steps of:

(i) contacting a sample obtained from the subject with an antigen, wherein the sample is a solution comprising an IgE antibody;

(ii) detecting binding between an IgE antibody present in the sample from the subject and the antigen; and (iii) when the binding between the IgE antibody in the subject and the antigen is detected, an indicator of the fact that the subject is allergic to an egg is provided;

wherein the antigen is at least one of proteins as defined above in any of (1) to (3) and (4) to (10).

The sample obtained from a subject is a solution containing an IgE antibody, as collected from the subject. Examples of such solutions include blood, saliva, sputum, snivel, urine, sweat, and tear. The sample obtained from the subject may be subjected to pretreatment for increasing the concentration of an IgE antibody in the sample before being contacted with an antigen. The pretreatment of a sample may involve, for example, collection of the serum, plasma from the blood. Furthermore, a Fab portion that is a binding portion with the antigen may be purified. In a particularly preferred mode, the step (i) mentioned above is carried out by contacting an IgE antibody present in the serum obtained from a subject with an antigen.

The IgE antibody may be the IgE antibody itself or mast cells or the like to which the IgE antibody is bound.

Detection of contact and binding between the sample obtained from a subject and an antigen can be carried out by using a known method. Examples of such methods that can be used include detection by ELISA (Enzyme-Linked Immunosorbent Assay), sandwich immunoassay, immunoblotting, immunoprecipitation, or immunochromatography. These are all techniques for detecting binding between an antigen and an IgE antibody from a subject by contacting and binding the IgE antibody from a subject with the antigen, allowing an enzymatically labelled secondary antibody to act on the IgE antibody specifically bound to the antigen, and adding an enzyme substrate (generally, chromogenic or luminescent reagent) to detect an enzymatic reaction product. Also, a method for detecting a fluorescently labeled secondary antibody can be used. Also, detection by a measurement method that permits the analysis of binding between an antigen and an IgE antibody, such as surface plasmon resonance (SPR), can be used. A plurality of antigen-specific IgE antibodies may be mixed.

The antigen may be provided as an isolated antigen in a state immobilized on a carrier. In this case, the steps (i) and (ii) mentioned above can be carried out using ELISA, sandwich immunoassay, immunochromatography, surface plasmon resonance, or the like. Also, the step (i) mentioned above is carried out by contacting the sample obtained from a subject with an antigen-immobilized surface. The isolated antigen may be obtained by separating and purifying it from egg (preferably chicken egg) using a combination of protein purification methods well known to those skilled in the art, or by preparing it using a genetic recombination technique. Moreover, the antibody may be in an immobilized state.

The antigen may be in a state unfixed on a carrier. In this case, the steps (i) and (ii) mentioned above can be carried out by flow cytometry or the like and the presence of the antigen bound to an antibody may be confirmed using a laser beam. Examples include basophil activation test (BAT) and the like. Another example is histamine release test (HRT) in which it is examined whether histamine is released or not by bringing an antigen further in contact with hemocytes in a sample.

The antigen may be detected by immunoblotting in a state separated by two-dimensional electrophoresis. The two-dimensional electrophoresis is a technique for separating a protein sample by performing isoelectric focusing in the first dimension and performing SDS-PAGE (SDS-polyacrylamide gel electrophoresis) in the second dimension. The conditions for two-dimensional electrophoresis are not particularly limited as long as the conditions permit the separation of the antigen of the present invention. For example, the conditions for two-dimensional electrophoresis as described above in the subsection titled "Identification of antigens" can be adopted. Also, the electrophoresis conditions may be defined by reference to the descriptions in PTLs 1 to 4 mentioned above. For example, two-dimensional electrophoresis can be carried out under the conditions that satisfy at least one selected from the group consisting of the following requirements:

(A) the isoelectric focusing gels used in the first dimension should have a gel-strip length of 5 to 10 cm and a gel pH range of 3 to 10, and the pH gradient of the gels in the direction of electrophoresis should be as follows: where the gel-strip length up to pH 5 is taken as "a", that length from pH 5 to 7 as "b", and that length above pH 7 as "c", the relations "a<b" and "b>c" are satisfied;

(B) in the case of (A), when the total gel-strip length is taken as 1, "a" should be in the range of 0.15 to 0.3, "b" should be in the range of 0.4 to 0.7, and "c" should be in the range of 0.15 to 0.3;

(C) in the first dimensional isoelectric focusing, a constant voltage step should be performed by applying a constant voltage ranging from 100 V to 600 V per gel strip containing a sample, and after the electrophoresis variation width during electrophoresis for 30 minutes falls within the range of 5 μA, a voltage-increasing step should be started at which the voltage is increased from the aforementioned constant voltage;

(D) in the case of (C), the final voltage at the voltage-increasing step should be in the range of 3000 V to 6000 V;

(E) the isoelectric focusing gels used in the first dimension should have a longitudinal gel-strip length of 5 to 10 cm, and the electrophoresis gels used in the second dimension should have a gel concentration at the distal end in the direction of electrophoresis, which is in the range of 3 to 6%; and (F) in the case of (E), the electrophoresis gels used in the second dimension should have a gel concentration at the proximal end in the direction of electrophoresis, which is set to a higher value than that at the distal end in the direction of electrophoresis.

The aforementioned antigens (1) to (3) and (4) to (10) are antigens that specifically bind to IgE antibodies from patients with allergy to egg. Therefore, when binding between an IgE antibody from a subject and the antigen is detected, an indicator of the fact that the subject is allergic to egg is provided.

The present invention further provides a kit for diagnosing an allergy to an egg, comprising at least one of the aforementioned antigens (1) to (3) and (4) to (10). The diagnosis kit of this invention may be used in the aforementioned method for providing an indicator for diagnosing an allergy to an egg or in a diagnosis method as described later. The diagnosis kit of this invention may comprise not only the at least one of the aforementioned antigens (1) to (3) and (4) to (10), but also an anti-IgE antibody labeled with an enzyme and a chromogenic or luminescent substrate serving as a substrate for the enzyme. Also, a fluorescent-labeled anti-IgE antibody may be used. In the diagnosis kit of this invention, the antigen may be provided in a state immobilized on a carrier. The diagnosis kit of this invention may also be provided together with instructions on the procedure for diagnosis or a package containing said instructions.

In another aspect, the diagnosis kit includes a companion diagnostic agent for an egg allergy. The companion diagnostic agent is used to analyze the reactivity of a pharmaceutical product for the purpose of identifying a patient in which the pharmaceutical product is expected to work or a patient at risk for serious side effects from the pharmaceutical product, or optimizing a therapy using the pharmaceutical product. Here, examples of optimizing a therapy include determination of the usage and the volume, decision of stopping the administration, determination of the allergen component to be used for the induction of immune tolerance, and the like.

The present invention further provides a composition for diagnosing an allergy to an egg, comprising at least one of the aforementioned antigens (1) to (3) and (4) to (10). The diagnosis composition of this invention can be used in a diagnosis method as described below. The diagnosis composition of this invention may further comprise a pharmaceutically acceptable carrier and/or additives commonly used with the antigen of this invention depending on the need.

In one mode, the present invention provides a method for diagnosing an allergy to an egg in a subject, the method comprising:

(i) contacting a sample obtained from the subject with an antigen;

(ii) detecting binding between an IgE antibody present in the sample from the subject and the antigen; and (iii) when the binding between the IgE antibody in the subject and the antigen is detected, diagnosing the subject as being allergic to an egg;

wherein the antigen is at least one of proteins as defined above in any of (1) to (3) and (4) to (10). In this method, the steps (i) and (ii) are performed as described above regarding the corresponding steps of the method for providing an indicator for diagnosing an allergy to an egg.

In another mode, the present invention provides a method for diagnosing an allergy to an egg in a subject, the method comprising administering to the subject at least one of the aforementioned antigens (1) to (3) and (4) to (10). This method may be performed in the form of a skin test characterized by applying the antigen onto the skin. Examples of the skin test include various forms of tests, such as: a prick test in which a diagnosis composition is applied onto the skin and then a tiny prick to such an extent as not to provoke bleeding is made in the skin to allow an antigen to penetrate the skin, thereby observing a skin reaction; a scratch test in which a diagnosis composition is applied onto the skin and then the skin is lightly scratched to observe a reaction; a patch test in which a diagnosis composition in the form of cream, ointment, etc. is applied onto the skin to observe a reaction; and an intracutaneous test in which an antigen is administered intracutaneously to observe a reaction. If a skin reaction such as swelling occurs in a skin portion to which the antigen has been applied, the subject of interest is diagnosed as having an allergy to an egg. The amount of the antigen to be applied to the skin in such tests can be, for example, not more than 100 µg per dose.

In the allergic diagnosis, a load test for the purpose of identifying the antigen is often performed. At least one of the aforementioned antigens (1) to (3) and (4) to (10) can be used as an active ingredient(s) in such a load test for diagnosing an egg allergy. Here, the antigen protein to be used in the load test may be a protein that has been expressed and purified and may be a protein that has been expressed in a food and a food material, for example, rice-based vaccine produced by transforming rice with a gene of a cedar pollen antigen to express the antigen protein therein.

In yet another mode, the present invention provides at least one of the aforementioned antigens (1) to (3) and (4) to (10), intended for use in the diagnosis of an allergy to an egg. Here, the present invention encompasses the provision of at least one of the aforementioned antigens (1) to (3) and (4) to (10) mixed with a known antigen.

In still another mode, the present invention provides use of at least one of the aforementioned antigens (1) to (3) and (4) to (10) for the production of a diagnostic agent for an allergy to an egg.

Pharmaceutical Composition and Treatment Method

The present invention provides a pharmaceutical composition comprising at least one of the aforementioned antigens (1) to (3) and (4) to (10).

In one mode, the aforementioned pharmaceutical composition is used for the treatment of an allergy to an egg.

The present invention also provides a method for treating an allergy to an egg, the method comprising administering at least one of the aforementioned antigens (1) to (3) and (4) to (10) to a patient in need of a treatment for an allergy to an egg.

In another mode, the present invention provides at least one of the aforementioned antigens (1) to (3) and (4) to (10), intended for use in the treatment for an allergy to an egg. In yet another mode, the present invention provides use of at least one of the aforementioned antigens (1) to (3) and (4) to (10) for the production of a therapeutic agent for an allergy to an egg.

In the process of allergy treatment, a hyposensitization therapy aiming to induce immunological tolerance by administering an antigen to a patient is often adopted. The at least one of the aforementioned antigens (1) to (3) and (4) to (10) can be used as an active ingredient for a hyposensitization therapy for an allergy to an egg. Here, the antigen protein to be used in the hyposensitization therapy may be a protein that has been expressed and purified and may be a protein that has been expressed in a food and a food material, for example, rice-based vaccine produced by transforming rice with a gene of a cedar pollen antigen to express the antigen protein therein.

The pharmaceutical composition of the present invention can be administered by common administration routes. Examples of common administration routes include oral, sublingual, percutaneous, intracutaneous, subcutaneous, intravascular, intranasal, intramuscular, intraperitoneal, and intrarectal administrations.

The pharmaceutical composition of the present invention can be used as a pharmaceutical composition to which a commonly used pharmaceutically acceptable adjuvant or excipient or any other additives (e.g., stabilizer, solubilizer, emulsifier, buffer, preservative, colorant) are added by a conventional method together with the antigen of this invention depending on the need. The dosage form of the pharmaceutical composition can be selected by those skilled in the art as appropriate depending on the administration route. The pharmaceutical composition can be in the form of, for example, tablet, capsule, troche, sublingual tablet, injection, intranasal spray, poultice, solution, cream, lotion, or suppository. The administration dose, frequency and/or period of the pharmaceutical composition of this invention can be selected by a physician as appropriate depending on the administration route and the patient's condition and characteristics such as age and body weight. For example, the pharmaceutical composition may be administered to an adult patient at a dose of not more than 100 µg per dose. The administration interval can be, for example, once daily, once weekly, twice weekly, once per three months or so. The administration period can be, for example, several weeks to several years. The pharmaceutical composition may be administered in such a manner that the dose is increased in incremental steps over the administration period.

Tester

The present invention provides a tester comprising an antibody for at least one of the aforementioned antigens (1) to (3) and (4) to (10).

The antibody can be prepared by a conventional method. For example, the antibody may be prepared by immunizing a mammal such as rabbit with one of the aforementioned antigens (1) to (3) and (4) to (10). The antibody may be an IgE antibody, a polyclonal antibody, a monoclonal antibody, or an antigen-binding fragment thereof (e.g., Fab, $F(ab')_2$, Fab').

Further, in the aforementioned tester, the antibody may be provided in a form bound to a carrier. The type of the carrier is not particularly limited as long as it is usable for detection of binding between an antibody and an antigen. Any given carrier known to those skilled in the art can be used.

Examples of a method for determining the presence or absence of an antigen include the following:

A method in which a prepared tester comprising an IgE antibody is contacted with a sample obtained from a food, food material, etc., ELISA or the like method is used to detect whether there is a binding between the IgE antibody and an antigen in the sample, and if the binding between the IgE antibody and the antigen is detected, it is determined that the antibody is present in the food, food material, etc. of interest.

A method in which a food or a food material is infiltrated into a filter paper or the like and an antibody solution is reacted with the filter paper to detect an antigen present in the food or food material.

In another aspect, the present invention encompasses a tester for determining the presence or absence of an antigen for an egg allergy in an object of interest, comprising a primer having a nucleotide sequence complementary to a part of at least one of the nucleotide sequences set forth in SEQ ID NO: 1, 12, 17, 46, 58, 105, 151, 236, 250, or 261. Without limiting, the primer has a nucleotide sequence complementary to preferably 12 bases, 15 bases, 20 bases, or 25 bases in the sequence of a 3' terminal or middle portion of a part of at least one sequence of the nucleotide sequences set forth in, for example, SEQ ID NO: 1, 12, 17, 46, 58, 105, 151, 236, 250, or 261. Particularly when mRNA is targeted, the tester comprises a poly A tail-complementarity primer. In a preferred aspect, the tester including the primer may further comprise a primer comprising a nucleotide sequence of a 5' terminal portion of at least one sequence of the nucleotide sequences set forth in SEQ ID NO: 1, 12, 17, 46, 58, 105, 151, 236, 250, or 261, preferably a nucleotide sequence consisting of 12 bases, 15 bases, 20 bases, 25 bases.

For example, the presence or absence of the antigen is determined by amplifying cDNA by polymerase chain reaction (PCR) including RT-PCR with DNA or mRNA obtained from an egg or a bird as a template and the complementary primer and comparing the amplified cDNA sequence(s) with SEQ ID NO: 1, 12, 17, 46, 58, 105, 151, 236, 250, or 261. Examples of the method of the amplification by PCR include RACE and the like. In the determination, the antigen is determined to be present when the comparison between the amplified cDNA and SEQ ID NO: 1, 12, 17, 46, 58, 105, 151, 236, 250, or 261 indicates the presence of one or more point mutations encoding the same amino acid, or when the amino acid sequence encoded by the amplified cDNA has 70% or more, preferably 80, 90, 95, 98, or 99% or more identity with an amino acid sequence of SEQ ID NO: 2, 13, 18, 47, 59, 106, 152, 237, 251 or 262, even if the nucleotide sequence of the amplified cDNA is modified from a nucleotide sequence of SEQ ID NO: 1, 12, 17, 46, 58, 105, 151, 236, 250, or 261 by insertion, deletion, substitution, or addition of one or more nucleotides.

In one mode, the aforementioned tester is used to determine the presence or absence of an antigen in foods or in products of interest in a food material (egg or bird) or a food production line. The tester may also be used for quality inspection of production lines and pre-shipment products by manufacturers, or may be used for self-checking of the presence or absence of an antigen in a food, food material of interest by consumers.

Antigen-Free Food and the Like

The present invention provides an egg, a processed product of an egg, or a bird which lays or has hatched from the egg in which at least one of the aforementioned antigens (1) to (3) and (4) to (10) is eliminated or reduced.

The method for eliminating or reducing the antigen of the present invention in an egg, a processed product of an egg, or a bird which lays or has hatched from the egg is not limited. The elimination or reduction of the antigen may be conducted by any method, as long as the method permits the elimination or reduction of the antigen.

For example, the egg of the present invention whose antigen is eliminated or reduced may be obtained by preparing an egg in which the expression of the antigen of the present invention is knocked out, using a gene knock-out technique.

As the gene knock-out technique, there can be used any methods known to those skilled in the art. For example, Oishi, et al. (Scientific Reports, Vol. 6, Article number: 23980, 2016, doi:10.1038/srep23980) describes that the genome editing technique CRISPER/Cas9 is applied to chicken primordial germ cells to obtain individual animals deficient in ovomucoid gene. The egg devoid of the antigen of this invention may also be obtained by using the same technique as above. Moreover, a bird or an egg in which the antigen of the present invention is eliminated or decreased may be obtained by mating by artificial insemination with a bird or an egg that does not contain the antigen or contains a low content of the antigen. The artificial mating of birds or eggs can be performed by a conventional method.

An antigen of the present invention may be the artefact that an antigen of the present invention assumed the removal or a reduced egg raw material as for the removal or the reduced processed products of egg. In the case of using an ordinary egg as a source ingredient, a treatment for removing or reducing the antigen of this invention is performed before or after preparation of a processed product of egg. Examples of a method of eliminating or decreasing the antigen of the present invention in a processed product made from a common egg include methods for eliminating the protein component in a food or a food material, such as elution with a high pressure treatment and a neutral salt solution and hot steam and methods for hydrolysis, denaturation, or amino acid modification (chemical modification or elimination of side chains) by heat treatment and acid treatment.

The bird in which the antigen of the present invention is eliminated or reduced may be a bird that has hatched and grown from an egg in which the aforementioned antigen of the present invention is eliminated or reduced. The birds include birds at growth stages of nestling, juvenile, young bird, adult bird and old bird. As used herein, the bird means an animal belonging to Aves, preferably a chicken.

Method for Producing Antigen-Free Processed Product of Egg

The present invention provides a method for producing a processed product of an egg in which an antigen is eliminated or reduced, comprising the step of confirming that the antigen is eliminated or reduced in the process of producing the processed product, wherein the antigen is at least one of the aforementioned antigens (1) to (3) and (4) to (10).

The step of confirming that the antigen is eliminated or reduced in the process of producing the processed product of an egg in which an antigen is eliminated or reduced may be performed by examining whether the antigen is contained or not by the method described in the section of "Tester" above.

The method for producing a processed product of an egg in which an antigen is eliminated or reduced may be performed by the method described in the section "Antigen-free food and the like" above.

EXAMPLES

The following describes examples of the present invention. The technical scope of this invention is not limited by these examples.

Example 1: Confirmation of a Protein Pattern

Proteins contained in egg were investigated using a two-dimensional electrophoresis method described below.

Protein Extraction

Raw chicken eggs were separated into egg white and egg yolk.

The extraction and the purification of proteins contained in the egg white and the egg yolk were performed as follows. A solubilization agent was added to the egg white to extract proteins and then water or a urea buffer was added to obtain a protein extract. The composition of the urea buffer is as follows.

30 mM Tris
2 M Thiourea
7 M Urea
4% (w/v) CHAPS:
3-[(3-Cholamidopropyl)dimethylammonio]propane-sulfonate
A proper quantity of dilute hydrochloric acid Distilled water was added and the total volume was adjusted to 100 mL. PH was 8.5. Subsequently, 25 µg each in terms of protein weight was mixed to obtain an extract. A surfactant buffer (Mammalian Lysis Buffer (MCLI), SIGMA) was added as a solubilization agent to the egg yolk to extract proteins.

Thereafter, the precipitation procedure was repeated twice using a 2D-CleanUP Kit (produced by GE). In the first round of precipitation, the collected liquid protein extract was precipitated by adding TCA (trichloroacetic acid) thereto and the precipitated product produced by this procedure (TCA-precipitated product) was collected. In the second round of precipitation, the TCA-precipitated product collected above was further precipitated by adding acetone thereto and the precipitated product (sample) produced by this procedure was collected.

Preparation of a Sample Solution

Part of the collected sample (50 µg on a protein weight basis) was dissolved in 150 µL of a DeStreak Rehydration Solution (produced by GE), which is a swelling buffer for first-dimensional isoelectric focusing gels, thereby obtaining a sample solution for first-dimensional isoelectric focusing (sample solution for swelling). The constituents of the DeStreak Rehydration Solution are as mentioned below.

7M thiourea
2M urea
4% (w/v) of CHAPS
0.5% (v/v) IPG buffer; produced by GE
Moderate amount of BPB (bromophenol blue)

Penetration of the sample into first-dimensional isoelectric focusing gels First-dimensional isoelectric focusing gel strips (Immobiline Drystrip IPG gels (pH3-10NL); produced by GE) were immersed in 140 µL of the foregoing sample solution for first-dimensional isoelectric focusing (sample solution for swelling) and impregnated with the solution at room temperature overnight.

In this example, an IPGphor electrophoresis system produced by GE was used.

An electrophoresis tray was filled with silicone oil. Filter paper moisten with water was positioned at both ends of the gel strips impregnated with the sample, and the gel strips were set in the electrophoresis tray such that the gel strips were covered with silicone oil. Electrodes were placed on the gel strips with the filter paper intervening therebetween.

The maximum current of the isoelectric focusing system was set to 75 µA per gel strip, and the first-dimensional isoelectric focusing was carried out according to the following voltage program: (1) a constant voltage step was performed at a constant voltage of 300 V until the volt-hours reached 750 Vhr (the current variation width during electrophoresis for 30 minutes before the end of this step was 5 µA); (2) the voltage was increased gradually to 1000 V for 300 Vhr; (3) the voltage was further increased gradually to 5000 V for 4500 Vhr; and then (4) the voltage was held at a constant voltage of 5000 V until the total Vhr reached 12000.

SDS Equilibration of Isoelectric Focusing Gels

After the aforementioned first-dimensional isoelectric focusing was done, the gel strips were taken out of the isoelectric focusing system, immersed in an equilibration buffer containing a reducing agent, and shaken at room temperature for 15 minutes. The constituents of the equilibration buffer containing the reducing agent are as mentioned below.

100 mM Tris-HCl (pH 8.0)
6M urea
30% (v/v) glycerol
2% (w/v) SDS
1% (w/v) DTT

Next, the equilibration buffer containing the reducing agent was removed, and then the gel strips were immersed in an equilibration buffer containing an alkylating agent and shaken at room temperature for 15 minutes to obtain SDS-equilibrated gels. The constituents of the equilibration buffer containing the alkylating agent are as mentioned below.

100 mM Tris-HCl (pH 8.0)
6M urea
30% (v/v) glycerol
2% (w/v) SDS
2.5% (w/v) iodoacetamide Second-Dimensional SDS-PAGE In this example, the XCell SureLock Mini-Cell electrophoresis system produced by Life Technologies was used. The second-dimensional electrophoresis gels used were NuPAGE 4-12% Bis-Tris Gels produced by Life Technologies. Also, an electrophoresis buffer composed of the following constituents was prepared and used.

50 mM MOPS
50 mM Tris base
0.1% (w/v) SDS
1 mM EDTA

Further, an agarose solution for gel adhesion was used in this example, which was prepared by dissolving 0.5% (w/v) Agarose S (produced by Nippon Gene Co., Ltd.) and a moderate amount of BPB (bromophenol blue) in the electrophoresis buffer.

SDS-PAGE wells were washed well with the electrophoresis buffer, and then the buffer used for the washing was removed. Next, the washed wells were charged with the fully dissolved agarose solution for gel adhesion. Next, the SDS-equilibrated gel strips were immersed in agarose and closely adhered to second-dimensional electrophoresis gels using tweezers. After it was confirmed that agarose was fully fixed with the gels being closely adhered to each other, electrophoresis was performed at a constant voltage of 200 V for about 45 minutes.

Fluorescent Staining of Gels

The gels were fluorescently stained with SYPRO Ruby (produced by Life Technologies).

First, an airtight container to be used was washed well in advance with 98% (v/v) ethanol. The electrophoresed second-dimensional electrophoresis gel strips were taken out of the SDS-PAGE system, placed onto the washed airtight container, and treated twice by immersion in 50% (v/v) methanol and 7% (v/v) aqueous solution containing acetic acid for 30 minutes. Then, a further immersion treatment was done for 10 minutes, with the solution being replaced by water. Next, the second-dimensional electrophoresis gel strips were immersed in 40 mL of SYPRO Ruby and shaken at room temperature overnight. Thereafter, the SYPRO Ruby was removed, and then the second-dimensional electrophoresis gel strips were washed with water and shaken in 10% (v/v) methanol and 7% (v/v) aqueous solution containing acetic acid for 30 minutes. Further shaking was done for at least 30 minutes, with the solution being replaced by water.

Analysis

Figure 1:
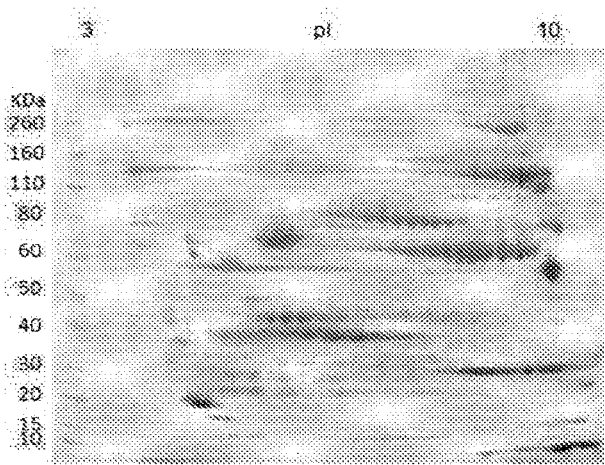
FIG. 1 is a photograph of a gel showing a protein electrophoretic pattern in two-dimensional electrophoresis of proteins contained in egg yolk of a chicken egg (raw egg). The bands at the left of the photograph are bands of molecular weight markers. The numbers on the left side of the photograph are molecular weights of respective molecular weight markers (KDa). The numbers on the upper side of the photograph indicate isoelectric points.

The second-dimensional electrophoresis gels obtained through the foregoing series of treatments were subjected to fluorescent image scanning on Typhoon 9400 (produced by GE). FIG. 1 illustrates the result of two-dimensional electrophoresis of proteins contained in the egg yolk (the result of the egg white is not illustrated). Molecular weight marker bands are found at the left of the photograph of the gel. The positions of the bands indicate particular molecular weights (KDa).

Example 2: Identification of Antigens by Immunoblotting (1)

Identification of antigens by immunoblotting was carried out by taking all the steps up to the step of "Second-dimensional SDS-PAGE" as described above in Example 1, followed by the steps of "Transfer to membrane", "Immunoblotting" and "Analysis" as described below.

Transfer to Membrane

Transfer to membrane was done using the following transfer system and transfer buffer.

Transfer system: XCell SureLock Mini-Cell and XCell II Blot Module (produced by Life Technologies)

Transfer buffer: NuPAGE Transfer Buffer (X20) (produced by Life Technologies), used in a form diluted 20-fold with milliQ water.

To be specific, proteins in the two-dimensional electrophoresis gels were transferred to a membrane (PVDF membrane) according to the following procedure.

(1) The PVDF membrane was immersed in 100% methanol followed by milliQ water, and then moved into the transfer buffer to hydrophilize the PVDF membrane.

(2) After sponge, filter paper, the gels treated by second-dimensional SDS-PAGE, the hydrophilized PVDF membrane, filter paper, and sponge were put in place in this order, the transfer system was energized at a constant voltage of 30 V for one hour.

Immunoblotting

Immunoblotting of the membrane was carried out using, as a primary antibody, the serum from a patient with an egg allergy (patient 1) or the serum from a non-egg-allergic subject. This egg-allergic patient is a patient diagnosed as food-dependent exercise-induced anaphylaxis (FDEIA) by chicken egg. This patient was negative for raw egg, boiled egg, and soft-boiled egg in a prick test and also negative for egg white, egg yolk, and ovomucoid in an allergen-specific IgE antibody test.

Immunoblotting of the membrane was carried out according to the following procedure.

(1) The transferred membrane was shaken in a 5% skim milk/PBST solution (a PBS buffer containing 0.1% Tween 20 nonionic surfactant) at room temperature for one hour.

(2) The membrane was left to stand in a solution of 5% primary antibody serum in 5% skim milk/PBST at room temperature for one hour.

(3) The membrane was washed with a PBST solution (5 min.×3 times).

(4) The membrane was left to stand in a 1:5000 dilution of the secondary antibody, anti-human IgE-HRP (horseradish peroxidase), with a 5% skim milk/PBST solution at room temperature for one hour.

(5) The membrane was washed with a PBST solution (5 min.×3 times).

(6) The membrane was left to stand in Pierce Western Blotting Substrate Plus (produced by Thermo Fisher Scientific) for 5 minutes.

Analysis

The membrane obtained through the foregoing series of treatments was subjected to fluorescent image scanning on Typhoon 9500 (produced by GE).

Figure 2:
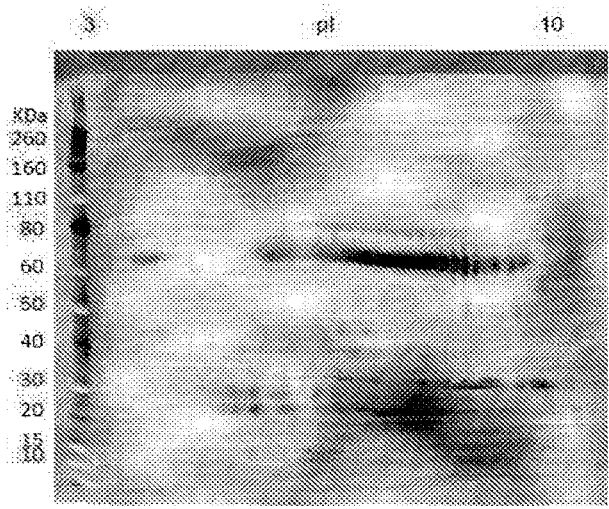
FIG. 2 is a photograph of an immunoblot of a two-dimensional electrophoretic pattern of proteins contained in egg yolk of a chicken egg (raw egg) stained using serum of Egg-allergic patient 1.

The immunoblot obtained with the serum from the egg-allergic patient was compared with that obtained with the control serum from the non-egg-allergic subject. Three spots that are different from those with the serum of the non-egg-allergic patient and different from the known chicken egg allergen proteins were detected on an immunoblot of the proteins contained in raw egg yolk with the serum of the egg-allergic patient (FIG. 2).

The molecular weights and isoelectric points of the three spots are as follows (FIG. 3).

Spot 1: Molecular weight 20 to 40 kDa, pI 4.0 to 10.0
Spot 2: Molecular weight 30 to 60 kDa, pI 5.0 to 10.0
Spot 3: Molecular weight 35 to 60 kDa, pI 5.0 to 10.0

Example 3: Mass Spectrometry and Identification of Antigens (1)

The amino acid sequences of the antigens that form the three protein spots of Example 2 were identified by mass spectroscopy.

To be specific, protein extraction and mass spectroscopy were done by the following procedure.

(1) Egg yolk of raw chicken egg was subjected to protein extraction, two-dimensional electrophoresis and transfer to membrane by following the procedures described in Examples 1 and 2, and the resulting membrane was stained by shaking in a solution of 0.008% Direct blue in 40% ethanol and 10% acetic acid.

(2) Then, the membrane was decolorized by repeating a 5-minute treatment with 40% ethanol and 10% acetic acid three times, washed with water for 5 minutes, and then dried by air.

(3) A protein spot of interest was cut out with a clean cutter blade and put into a centrifugal tube. The cut membrane was subjected to hydrophilization with 50 μL of methanol, followed by washing with 100 μL of water twice and then centrifugal cleaning. Thereafter, 20 μL of 20 mM NH₄HCO₃ and 50% acetonitrile were added.

(4) 1 μL of 1 pmol/μL lysyl endopeptidase (produced by WAKO) was added, and the solution was left to stand at 37° C. for 60 minutes and then collected in a new centrifugal tube. After 20 μL of 20 mM NH₄HCO₃ and 70% acetonitrile were added to the membrane, the membrane was immersed therein at room temperature for 10 minutes, and the resulting solution was further collected. The solution was dissolved with 0.1% formic acid and 10 μL of 4% acetonitrile and transferred to a tube.

(5) The collected solution was dried under reduced pressure, dissolved with 15 μL of solution A (a 0.1% formic acid/4% acetonitrile solution), and analyzed by mass spectroscopy (ESI-TOF6600, produced by AB Sciex).

(6) Identification of proteins based on the MS data obtained with the mass spectrometer was done by searching the NCBI or Uniprot database.

Results

The mass spectrometry of the spots resulted in the detection of the following amino acid sequences.

Spot 1: The amino acid sequences set forth in SEQ ID NOs: 3 to 11

Spot 2: The amino acid sequences set forth in SEQ ID NOs: 9 to 11, 14, 16

Spot 3: The amino acid sequences set forth in SEQ ID NOs: 19 to 45

Furthermore, the spots were identified as the following proteins by the analysis of the mass data obtained from the mass spectrometer for spots 1 and 2 at NCBI and for spot 3 with UniProt.

Spot 1: A C-terminal portion (amino acid sequence: SEQ ID NO: 2, encoding nucleotide sequence: SEQ ID NO: 1) of Vitellogenin-3 (amino acid sequence: NCBI accession number XP_015146355, encoding nucleotide sequence: GenBank accession number XM_015290869.1):

Spot 2: A C-terminal portion (amino acid sequence: SEQ ID NO: 13, encoding nucleotide sequence: SEQ ID NO: 12) of Vitellogenin-3 (amino acid sequence: NCBI accession number XP_015146355, encoding nucleotide sequence: GenBank accession number XM_015290869.1)

Spot 3: A middle portion of Vitellogenin-1 (amino acid sequence: UniProt accession number P87498, encoding nucleotide sequence: ENA(EMBL) accession number D89547.1) or a C-terminal portion of Lipovitelin-1 (amino acid sequence: SEQ ID NO: 18, encoding nucleotide sequence: SEQ ID NO: 17)

Example 4: Identification of Antigens by Immunoblotting (2)

The Identification of antigens was performed by immunoblotting using the serum of three different egg-allergic patients (Patient 2, Patient 3, Patient 4), in the same manner as in Example 2. Spots that are different from those with the serum of the non-egg-allergic patient and different from the known chicken egg allergen proteins were detected on immunoblots of the proteins contained in raw egg yolk with the serums of the egg-allergic patients (FIG. 4 for Patient 2, FIG. 5 for Patient 3, FIG. 6 for Patient 4). Specifically, Spots 4 to 8, Spots 9 and 10, and Spot 11 were respectively detected for patient 2, Patient 3, and Patient 4.

The molecular weights and isoelectric points of Spots 4 to 11 are as follows (FIGS. 4 to 6).

Spot 4: Molecular weight 20 to 50 kDa, pI 3.0 to 8.0

Spots 5, 6: Molecular weight 80 to 260 kDa, pI 1.0 to 8.0

Spot 7: Molecular weight 110 to 300 kDa, pI 3.0 to 8.0

Spot 8: Molecular weight 160 to 550 kDa, pI 3.0 to 8.0

Spot 9: Molecular weight 20 to 50 kDa, pI 7.0 to 11.0

Spot 10: Molecular weight 20 to 50 kDa, pI 7.0 to 11.0

Spot 11: Molecular weight 15 to 40 kDa, pI 6.0 to 11.0

Example 5: Mass Spectrometry and Identification of Antigens (2)

The identification of the amino acid sequences of antigens producing spots 4 to 11 in Example 4 by the mass spectrometry was performed in the same manner as in Example 3.

The mass spectrometry of the spots resulted in the detection of the following amino acid sequences.

Spot 4: The amino acid sequences set forth in SEQ ID NOs: 48 to 57

Spots 5, 6: The amino acid sequences set forth in SEQ ID NOs: 60 to 104

Spot 7: The amino acid sequences set forth in SEQ ID NOs: 107 to 150

Spot 8: The amino acid sequences set forth in SEQ ID NOs: 153 to 235

Spot 9: The amino acid sequences set forth in SEQ ID NOs: 238 to 249

Spot 10: The amino acid sequences set forth in SEQ ID NOs: 252 to 260

Spot 11: The amino acid sequences set forth in SEQ ID NOs: 263 to 271

Furthermore, the spots were identified as the following proteins by the analysis of the mass data obtained from the mass spectrometer for the spots at NCBI.

Spot 4: Vitellogenin-3 (amino acid sequence: NCBI accession number XP_015146355, encoding nucleotide sequence: GenBank accession number XM_015290869.1) (amino acid sequence: SEQ ID NO: 47, encoding nucleotide sequence: SEQ ID NO: 46).

Spots 5, 6: A Vitellogenin-2 precursor (amino acid sequence: NCBI accession number NP_001026447.1, encoding nucleotide sequence: GenBank accession number NM_001031276.1) (amino acid sequence: SEQ ID NO: 59, encoding nucleotide sequence: SEQ ID NO: 58).

Spot 7: A Vitellogenin-2 precursor (amino acid sequence: NCBI accession number NP_001026447.1, encoding nucleotide sequence: GenBank accession number NM_001031276.1) (amino acid sequence: SEQ ID NO: 106, encoding nucleotide sequence: SEQ ID NO: 105)

Spot 8: An Apolipoprotein B precursor (amino acid sequence: NCBI accession number NP_001038098.1, encoding nucleotide sequence: GenBank accession number NM_001044633.1) (amino acid sequence: SEQ ID NO: 152, encoding nucleotide sequence: SEQ ID NO: 151)

Spot 9: An Apolipoprotein B precursor (amino acid sequence: NCBI accession number NP_001038098.1, encoding nucleotide sequence: GenBank accession number NM_001044633.1) (amino acid sequence: SEQ ID NO: 237, encoding nucleotide sequence: SEQ ID NO: 236).

Spot 10: An Apolipoprotein B precursor (amino acid sequence: NCBI accession number NP_001038098.1, encoding nucleotide sequence: GenBank accession number NM_001044633.1) (amino acid sequence: SEQ ID NO: 251, encoding nucleotide sequence: SEQ ID NO: 250)

Spot 11: A Vitellogenin-2 precursor (amino acid
   sequence: NCBI accession number NP_001026447.1,
   encoding nucleotide sequence: GenBank accession
   number NM_001031276.1) (amino acid sequence:
   SEQ ID NO: 262, encoding nucleotide sequence: SEQ
   ID NO: 261).

INDUSTRIAL APPLICABILITY

The present invention can provide a novel antigen of an
egg allergy, a method for diagnosing an egg allergy and a kit for diagnosing an egg allergy, a pharmaceutical composition
comprising the antigen, an egg, a processed product of an
egg, or a bird which lays or has hatched from the egg in
which the antigen is eliminated or reduced, and a method for
producing a processed product of an egg in which the
antigen is eliminated or reduced. The present invention can
further provide testers for determining the presence or
absence of an egg antigen in an object of interest.

SEQUENCE LISTING

```
Sequence total quantity: 271
SEQ ID NO: 1             moltype = DNA  length = 831
FEATURE                  Location/Qualifiers
source                   1..831
                         mol_type = other DNA
                         organism = Gallus gallus
SEQUENCE: 1
tcaatcattg aaaaccttaa agctcgttgt tcagtttcac aaaatatgat aacaaccttc  60
aatggagttg agtttaacta ttcaatgcct gcaaattgct accacatctt ggcacaggat 120
tgtagtccag aactgaagtt cctggtaatg atgaaaagac ttggagaatc tgctgatctc 180
acagcaataa gtgtcagact tgccagccat gaggttgaca tgtatgtttc caatggacta 240
atccagctga agattaatgg tgttcaaacc ccaacgacg ttccatacac atctaagtct 300
ggtctgctga taagcagtga gaaggaaggt ttgtcattaa aagcccctga atatggtgta 360
gaaaaactat attacgatag acgtaaactt gagattcgag ttgctttctg gatggttgga 420
aaaacatgtg gtatttgtgg aaaatatgat gctgagaaga aaagggagta tcaaatgccc 480
agtggatatt tagctaaaga tgcagtgagt tttgctcagt cctgggtcat ctcagaagac 540
acgtgtactg gagcttgcaa gctgcagagg aaatttgtca aaattgagaa gccggttgca 600
tttaacaaaa aggcctcaaa atgctttttcc attgagccag ttttacgctg tgcagaaggc 660
tgttcagcaa ccaggactgt tcctgtctct gtgggtttcc actgtgtccc atctgactcc 720
acactcgagc tggaggaaga gcaggtgagg ttagaccaga agtctgagga cttggtgagc 780
agggtcgatg cccatacggc gtgttcctgc gcccagcagc tgtgctcagc g           831

SEQ ID NO: 2             moltype = AA  length = 277
FEATURE                  Location/Qualifiers
source                   1..277
                         mol_type = protein
                         organism = Gallus gallus
SEQUENCE: 2
SIIENLKARC SVSQNMITTF NGVEFNYSMP ANCYHILAQD CSPELKFLVM MKRLGESADL  60
TAISVRLASH EVDMYVSNGL IQLKINGVQT PTDVPYTSKS GLLISSEKEG LSLKAPEYGV 120
EKLYYDRRKL EIRVAFWMVG KTCGICGKYD AEKKREYQMP SGYLAKDAVS FAQSWVISED 180
TCTGACKLQR KFVKIEKPVA FNKKASKCFS IEPVLRCAEG CSATRTVPVS VGFHCVPSDS 240
TLELEEEQVR LDQKSEDLVS RVDAHTACSC AQQLCSA                          277

SEQ ID NO: 3             moltype = AA  length = 8
FEATURE                  Location/Qualifiers
source                   1..8
                         mol_type = protein
                         organism = Gallus gallus
SEQUENCE: 3
APEYGVEK                                                            8

SEQ ID NO: 4             moltype = AA  length = 13
FEATURE                  Location/Qualifiers
source                   1..13
                         mol_type = protein
                         organism = Gallus gallus
SEQUENCE: 4
GVQTPTDVPY TSK                                                     13

SEQ ID NO: 5             moltype = AA  length = 8
FEATURE                  Location/Qualifiers
source                   1..8
                         mol_type = protein
                         organism = Gallus gallus
SEQUENCE: 5
IEKPVAFN                                                            8

SEQ ID NO: 6             moltype = AA  length = 5
FEATURE                  Location/Qualifiers
source                   1..5
```

-continued

```
                             mol_type = protein
                             organism = Gallus gallus
SEQUENCE: 6
PVAFN                                                                   5

SEQ ID NO: 7             moltype = AA   length = 6
FEATURE                  Location/Qualifiers
source                   1..6
                         mol_type = protein
                         organism = Gallus gallus
SEQUENCE: 7
SIIENL                                                                  6

SEQ ID NO: 8             moltype = AA   length = 9
FEATURE                  Location/Qualifiers
source                   1..9
                         mol_type = protein
                         organism = Gallus gallus
SEQUENCE: 8
IEKPVAFNK                                                               9

SEQ ID NO: 9             moltype = AA   length = 15
FEATURE                  Location/Qualifiers
source                   1..15
                         mol_type = protein
                         organism = Gallus gallus
SEQUENCE: 9
INGVQTPTDV PYTSK                                                        15

SEQ ID NO: 10            moltype = AA   length = 13
FEATURE                  Location/Qualifiers
source                   1..13
                         mol_type = protein
                         organism = Gallus gallus
SEQUENCE: 10
LGESADLTAI SVR                                                          13

SEQ ID NO: 11            moltype = AA   length = 14
FEATURE                  Location/Qualifiers
source                   1..14
                         mol_type = protein
                         organism = Gallus gallus
SEQUENCE: 11
RLGESADLTA ISVR                                                         14

SEQ ID NO: 12            moltype = DNA   length = 1314
FEATURE                  Location/Qualifiers
source                   1..1314
                         mol_type = other DNA
                         organism = Gallus gallus
SEQUENCE: 12
gtgcaggtgt ttgtttcaag catcacagaa tcagataggt ggaaactctg tgctgatgct    60
tcagtagtaa attcccataa agcatcgggt acccttaaat ggggtaaaga ttgccaggac   120
tatcaggttg ctactcagat tgcaacaggg caatttgctg cacacccggc tatacaggtg   180
aagctggagt ggtcagaagt gccttcaagt gtccgaaaaa ctgccagatg gttctacaca   240
tatcttccag gagctgcgta tatgcttggc tactcccaga agcagcagcg tggtccttct   300
caccaggcag ccatggtgat ggctctgacg tctccaagaa cctgcgatgt ggtcctgaag   360
ctacctgagc tcacagttta caacagagcc atcaggcttc ccctgccact cccttcaagt   420
tcagatacac caacctcaac actaccatcc tccaaatgga acgtctttta ccaagcagcc   480
ttttcaatca ttgaaaacct taaagctcgt tgttcagttt cacaaaatat gataacaacc   540
ttcaatggag ttgagtttaa ctattcaatg cctgcaaatt gctaccacat cttggcacag   600
gattgtagtc cagaactgaa gttcctggta atgatgaaaa gacttggaga atctgctgat   660
ctcacagcaa taagtgtcag acttgccagc catgaggttg acatgtatgt ttccaatgga   720
ctaatccagc tgaagattaa tggtgttcaa accccaacag acgttccata cacatctaag   780
tctggtctgc tgataagcag tgagaaggaa ggtttgtcat taaaagcccc tgaatatggt   840
gtagaaaaac tatattacga tagacgtaaa cttgagattc gggttgcttt ctggatggtt   900
ggaaaaacat gtggtatttg tggaaaatat gatgctgaga agaaaaggga gtatcaaatg   960
cccagtggat atttagctaa agatgcagtg agttttgctc agtcctgggt catctcagaa  1020
gacacgtgta ctggagcttg caagctgcag aggaaatttg tcaaaattga gaagccggtt  1080
gcatttaaca aaaaggcctc aaaatgcttt tccattgagc cagttttacg ctgtgcagaa  1140
ggctgttcag caaccaggac tgttcctgtc tctgtgggtt tccactgtgt cccatctgac  1200
tccacactcg agctggagga agagcaggtg aggttagacc agaagtctga ggacttggtg  1260
agcagggtca tgcccatac ggcgtgttcc tgcgcccagc agctgtgctc agcg          1314

SEQ ID NO: 13            moltype = AA   length = 438
FEATURE                  Location/Qualifiers
source                   1..438
                         mol_type = protein
                         organism = Gallus gallus
```

```
SEQUENCE: 13
VQVFVSSITE SDRWKLCADA SVVNSHKASG TLKWGKDCQD YQVATQIATG QFAAHPAIQV   60
KLEWSEVPSS VRKTARWFYT YLPGAAYMLG YSQKQQRGPS HQAAMVMALT SPRTCDVVLK  120
LPELTVYNRA IRLPLPLPSS SDTPTSTLPS SKWNVFYQAA FSIIENLKAR CSVSQNMITT  180
FNGVEFNYSM PANCYHILAQ DCSPELKFLV MMKRLGESAD LTAISVRLAS HEVDMYVSNG  240
LIQLKINGVQ TPTDVPYTSK SGLLISSEKE GLSLKAPEYG VEKLYYDRRK LEIRVAFWMV  300
GKTCGICGKY DAEKKREYQM PSGYLAKDAV SFAQSWVISE DTCTGACKLQ RKFVKIEKPV  360
AFNKKASKCF SIEPVLRCAE GCSATRTVPV SVGFHCVPSD STLELEEEQV RLDQKSEDLV  420
SRVDAHTACS CAQQLCSA                                               438

SEQ ID NO: 14            moltype = AA   length = 9
FEATURE                  Location/Qualifiers
source                   1..9
                         mol_type = protein
                         organism = Gallus gallus
SEQUENCE: 14
LPELTVYNR                                                          9

SEQ ID NO: 15            moltype = AA   length = 13
FEATURE                  Location/Qualifiers
source                   1..13
                         mol_type = protein
                         organism = Gallus gallus
SEQUENCE: 15
LGESADLTAI SVR                                                    13

SEQ ID NO: 16            moltype = AA   length = 13
FEATURE                  Location/Qualifiers
source                   1..13
                         mol_type = protein
                         organism = Gallus gallus
SEQUENCE: 16
VQVFVSSITE SDR                                                    13

SEQ ID NO: 17            moltype = DNA   length = 996
FEATURE                  Location/Qualifiers
source                   1..996
                         mol_type = other DNA
                         organism = Gallus gallus
SEQUENCE: 17
gacaaacctt ttgcatcagg ttacttgaag atgtttggcc aggagttgct ctttggtaga   60
ctcgataaag acaccctcca aaatgtattg caggtatggt atggacctga tgaaaaaatc  120
ccttcaataa ggagattaat cagtagcctt caaactggca taggaagaca atggactaag  180
gctttactat tgtctgagat tcgttgtatt gtgcctacct gtgttgggtt cccgatggag  240
accagcttct attactcttc tgtcacaaaa gtggcaggaa acgttcaagc gcaaattaca  300
ccttcaccga ggtctgattt cagattgact gagttactaa attccaacgt taggctgcga  360
tccaaaatga gtctaagcat ggctaaacat atgacctttg taattgggat caacacaaac  420
atgatccagg cagggctgga agcacacacc aaagtaaatg ctcatgtacc tgtgaatgtt  480
gttgccacta ttcaaatgaa ggaaaaaagt atcaaagctg aaattccacc atgcaaagaa  540
gagactaact taattattgt aagctctaag acatttgctg ttcacgaaa tattgaagat  600
ttggctgcta gtaagatgac tccagttctt ctacctgaag cagtgcctga cataatgaag  660
atgtccttcg actcagattc tgcatcaggc gagactgata acatcaggga cagacagtct  720
gtagaagatg tttcgtctgg aaattccttc tcctttggac atccttcttc cgggaaggag  780
ccatttattc agtccatgtg ctccaacgca agtacatttg gggttcaagt gtgcattgag  840
aagaaaagtg tacatgcagc attcatcaga aatgtgcctc tttataacgc tattggaaaa  900
catgccctta gaatgagctt caagccagtc tactcagatg tacctattga aaaaatacaa  960
gtcacaattc aagcaggaga tcaagctcct acaaaa                           996

SEQ ID NO: 18            moltype = AA   length = 332
FEATURE                  Location/Qualifiers
source                   1..332
                         mol_type = protein
                         organism = Gallus gallus
SEQUENCE: 18
DKPFASGYLK MFGQELLFGR LDKDTLQNVL QVWYGPDEKI PSIRRLISSL QTGIGRQWTK   60
ALLLSEIRCI VPTCVGFPME TSFYYSSVTK VAGNVQAQIT PSPRSDFRLT ELLNSNVRLR  120
SKMSLSMAKH MTFVIGINTN MIQAGLEAHT KVNAHVPVNV VATIQMKEKS IKAEIPPCKE  180
ETNLIIVSSK TFAVTRNIED LAASKMTPVL LPEAVPDIMK MSFDSDSASG ETDNIRDRQS  240
VEDVSSGNSF SFGHPSSGKE PFIQSMCSNA STFGVQVCIE KKSVHAAFIR NVPLYNAIGE  300
HALRMSFKPV YSDVPIEKIQ VTIQAGDQAP TK                               332

SEQ ID NO: 19            moltype = AA   length = 13
FEATURE                  Location/Qualifiers
source                   1..13
                         mol_type = protein
                         organism = Gallus gallus
SEQUENCE: 19
AGNVQAQITP SPR                                                    13
```

-continued

```
SEQ ID NO: 20           moltype = AA   length = 8
FEATURE                 Location/Qualifiers
source                  1..8
                        mol_type = protein
                        organism = Gallus gallus
SEQUENCE: 20
ALLLSEIR                                                                8

SEQ ID NO: 21           moltype = AA   length = 8
FEATURE                 Location/Qualifiers
source                  1..8
                        mol_type = protein
                        organism = Gallus gallus
SEQUENCE: 21
DKPFASGY                                                                8

SEQ ID NO: 22           moltype = AA   length = 10
FEATURE                 Location/Qualifiers
source                  1..10
                        mol_type = protein
                        organism = Gallus gallus
SEQUENCE: 22
DKPFASGYLK                                                              10

SEQ ID NO: 23           moltype = AA   length = 16
FEATURE                 Location/Qualifiers
source                  1..16
                        mol_type = protein
                        organism = Gallus gallus
SEQUENCE: 23
DTLQNVLQVW YGPDEK                                                       16

SEQ ID NO: 24           moltype = AA   length = 11
FEATURE                 Location/Qualifiers
source                  1..11
                        mol_type = protein
                        organism = Gallus gallus
SEQUENCE: 24
EETNLIIVSS K                                                            11

SEQ ID NO: 25           moltype = AA   length = 12
FEATURE                 Location/Qualifiers
source                  1..12
                        mol_type = protein
                        organism = Gallus gallus
SEQUENCE: 25
GNVQAQITPS PR                                                           12

SEQ ID NO: 26           moltype = AA   length = 10
FEATURE                 Location/Qualifiers
source                  1..10
                        mol_type = protein
                        organism = Gallus gallus
SEQUENCE: 26
IQAGDQAPTK                                                              10

SEQ ID NO: 27           moltype = AA   length = 13
FEATURE                 Location/Qualifiers
source                  1..13
                        mol_type = protein
                        organism = Gallus gallus
SEQUENCE: 27
IQVTIQAGDQ APT                                                          13

SEQ ID NO: 28           moltype = AA   length = 14
FEATURE                 Location/Qualifiers
source                  1..14
                        mol_type = protein
                        organism = Gallus gallus
SEQUENCE: 28
IQVTIQAGDQ APTK                                                         14

SEQ ID NO: 29           moltype = AA   length = 20
FEATURE                 Location/Qualifiers
source                  1..20
                        mol_type = protein
                        organism = Gallus gallus
SEQUENCE: 29
ITPSPRSDFR LTELLNSNVR                                                   20
```

-continued

```
SEQ ID NO: 30              moltype = AA   length = 12
FEATURE                    Location/Qualifiers
source                     1..12
                           mol_type = protein
                           organism = Gallus gallus SEQUENCE: 30
KEETNLIIVS SK                                                          12

SEQ ID NO: 31              moltype = AA   length = 11
FEATURE                    Location/Qualifiers
source                     1..11
                           mol_type = protein
                           organism = Gallus gallus SEQUENCE: 31
KPVYSDVPIE K                                                           11

SEQ ID NO: 32              moltype = AA   length = 8
FEATURE                    Location/Qualifiers
source                     1..8
                           mol_type = protein
                           organism = Gallus gallus SEQUENCE: 32
LDKDTLQN                                                               8

SEQ ID NO: 33              moltype = AA   length = 11
FEATURE                    Location/Qualifiers
source                     1..11
                           mol_type = protein
                           organism = Gallus gallus SEQUENCE: 33
LDKDTLQNVL Q                                                           11

SEQ ID NO: 34              moltype = AA   length = 19
FEATURE                    Location/Qualifiers
source                     1..19
                           mol_type = protein
                           organism = Gallus gallus SEQUENCE: 34
LDKDTLQNVL QVWYGPDEK                                                   19

SEQ ID NO: 35              moltype = AA   length = 11
FEATURE                    Location/Qualifiers
source                     1..11
                           mol_type = protein
                           organism = Gallus gallus SEQUENCE: 35
LISSLQTGIG R                                                           11

SEQ ID NO: 36              moltype = AA   length = 8
FEATURE                    Location/Qualifiers
source                     1..8
                           mol_type = protein
                           organism = Gallus gallus SEQUENCE: 36
LTELLNSN                                                               8

SEQ ID NO: 37              moltype = AA   length = 10
FEATURE                    Location/Qualifiers
source                     1..10
                           mol_type = protein
                           organism = Gallus gallus SEQUENCE: 37
LTELLNSNVR                                                             10

SEQ ID NO: 38              moltype = AA   length = 9
FEATURE                    Location/Qualifiers
source                     1..9
                           mol_type = protein
                           organism = Gallus gallus SEQUENCE: 38
NIEDLAASK                                                              9

SEQ ID NO: 39              moltype = AA   length = 14
FEATURE                    Location/Qualifiers
source                     1..14
                           mol_type = protein
                           organism = Gallus gallus

SEQUENCE: 39
```

NVPLYNAIGE HALR                                                                14

```
SEQ ID NO: 40          moltype = AA  length = 11
FEATURE                Location/Qualifiers
source                 1..11
                       mol_type = protein
                       organism = Gallus gallus
SEQUENCE: 40
NVQAQITPSP R                                                                   11

SEQ ID NO: 41          moltype = AA  length = 8
FEATURE                Location/Qualifiers
source                 1..8
                       mol_type = protein
                       organism = Gallus gallus
SEQUENCE: 41
PSSGKEPF                                                                       8

SEQ ID NO: 42          moltype = AA  length = 10
FEATURE                Location/Qualifiers
source                 1..10
                       mol_type = protein
                       organism = Gallus gallus
SEQUENCE: 42
PVYSDVPIEK                                                                     10

SEQ ID NO: 43          moltype = AA  length = 12
FEATURE                Location/Qualifiers
source                 1..12
                       mol_type = protein
                       organism = Gallus gallus
SEQUENCE: 43
RLISSLQTGI GR                                                                  12

SEQ ID NO: 44          moltype = AA  length = 8
FEATURE                Location/Qualifiers
source                 1..8
                       mol_type = protein
                       organism = Gallus gallus
SEQUENCE: 44
SVHAAFIR                                                                       8

SEQ ID NO: 45          moltype = AA  length = 10
FEATURE                Location/Qualifiers
source                 1..10
                       mol_type = protein
                       organism = Gallus gallus
SEQUENCE: 45
VQAQITPSPR                                                                     10

SEQ ID NO: 46          moltype = DNA  length = 1023
FEATURE                Location/Qualifiers
source                 1..1023
                       mol_type = other DNA
                       organism = Gallus gallus
SEQUENCE: 46
ggtccttctc accaggcagc catggtgatg gctctgacgt ctccaagaac ctgcgatgtg  60
gtcctgaagc tacctgagct cacagtttac aacagagcca tcaggcttcc cctgccactc  120
ccttcaagtt cagatacacc aacctcaaca ctaccatcct ccaaatggaa cgtctttttac  180
caagcagcct tttcaatcat tgaaaacctt aaagctcgtt gttcagtttc acaaaatatg  240
ataacaacct tcaatggagt tgagtttaac tattcaatgc ctgcaaattg ctaccacatc  300
ttggcacagg attgtagtcc agaactgaag ttcctggtaa tgatgaaaag acttggagaa  360
tctgctgatc tcacagcaat aagtgtcaga cttgccagcc atgaggttga catgtatgtt  420
tccaatggac taatccagct gaagattaat ggtgttcaaa ccccaacaga cgttccatac  480
acatctaagt ctggtctgct gataagcagt gagaaggaag gtttgtcatt aaaagccct  540
gaatatggtg tagaaaaact atattacgat agacgtaaac ttgagattcg ggttgctttc  600
tggatggttg gaaaaacatg tggtatttgt ggaaaatatg atgctgagaa gaaaagggag  660
tatcaaatgc ccagtggata tttagctaaa gatgcagtga gttttgctca gtcctgggtc  720
atctcagaag acacgtgtac tggagcttgc aagctgcaga ggaaatttgt caaaattgag  780
aagccggttg catttaacaa aaaggcctca aaatgctttt ccattgagcc agttttacgc  840
tgtgcagaag ctgttcagc aaccaggact gttcctgtct ctgtgggttt ccactgtgtc  900
ccatctgact ccacactcga gctggaggaa gagcaggtga ggttagacca gaagtctgag  960
gacttggtga gcagggtcga tgcccatacg gcgtgttcct gcgcccagca gctgtgctca  1020
gcg                                                                  1023

SEQ ID NO: 47          moltype = AA  length = 341
FEATURE                Location/Qualifiers
source                 1..341
                       mol_type = protein
```

-continued

```
                         organism = Gallus gallus
SEQUENCE: 47
GPSHQAAMVM ALTSPRTCDV VLKLPELTVY NRAIRLPLPL PSSSDTPTST LPSSKWNVFY    60
QAAFSIIENL KARCSVSQNM ITTFNGVEFN YSMPANCYHI LAQDCSPELK FLVMMKRLGE   120
SADLTAISVR LASHEVDMYV SNGLIQLKIN GVQTPTDVPY TSKSGLLISS EKEGLSLKAP   180
EYGVEKLYYD RRKLEIRVAF WMVGKTCGIC GKYDAEKKRE YQMPSGYLAK DAVSFAQSWV   240
ISEDTCTGAC KLQRKFVKIE KPVAFNKKAS KCFSIEPVLR CAEGCSATRT VPVSVGFHCV   300
PSDSTLELEE EQVRLDQKSE DLVSRVDAHT ACSCAQQLCS A                       341

SEQ ID NO: 48           moltype = AA  length = 8
FEATURE                 Location/Qualifiers
source                  1..8
                        mol_type = protein
                        organism = Gallus gallus
SEQUENCE: 48
APEYGVEK                                                              8

SEQ ID NO: 49           moltype = AA  length = 7
FEATURE                 Location/Qualifiers
source                  1..7
                        mol_type = protein
                        organism = Gallus gallus
SEQUENCE: 49
IEKPVAF                                                               7

SEQ ID NO: 50           moltype = AA  length = 15
FEATURE                 Location/Qualifiers
source                  1..15
                        mol_type = protein
                        organism = Gallus gallus
SEQUENCE: 50
INGVQTPTDV PYTSK                                                     15

SEQ ID NO: 51           moltype = AA  length = 13
FEATURE                 Location/Qualifiers
source                  1..13
                        mol_type = protein
                        organism = Gallus gallus
SEQUENCE: 51
LGESADLTAI SVR                                                       13

SEQ ID NO: 52           moltype = AA  length = 9
FEATURE                 Location/Qualifiers
source                  1..9
                        mol_type = protein
                        organism = Gallus gallus
SEQUENCE: 52
LPELTVYNR                                                            9

SEQ ID NO: 53           moltype = AA  length = 16
FEATURE                 Location/Qualifiers
source                  1..16
                        mol_type = protein
                        organism = Gallus gallus
SEQUENCE: 53
LPLPLPSSSD TPTSTL                                                    16

SEQ ID NO: 54           moltype = AA  length = 12
FEATURE                 Location/Qualifiers
source                  1..12
                        mol_type = protein
                        organism = Gallus gallus
SEQUENCE: 54
PSDSTLELEE EQ                                                        12

SEQ ID NO: 55           moltype = AA  length = 9
FEATURE                 Location/Qualifiers
source                  1..9
                        mol_type = protein
                        organism = Gallus gallus
SEQUENCE: 55
SGLLISSEK                                                            9

SEQ ID NO: 56           moltype = AA  length = 7
FEATURE                 Location/Qualifiers
source                  1..7
                        mol_type = protein
                        organism = Gallus gallus
SEQUENCE: 56
```

```
SIEPVLR                                                              7

SEQ ID NO: 57        moltype = AA   length = 9
FEATURE              Location/Qualifiers
source               1..9
                     mol_type = protein
                     organism = Gallus gallus
SEQUENCE: 57
TVPVSVGFH                                                            9

SEQ ID NO: 58        moltype = DNA   length = 3363
FEATURE              Location/Qualifiers
source               1..3363
                     mol_type = other DNA
                     organism = Gallus gallus
SEQUENCE: 58
atgagggggga tcatactggc attagtgctc acccttgtag gcagccagaa gtttgacatt   60
gacccaggat tcaatagcag aaggagttac ctgtacaact atgaaggttc tatgttgaat  120
gggcttcaag acagaagttt gggcaaagct ggtgtgcgct tgagcagcaa gctagagatc  180
agtgggctac cagagaatgc ttacctcctc aaggtccgct ctccacaagt ggaggagtac  240
aatggggtct ggcccaggga tcccttcact cgatcttcca aaatcaccca agtgatctca  300
tcgtgtttca cccggctctt caaatttgaa tacagcagtg gacggatcgg aaacatttat  360
gccccagaag actgcccaga tctgtgtgtt aacatagtga gaggaatatt gaacatgttc  420
cagatgacca ttaaaaaatc acagaacgtc tacgaattac aagaggctgg aattggaggt  480
atttgtcatg caaggtatgt cattcaggaa gacaggaaga atagccgaat ctatgttacc  540
agaactgtgg acttgaataa ttgccaggaa aaggtgcaaa aaagcattgg aatggcttac  600
atctatccct gccctgtgga cgtgatgaaa gaaaggctca ccaaagggac caccgctttc  660
tcctacaagc tgaagcagtc agacagcggc acgctgatca cagatgtctc gtcgcggcag  720
gtgtatcaga tctccccatt caatgagccc actggggtgg ctgtcatgga agcaagacag  780
cagctcactt tggtcgaggt gagaagtgag cggggcaggt ccccagatgt ccccatgcag  840
aactatggca gccttcgcta ccgcttccca gccgtactgc cacagatgcc acttcagctg  900
atcaagacaa aaaaccctga gcaacggata gtagaaacgc tgcagcacat agtcctgaat  960
aaccaacaag atttccatga cgatgtttca tacagattct tagaggtggt ccagctttgc 1020
cggatagcaa atgctgacaa tcttgagtct atctggagac aagtttcaga taaacctcgt 1080
tacaggcgat ggctcctgag cgcagtttct gcgagtggca ccacagaaac actaaaattc 1140
cttaagaaca gaattcgcaa tgatgacctc aactacattc agacccttct aactgtttct 1200
ttgactcttc atttattgca agctgatgaa cacacacttc caatagcagc agatttaatg 1260
accagctctg gaattcagaa aaatcctgtg cttcagcaag tggcctgctt gggatatagc 1320
tctgtagtca acagatactg ctctcagacc tcagcatgtc ctaaggaagc tcttcagccc 1380
atccatgacc tggcagatga agcaatcagc aggggccgtg aagacaaaat gaaattagct 1440
ctaaagtgca ttggtaacat gggagaacca gccagcttaa agcgcatcct gaagttcctt 1500
ccaatatctt catccagtgc tgctgatatc ccagtccaca ttcagataga tgccataacg 1560
gccttgaaaa agatagcttg gaaggacccc aaaacagtgc agggctatct catccagatc 1620
cttgcagacc aatcacttcc ccctgaggtg cgaatgatgg cttgtgctgt tatctttgag 1680
acaaggcctg cccttgcttt gataacgact atagctaacg tggcaatgaa ggagagcaat 1740
atgcaagtgg ccagttttgt atattcccac atgaagtctt tgtcaaagag cagattgcca 1800
tttatgtaca acatatcttc cgcttgtaac attgccctta agtcctgtc ccccaaactg 1860
gacagtatga gctatcggta cagcaaggtc attcgagcag acacttactt tgataactat 1920
agagttggtg ctactggaga aatctttgtt gtgaacagcc caagaactat gttcccatca 1980
gcaataattt ccaaattgat ggcaaattct gcaggttcag tggctgatct ggtagaggtt 2040
ggcatccgag tggaaggcct cgcagatgtc ataatgaaaa gaaacatccc atttgctgaa 2100
tatcccacat acaagcagat aaaggagctt ggaaaagctc tgcagggatg gaaagagctg 2160
ccgacagaaa cccctttggt atcagcctac ttgaaaatac ttggccaaga agtggccttc 2220
atcaacatca acaggaact cctgcaacag gtcatgaaga ctgtagtgga acctgctgat 2280
cgaaacgcag caataaagag aatcgccaac cagatccgca acagcattgc agggcagtgg 2340
acgcagccgg tgtggatggg agagctgcga tacgtggttc ccagctgtct cggcctgccg 2400
ctggagtacg ggtcctacac caccgccctg gcacgagctg cagtcagcgt tgagggaaag 2460
atgacgccgc ctttaaccgg agatttcaga cttttctcagt tgcttgaatc caccatgcag 2520
attcggtctg acttaaagcc cagtttatat gtgcatacag ttgcaacgat gggtgtcaac 2580
acagaatact ttcaacatgc tgttgaaatt caaggcgagg tccagacaag aatgccaatg 2640
aagtttgatg ccaagataga tgtgaaattg aaaaacctta agattgaaac gaacccatgc 2700
cgtgaggaaa ctgagatagt ggttggaaga cataaggctt ttgctgtatc aaggaacata 2760
ggagaactag gtgttgaaaa gaggacctca attctgccgg aagatgctcc attagatgtt 2820
acagaagaac ctttccaaac atcagagaga gcttccaggg acacttcgc aatgcaagtg 2880
cctgacagca tgccaaggaa acagtccat agttctcgag aagatcttcg ccgtagcaca 2940
ggaaaaagag cacataaacg agacatttgc ctcaaaatgc atcatattgg ttgccagctt 3000
tgcttttcca gaaggtcaag agatgccagt ttcatacaga atacgtattt gcacaaatta 3060
attggagaac atgaagctaa aatagttttg atgccagttc atacagatgc tgatattgac 3120
aaaattcagc tggagattca ggcaggatct agagcagctg ccagaataat tactgaggta 3180
aacccagagt ctgaggaaga ggatgaatca tctccatatg aggacattca agctaaactg 3240
aagaggattc taggcattga cagtatgttc aaggttgcaa acaaaacacg gcacccgaaa 3300
aatcgaccat ctaagaaagg aaacactgtg ctagcagagt ttgggacaga gcctgatgca 3360
aaa                                                               3363

SEQ ID NO: 59        moltype = AA   length = 1121
FEATURE              Location/Qualifiers
source               1..1121
                     mol_type = protein
                     organism = Gallus gallus
```

-continued

```
SEQUENCE: 59
MRGIILALVL TLVGSQKFDI DPGFNSRRSY LYNYEGSMLN GLQDRSLGKA GVRLSSKLEI    60
SGLPENAYLL KVRSPQVEEY NGVWPRDPFT RSSKITQVIS SCFTRLFKFE YSSGRIGNIY   120
APEDCPDLCV NIVRGILNMF QMTIKKSQNV YELQEAGIGG ICHARYVIQE DRKNSRIYVT   180
RTVDLNNCQE KVQKSIGMAY IYPCPVDVMK ERLTKGTTAF SYKLKQSDSG TLITDVSSRQ   240
VYQISPFNEP TGVAVMEARQ QLTLVEVRSE RGSAPDVPMQ NYGSLRYRFP AVLPQMPLQL   300
IKTKNPEQRI IETLQHIVLN NQQDFHDDVS YRFLEVVQLC RIANADNLES IWRQVSDKPR   360
YRRWLLSAVS ASGTTETLKF LKNRIRNDDL NYIQTLLTVS LTLHLLQADE HTLPIAADLM   420
TSSRIQKNPV LQQVACLGYS SVVNRYCSQT SACPKEALQP IHDLADEAIS RGREDKMKLA   480
LKCIGNMGEP ASLKRILKFL PISSSSAADI PVHIQIDAIT ALKKIAWKDP KTVQGYLIQI   540
LADQSLPPEV RMMACAVIFE TRPALALITT IANVAMKESN MQVASFVYSH MKSLSKSRLP   600
FMYNISSACN IALKLLSPKL DSMSYRYSKV IRADTYFDNY RVGATGEIFV VNSPRTMFPS   660
AIISKLMANS AGSVADLVEV GIRVEGLADV IMKRNIPFAE YPTYKQIKEL GKALQGWKEL   720
PTETPLVSAY LKILGQEVAF ININKELLQQ VMKTVVEPAD RNAAIKRIAN QIRNSIAGQW   780
TQPVWMGELR YVVPSCLGLP LEYGSYTTAL ARAAVSVEGK MTPPLTGDFR LSQLLESTMQ   840
IRSDLKPSLY VHTVATMGVN TEYFQHAVEI QGEVQTRMPM KFDAKIDVKL KNLKIETNPC   900
REETEIVVGR HKAFAVSRNI GELGVEKRTS ILPEDAPLDV TEEPFQTSER ASREHFAMQG   960
PDSMPRKQSH SSREDLRRST GKRAHKRDIC LKMHHIGCQL CFSRRSRDAS FIQNTYLHKL  1020
IGEHEAKIVL MPVHTDADID KIQLEIQAGS RAAARIITEV NPESEEEDES SPYEDIQAKL  1080
KRILGIDSMF KVANKTRHPK NRPSKKGNTV LAEFGTEPDA K                     1121

SEQ ID NO: 60              moltype = AA   length = 10
FEATURE                    Location/Qualifiers
source                     1..10
                           mol_type = protein
                           organism = Gallus gallus
SEQUENCE: 60
ADQSLPPEVR                                                          10

SEQ ID NO: 61              moltype = AA   length = 9
FEATURE                    Location/Qualifiers
source                     1..9
                           mol_type = protein
                           organism = Gallus gallus
SEQUENCE: 61
ADTYFDNYR                                                            9

SEQ ID NO: 62              moltype = AA   length = 7
FEATURE                    Location/Qualifiers
source                     1..7
                           mol_type = protein
                           organism = Gallus gallus
SEQUENCE: 62
AVIFETR                                                              7

SEQ ID NO: 63              moltype = AA   length = 12
FEATURE                    Location/Qualifiers
source                     1..12
                           mol_type = protein
                           organism = Gallus gallus
SEQUENCE: 63
DASFIQNTYL HK                                                       12

SEQ ID NO: 64              moltype = AA   length = 9
FEATURE                    Location/Qualifiers
source                     1..9
                           mol_type = protein
                           organism = Gallus gallus
SEQUENCE: 64
DLADEAISR                                                            9

SEQ ID NO: 65              moltype = AA   length = 16
FEATURE                    Location/Qualifiers
source                     1..16
                           mol_type = protein
                           organism = Gallus gallus
SEQUENCE: 65
EALQPIHDLA DEAISR                                                   16

SEQ ID NO: 66              moltype = AA   length = 9
FEATURE                    Location/Qualifiers
source                     1..9
                           mol_type = protein
                           organism = Gallus gallus
SEQUENCE: 66
EETEIVVGR                                                            9

SEQ ID NO: 67              moltype = AA   length = 9
FEATURE                    Location/Qualifiers
```

```
source                     1..9
                           mol_type = protein
                           organism = Gallus gallus
SEQUENCE: 67
EIFVVNSPR                                                                9

SEQ ID NO: 68              moltype = AA  length = 14
FEATURE                    Location/Qualifiers
source                     1..14
                           mol_type = protein
                           organism = Gallus gallus
SEQUENCE: 68
ELPTETPLVS AYLK                                                          14

SEQ ID NO: 69              moltype = AA  length = 10
FEATURE                    Location/Qualifiers
source                     1..10
                           mol_type = protein
                           organism = Gallus gallus
SEQUENCE: 69
FDIDPGFNSR                                                               10

SEQ ID NO: 70              moltype = AA  length = 7
FEATURE                    Location/Qualifiers
source                     1..7
                           mol_type = protein
                           organism = Gallus gallus
SEQUENCE: 70
FEYSSGR                                                                  7

SEQ ID NO: 71              moltype = AA  length = 25
FEATURE                    Location/Qualifiers
source                     1..25
                           mol_type = protein
                           organism = Gallus gallus
SEQUENCE: 71
FLPISSSSAA DIPVHIQIDA ITALK                                              25

SEQ ID NO: 72              moltype = AA  length = 8
FEATURE                    Location/Qualifiers
source                     1..8
                           mol_type = protein
                           organism = Gallus gallus
SEQUENCE: 72
GYSSVVNR                                                                 8

SEQ ID NO: 73              moltype = AA  length = 12
FEATURE                    Location/Qualifiers
source                     1..12
                           mol_type = protein
                           organism = Gallus gallus
SEQUENCE: 73
IANADNLESI WR                                                            12

SEQ ID NO: 74              moltype = AA  length = 8
FEATURE                    Location/Qualifiers
source                     1..8
                           mol_type = protein
                           organism = Gallus gallus
SEQUENCE: 74
IDAITALK                                                                 8

SEQ ID NO: 75              moltype = AA  length = 24
FEATURE                    Location/Qualifiers
source                     1..24
                           mol_type = protein
                           organism = Gallus gallus
SEQUENCE: 75
IITEVNPESE EEDESSPYED IQAK                                               24

SEQ ID NO: 76              moltype = AA  length = 12
FEATURE                    Location/Qualifiers
source                     1..12
                           mol_type = protein
                           organism = Gallus gallus
SEQUENCE: 76
ILADQSLPPE VR                                                            12

SEQ ID NO: 77              moltype = AA  length = 13
```

-continued

```
FEATURE              Location/Qualifiers
source               1..13
                     mol_type = protein
                     organism = Gallus gallus
SEQUENCE: 77
ILGQEVAFIN INK                                                    13

SEQ ID NO: 78        moltype = AA  length = 10
FEATURE              Location/Qualifiers
source               1..10
                     mol_type = protein
                     organism = Gallus gallus
SEQUENCE: 78
IQLEIQAGSR                                                        10

SEQ ID NO: 79        moltype = AA  length = 13
FEATURE              Location/Qualifiers
source               1..13
                     mol_type = protein
                     organism = Gallus gallus
SEQUENCE: 79
IRNDDLNYIQ TLL                                                    13

SEQ ID NO: 80        moltype = AA  length = 8
FEATURE              Location/Qualifiers
source               1..8
                     mol_type = protein
                     organism = Gallus gallus
SEQUENCE: 80
LADEAISR                                                          8

SEQ ID NO: 81        moltype = AA  length = 14
FEATURE              Location/Qualifiers
source               1..14
                     mol_type = protein
                     organism = Gallus gallus
SEQUENCE: 81
LEISGLPENA YLLK                                                   14

SEQ ID NO: 82        moltype = AA  length = 9
FEATURE              Location/Qualifiers
source               1..9
                     mol_type = protein
                     organism = Gallus gallus
SEQUENCE: 82
LGYSSVVNR                                                         9

SEQ ID NO: 83        moltype = AA  length = 15
FEATURE              Location/Qualifiers
source               1..15
                     mol_type = protein
                     organism = Gallus gallus
SEQUENCE: 83
LIQILADQSL PPEVR                                                  15

SEQ ID NO: 84        moltype = AA  length = 16
FEATURE              Location/Qualifiers
source               1..16
                     mol_type = protein
                     organism = Gallus gallus
SEQUENCE: 84
LKQSDSGTLI TDVSSR                                                 16

SEQ ID NO: 85        moltype = AA  length = 15
FEATURE              Location/Qualifiers
source               1..15
                     mol_type = protein
                     organism = Gallus gallus
SEQUENCE: 85
LLSAVSASGT TETLK                                                  15

SEQ ID NO: 86        moltype = AA  length = 14
FEATURE              Location/Qualifiers
source               1..14
                     mol_type = protein
                     organism = Gallus gallus
SEQUENCE: 86
LSAVSASGTT ETLK                                                   14
```

-continued

```
SEQ ID NO: 87              moltype = AA  length = 11
FEATURE                    Location/Qualifiers
source                     1..11
                           mol_type = protein
                           organism = Gallus gallus SEQUENCE: 87
NIPFAEYPTY K                                                          11

SEQ ID NO: 88              moltype = AA  length = 11
FEATURE                    Location/Qualifiers
source                     1..11
                           mol_type = protein
                           organism = Gallus gallus SEQUENCE: 88
PALALITTIA N                                                          11

SEQ ID NO: 89              moltype = AA  length = 8
FEATURE                    Location/Qualifiers
source                     1..8
                           mol_type = protein
                           organism = Gallus gallus SEQUENCE: 89
PPLTGDFR                                                              8

SEQ ID NO: 90              moltype = AA  length = 9
FEATURE                    Location/Qualifiers
source                     1..9
                           mol_type = protein
                           organism = Gallus gallus SEQUENCE: 90
QQLTLVEVR                                                             9

SEQ ID NO: 91              moltype = AA  length = 14
FEATURE                    Location/Qualifiers
source                     1..14
                           mol_type = protein
                           organism = Gallus gallus SEQUENCE: 91
QSDSGTLITD VSSR                                                       14

SEQ ID NO: 92              moltype = AA  length = 12
FEATURE                    Location/Qualifiers
source                     1..12
                           mol_type = protein
                           organism = Gallus gallus SEQUENCE: 92
RNIPFAEYPT YK                                                         12

SEQ ID NO: 93              moltype = AA  length = 14
FEATURE                    Location/Qualifiers
source                     1..14
                           mol_type = protein
                           organism = Gallus gallus SEQUENCE: 93
SAGSVADLVE VGIR                                                       14

SEQ ID NO: 94              moltype = AA  length = 13
FEATURE                    Location/Qualifiers
source                     1..13
                           mol_type = protein
                           organism = Gallus gallus SEQUENCE: 94
SAVSASGTTE TLK                                                        13

SEQ ID NO: 95              moltype = AA  length = 8
FEATURE                    Location/Qualifiers
source                     1..8
                           mol_type = protein
                           organism = Gallus gallus SEQUENCE: 95
SDLKPSLY                                                              8

SEQ ID NO: 96              moltype = AA  length = 11
FEATURE                    Location/Qualifiers
source                     1..11
                           mol_type = protein
                           organism = Gallus gallus SEQUENCE: 96
SGTLITDVSS R                                                          11
```

-continued

```
SEQ ID NO: 97            moltype = AA  length = 13
FEATURE                  Location/Qualifiers
source                   1..13
                         mol_type = protein
                         organism = Gallus gallus
SEQUENCE: 97
SPQVEEYNGV WPR                                                  13

SEQ ID NO: 98            moltype = AA  length = 22
FEATURE                  Location/Qualifiers
source                   1..22
                         mol_type = protein
                         organism = Gallus gallus
SEQUENCE: 98
TSILPEDAPL DVTEEPFQTS ER                                        22

SEQ ID NO: 99            moltype = AA  length = 20
FEATURE                  Location/Qualifiers
source                   1..20
                         mol_type = protein
                         organism = Gallus gallus
SEQUENCE: 99
TVQGYLIQIL ADQSLPPEVR                                           20

SEQ ID NO: 100           moltype = AA  length = 8
FEATURE                  Location/Qualifiers
source                   1..8
                         mol_type = protein
                         organism = Gallus gallus
SEQUENCE: 100
TVVEPADR                                                        8

SEQ ID NO: 101           moltype = AA  length = 14
FEATURE                  Location/Qualifiers
source                   1..14
                         mol_type = protein
                         organism = Gallus gallus
SEQUENCE: 101
VGATGEIFVV NSPR                                                 14

SEQ ID NO: 102           moltype = AA  length = 11
FEATURE                  Location/Qualifiers
source                   1..11
                         mol_type = protein
                         organism = Gallus gallus
SEQUENCE: 102
VSASGTTETL K                                                    11

SEQ ID NO: 103           moltype = AA  length = 16
FEATURE                  Location/Qualifiers
source                   1..16
                         mol_type = protein
                         organism = Gallus gallus
SEQUENCE: 103
WLLSAVSASG TTETLK                                               16

SEQ ID NO: 104           moltype = AA  length = 8
FEATURE                  Location/Qualifiers
source                   1..8
                         mol_type = protein
                         organism = Gallus gallus
SEQUENCE: 104
YVIQEDRK                                                        8

SEQ ID NO: 105           moltype = DNA  length = 5550
FEATURE                  Location/Qualifiers
source                   1..5550
                         mol_type = other DNA
                         organism = Gallus gallus
SEQUENCE: 105
atgagggggga tcatactggc attagtgctc acccttgtag gcagccagaa gtttgacatt  60
gacccaggat tcaatagcag aaggagttac ctgtacaact atgaaggttc tatgttgaat  120
gggcttcaag acagaagttt gggcaaagct ggtgtgcgct tgagcagcaa gctagagatc  180
agtgggctac cagagaatgc ttacctcctc aaggtccgct ctccacaagt ggaggagtac  240
aatgggtct ggcccaggga tcccttcact cgatcttcca aaatcaccca agtgatctca  300
tcgtgtttca cccggctctt caaatttgaa tacagcagtg gacggatcgg aaacatttat  360
gccccagaag actgcccaga tctgtgtgtt aacatagtga gaggaatatt gaacatgttc  420
cagatgacca ttaaaaaatc acagaacgtc tacgaattac aagaggctgg aattggaggt  480
```

```
atttgtcatg caaggtatgt cattcaggaa gacaggaaga atagccgaat ctatgttacc    540
agaactgtgg acttgaataa ttgccaggaa aaggtgcaaa aaagcattgg aatggcttac    600
atctatccct gccctgtgga cgtgatgaaa gaaaggctca ccaaaggac caccgctttc    660
tcctacaagc tgaagcagtc agacagcggc acgctgatca cagatgtctc gtcgcggcag    720
gtgtatcaga tctccccatt caatgagccc actgggtgg ctgtcatgga agcaagacag    780
cagctcactt tggtcgaggt gagaagtgag cggggcagtg ccccagatgt ccccatgcag    840
aactatggca gccttcgcta ccgcttccca gccgtactgc cacagatgcc acttcagctg    900
atcaagacaa aaaaccctga gcaacggata gtagaaacgc tgcagcacat agtcctgaat    960
aaccaacaag atttccatga cgatgtttca tacagattct tagaggtggt ccagctttgt   1020
cggatagcaa atgctgacaa tcttgagtct atctggagca aagtttcaga taaacctcgt   1080
tacaggcgat ggctcctgag cgcagtttct gcgagtggca ccacagaaac actaaaattc   1140
cttaagaaca gaattcgcaa tgatgacctc aactacattc agacccttct aactgtttct   1200
ttgactcttc atttattgca agctgatgaa cacacacttc caatagcagc agatttaatg   1260
accagctctc gaattcagaa aaatcctgtg cttcagcaag tggcctgctt gggatatagc   1320
tctgtagtca acagatactg ctctcagacc tcagcatgtc ctaaggaagc tcttcagccc   1380
atccatgacc tggcagatga agcaatcagc aggggccgtg aagacaaaat gaaattagct   1440
ctaaagtgca ttggtaacat gggagaacca gccagcttaa agcgcatcct gaagttcctt   1500
ccaatatctt catccagtgc tgctgatatc ccagtccaca ttcagataga tgccataacg   1560
gccttgaaaa agatagcttg gaaggacccc aaaacagtgc agggctatct catccagatc   1620
cttgcagacc aatcacttcc ccctgaggtg cgaatgatgg cttgtgctgt tatctttgag   1680
acaaggcctg cccttgcttt gataacgact atagctaacg tggcaatgaa ggagagcaat   1740
atgcaagtgg ccagttttgt atattcccac atgaagtctt tgtcaaagag cagattgcca   1800
tttatgtaca acatatcttc cgcttgtaac attgcccta agctcctgtc ccccaaactg   1860
gacagtatga gctatcggta cagcaaggtc attcgagcag acacttactt tgataactat   1920
agagttggtg ctactggaga aatctttgtt gtgaacagcc caagaactat gttcccatca   1980
gcaataattt ccaaattgat ggcaaattct gcaggttcag tggctgatct ggtagaggtt   2040
ggcatccgag tggaaggcct cgcagatgtc ataatgaaaa gaaacatccc atttgctgaa   2100
tatcccacat acaagcagat aaaggagctt ggaaaagctc tgcagggatg gaaagagctg   2160
ccgacagaaa ccccttttggt atcagcctac ttgaaaatac ttggccaaga agtggccttc   2220
atcaacatca acaaggaact cctgcaacag gtcatgaaga ctgtagtgga acctgctgat   2280
cgaaacgcag caataaagag aatcgccaac cagatccgca acagcattgc agggcagtga   2340
acgcagccgg tgtggatggg agagctgcga tacgtggttc ccagctgtct cggcctgccg   2400
ctggagtacg ggtcctacac caccgccctg gcacgagctg cagtcagcgt tgagggaaag   2460
atgacgccgc ctttaaccgg agatttcaga ctttctcagt tgcttgaatc caccatgcag   2520
attcggtctg acttaaagcc cagtttatat gtgcatacag ttgcaacgat gggtgtcaac   2580
acagaatact ttcaacatgc tgttgaaatt caaggcgagg tccagacaag aatgccaatg   2640
aagtttgatg ccaagataga tgtgaaattg aaaaacctta agattgaaac gaacccatgc   2700
cgtgaggaaa ctgagatagt ggttggaaga cataaggctt ttgctgtatc aaggaacata   2760
ggagaactag gtgttgaaaa gaggacctca attctgccga atacgtattt attagatgtt   2820
acagaagaac ctttccaaac atcagagaga gcttccaggg aacacttcgc aatgcaaggg   2880
cctgacagca tgccaaggaa acagtcccat agttctcgag aagatcttcg ccgtagcaca   2940
ggaaaaaagag cacataaacg agacatttgc ctcaaaatgc atcatattgg ttgccagctt   3000
tgctttttcca gaaggtcaag agatgccagt ttcatacaga atacgtatttt gcacaaatta   3060
attggagaac atgaagctaa aatagttttg atgccagttc atacagatgc tgatattgac   3120
aaaaattcagc tggagattca ggcaggatct agagcagctg ccagaataat tactgaggta   3180
aacccagagt ctgaggaaga ggatgaatca tctccatatg aggacattca agctaaactg   3240
aagaggattc taggcattga cagtatgttc aaggttgcaa acaaaacacg gcacccgaaa   3300
aatcgaccat ctaagaaagg aaaacactgtg ctagcagagt ttgggacaga gcctgatgca   3360
aaaacttcct ccagctcatc ttctgcctcc tcaactgcca cctcttcttc ctcatcatct   3420
gcctcctctc ctaatcgtaa aaagcctatg gatgaagagg agaatgatca agtaaagcaa   3480
gcaagaaaca aagatgcaag cagcagcaag aggagcagca agacagtaa cagcagcaag   3540
agaagcagca gcaagagcag taacagcagc aagagaagca gcagcagcag tagcagtagc   3600
agtagcagca gcaggagcag cagcagtagc agcagtagta gcagtaacag caagagcagc   3660
agtagcagca gcaagagcag cagtagcagc agcaggagca gaagcagcag caagagcagc   3720
agtagcagca gcagcagtag cagcagcaaa gtagcagtag taggagcagt   3780
agcagcagca gcaagtcaag cagtcaccat agccatagcc atcattcagg gcatctaaat   3840
ggcagcagca gcagcagcag cagcagcagg tcagtgagtc accacagcca tgagcatcac   3900
tcaggacatc tggaagatga cagcagtagc agcagcagca gcagcgtgct ttccaaaata   3960
tggggggcgtc atgagattta tcagtatcgc tttagatcag cacacagaca agagttcccc   4020
aaaagaaaac tcccaggtga ccgcgctacc agcagatact cctctaccag atccagccat   4080
gacacatccc gagctgcttc ctggcctaag tttctgggtg acatcaaaac cccagtgtta   4140
gctgctttttc tccatggcat tagtaacaat aagaagacag gaggcctcca gcttgtggta   4200
tatgctgata ccgactcggt caggccgcgg gtgcaggtat ttgtgacaaa cctcacagat   4260
tcgagcaagt ggaagctctg cgcagatgct tcggtccgca atgctcacaa ggcagtggcc   4320
tacgtgaaat ggggctggga ctgccgggac tacaaggttt ctactgagct ggtaactggg   4380
cggtttgctg ggcaccctgc tgcacaagtg aagctggagt ggcccaaggt tccttcgaat   4440
gtcagatcag tggttgaatg gttttacgag tttgtccctg gggctgcatt tatgctgggt   4500
ttctctgaga gaatggacaa gaatccttct cgacaagcca ggatggttgt ggctctaact   4560
tctccgagga catgtgatgt tgttgtcaag ctgcctgata taatcctcta tcaaaaagcc   4620
gtgaggcttc ctctatcact ccctgtgggt ccaaggatcc cagcttcaga gctgcagcct   4680
ccaatctgga acgtctttgc tgaagccccc tctgccgtgc tcgagaattt gaaagctcgc   4740
tgctcagttt cgtacaacaa gatcaaaacc tttaatgaag tcaagttcaa ctactcgatg   4800
cccgcaaact gctatcacat cttggttcag gattgcagct ctgaacttaa gttcctggtg   4860
atgataaaaa gtgctggaga agctacaaac cttaaagcca tcaacatcaa gattggcaat   4920
catgaaattg atatgcatcc tgtgaatgga caggtgaaac tgctggtaga tggggctgag   4980
agccccacag ccaacatttc cctcatatct gctggtgctt ctctgtggat tcacaatgaa   5040
aaccaagggt ttgcacttgc tgccccaggc catggtatcg ataaattgta cttcgatgga   5100
aaaacaatca cgattcaagt tccttatgg atggcaggga aaacatgtgg aatctgtgga   5160
aaatatgatg cagaatgcga aacaggagtat cggatgccca atggatatct agctaaaaat   5220
```

```
gccgtgagct ttggtcattc ttggatcttg gaagaagcgc cctgtagagg agccttgtaaa   5280
ctgcatcgtt cattcgtgaa gcttgagaag acggttcagc tggcgggtgt tgattccaag   5340
tgctactcta cagagcctgt gctgcgctgt gcaaagggat gctctgctac caagacaact   5400
ccagtaactg tttggcttcca ctgcctccca gctgattcag ctaacagcct aactgacaaa   5460
cagatgaagt acgaccagaa gtcagaagac atgcaggata ctgttgatgc acacacaacg   5520
tgttcatgtg agaatgagga atgcagtaca                                     5550
```

SEQ ID NO: 106            moltype = AA  length = 1850
FEATURE                   Location/Qualifiers
source                    1..1850
                          mol_type = protein
                          organism = Gallus gallus
SEQUENCE: 106
```
MRGIILALVL TLVGSQKFDI DPGFNSRRSY LYNYEGSMLN GLQDRSLGKA GVRLSSKLEI   60
SGLPENAYLL KVRSPQVEEY NGVWPRDPFT RSSKITQVIS SCFTRLFKFE YSSGRIGNIY   120
APEDCPDLCV NIVRGILNMF QMTIKKSQNV YELQEAGIGG ICHARYVIQE DRKNSRIYVT   180
RTVDLNNCQE KVQKSIGMAY IYPCPVDVMK ERLTKGTTAF SYKLKQSDSG TLITDVSSRQ   240
VYQISPFNEP TGVAVMEARQ QLTLVEVRSE RGSAPDVPMQ NYGSLRYRFP AVLPQMPLQL   300
IKTKNPEQRI VETLQHIVLN NQQDFHDDVS YRFLEVVQLC RIANADNLES IWRQVSDKPR   360
YRRWLLSAVS ASGTTETLKF LKNRIRNDDL NYIQTLLTVS LTLHLLQADE HTLPIAADLM   420
TSSRIQKNPV LQQVACLGYS SVVNRYCSQT SACPKEALQP IHDLADEAIS RGREDKMKLA   480
LKCIGNMGEP ASLKRILKFL PISSSSAADI PVHIQIDAIT ALKKIAWKDP KTVQGYLIQI   540
LADQSLPPEV RMMACAVIFE TRPALALITT IANVAMKESN MQVASFVYSH MKSLSKSRLP   600
FMYNISSACN IALKLLSPKL DSMSYRYSKV IRADTYFDNY RVGATGEIFV VNSPRTMFPS   660
AIISKLMANS AGSVADLVEV GIRVEGLADV IMKRNIPFAE YPTYKQIKEL GKALQGWKEL   720
PTETPLVSAY LKILGQEVAF ININKELLQQ VMKTVVEPAD RNAAIKRIAN QIRNSIAGQW   780
TQPVWMGELR YVVPSCLGLP LEYGSYTTAL ARAAVSVEGK MTPPLTGDFR LSQLLESTMQ   840
IRSDLKPSLY VHTVATMGVN TEYFQHAVEI QGEVQTRMPM KFDAKIDVKL KNLKIETNPC   900
REETEIVVGR HKAFAVSRNI GELGVEKRTS ILPEDAPLDV TEEPFQTSER ASREHFAMQG   960
PDSMPRKQSH SSREDLRRST GKRAHKRDIC LKMHHIGCQL CFSRRSRDAS FIQNTYLHKL   1020
IGEHEAKIVL MPVHTDADID KIQLEIQAGS RAAARIITEV NPESEEEDES SPYEDIQAKL   1080
KRILGIDSMF KVANKTRHPK NRPSKKGNTV LAEFGTEPDA KTSSSSSSAS STATSSSSSS   1140
ASSPNRKKPM DEEENDQVKQ ARNKDASSSS RSSKSSNSSK RSSSKSSNSS KRSSSSSSSS   1200
SSSSRSSSSS SSSSSSNSKSS SSSSKSSSSS SRSRSSSKSS SRSRSSSSRSS SSSSSSRSS   1260
SSSSKSSSHH SHSHHSGHLN GSSSSSSSSR SVSHHSHEHH SGHLEDDSSS SSSSSVLSKI   1320
WGRHEIYQYR FRSAHRQEFP KRKLPGDRAT SRYSSTRSSH DTSRAASWPK FLGDIKTPVL   1380
AAFLHGISNN KKTGGLQLVV YADTDSVRPR VQVFVTNLTD SSKWKLCADA SVRNAHKAVA   1440
YVKWGWDCRD YKVSTELVTG RFAGHPAAQV KLEWPKVPSN VRSVVEWFYE FVPGAAFMLG   1500
FSERMDKNPS RQARMVVALT SPRTCDVVVK LPDIILYQKA VRLPLSLPVG PRIPASELQP   1560
PIWNVFAEAP SAVLENLKAR CSVSYNKIKT FNEVKFNYSM PANCYHILVQ DCSSELKFLV   1620
MMKSAGEATN LKAINIKIGS HEIDMHPVNG QVKLLVDGAE SPTANISLIS AGASLWIHNE   1680
NQGFALAAPG HGIDKLYFDG KTITIQVPLW MAGKTCGICG KYDAECEQEY RMPNGYLAKN   1740
AVSFGHSWIL EEAPCRGACK LHRSFVKLEK TVQLAGVDSK CYSTEPVLRC AKGCSATKTT   1800
PVTVGFHCLP ADSANSLTDK QMKYDQKSED MQDTVDAHTT CSCENEECST               1850
```

SEQ ID NO: 107            moltype = AA  length = 9
FEATURE                   Location/Qualifiers
source                    1..9
                          mol_type = protein
                          organism = Gallus gallus
SEQUENCE: 107
```
ADTYFDNYR                                                             9
```

SEQ ID NO: 108            moltype = AA  length = 10
FEATURE                   Location/Qualifiers
source                    1..10
                          mol_type = protein
                          organism = Gallus gallus
SEQUENCE: 108
```
AEFGTEPDAK                                                            10
```

SEQ ID NO: 109            moltype = AA  length = 7
FEATURE                   Location/Qualifiers
source                    1..7
                          mol_type = protein
                          organism = Gallus gallus
SEQUENCE: 109
```
AEYPTYK                                                               7
```

SEQ ID NO: 110            moltype = AA  length = 12
FEATURE                   Location/Qualifiers
source                    1..12
                          mol_type = protein
                          organism = Gallus gallus
SEQUENCE: 110
```
ATGEIFVVNS PR                                                         12
```

SEQ ID NO: 111            moltype = AA  length = 11
FEATURE                   Location/Qualifiers -continued

```
source                   1..11
                         mol_type = protein
                         organism = Gallus gallus
SEQUENCE: 111
AVEIQGEVQT R                                                          11

SEQ ID NO: 112           moltype = AA   length = 7
FEATURE                  Location/Qualifiers
source                   1..7
                         mol_type = protein
                         organism = Gallus gallus
SEQUENCE: 112
AVIFETR                                                               7

SEQ ID NO: 113           moltype = AA   length = 12
FEATURE                  Location/Qualifiers
source                   1..12
                         mol_type = protein
                         organism = Gallus gallus
SEQUENCE: 113
AVSASGTTET LK                                                         12

SEQ ID NO: 114           moltype = AA   length = 16
FEATURE                  Location/Qualifiers
source                   1..16
                         mol_type = protein
                         organism = Gallus gallus
SEQUENCE: 114
EALQPIHDLA DEAISR                                                     16

SEQ ID NO: 115           moltype = AA   length = 9
FEATURE                  Location/Qualifiers
source                   1..9
                         mol_type = protein
                         organism = Gallus gallus
SEQUENCE: 115
EETEIVVGR                                                             9

SEQ ID NO: 116           moltype = AA   length = 14
FEATURE                  Location/Qualifiers
source                   1..14
                         mol_type = protein
                         organism = Gallus gallus
SEQUENCE: 116
ELPTETPLVS AYLK                                                       14

SEQ ID NO: 117           moltype = AA   length = 10
FEATURE                  Location/Qualifiers
source                   1..10
                         mol_type = protein
                         organism = Gallus gallus
SEQUENCE: 117
FDIDPGFNSR                                                            10

SEQ ID NO: 118           moltype = AA   length = 7
FEATURE                  Location/Qualifiers
source                   1..7
                         mol_type = protein
                         organism = Gallus gallus
SEQUENCE: 118
FEYSSGR                                                               7

SEQ ID NO: 119           moltype = AA   length = 8
FEATURE                  Location/Qualifiers
source                   1..8
                         mol_type = protein
                         organism = Gallus gallus
SEQUENCE: 119
GTTAFSYK                                                              8

SEQ ID NO: 120           moltype = AA   length = 10
FEATURE                  Location/Qualifiers
source                   1..10
                         mol_type = protein
                         organism = Gallus gallus
SEQUENCE: 120
IANADNLESI                                                            10

SEQ ID NO: 121           moltype = AA   length = 12
```

-continued

| FEATURE | Location/Qualifiers | |
|---|---|---|
| source | 1..12 | |
| | mol_type = protein | |
| | organism = Gallus gallus | |
| SEQUENCE: 121 | | |
| ILADQSLPPE VR | | 12 |
| | | |
| SEQ ID NO: 122 | moltype = AA  length = 13 | |
| FEATURE | Location/Qualifiers | |
| source | 1..13 | |
| | mol_type = protein | |
| | organism = Gallus gallus | |
| SEQUENCE: 122 | | |
| ILGQEVAFIN INK | | 13 |
| | | |
| SEQ ID NO: 123 | moltype = AA  length = 10 | |
| FEATURE | Location/Qualifiers | |
| source | 1..10 | |
| | mol_type = protein | |
| | organism = Gallus gallus | |
| SEQUENCE: 123 | | |
| IQLEIQAGSR | | 10 |
| | | |
| SEQ ID NO: 124 | moltype = AA  length = 14 | |
| FEATURE | Location/Qualifiers | |
| source | 1..14 | |
| | mol_type = protein | |
| | organism = Gallus gallus | |
| SEQUENCE: 124 | | |
| LEISGLPENA YLLK | | 14 |
| | | |
| SEQ ID NO: 125 | moltype = AA  length = 9 | |
| FEATURE | Location/Qualifiers | |
| source | 1..9 | |
| | mol_type = protein | |
| | organism = Gallus gallus | |
| SEQUENCE: 125 | | |
| LGYSSVVNR | | 9 |
| | | |
| SEQ ID NO: 126 | moltype = AA  length = 15 | |
| FEATURE | Location/Qualifiers | |
| source | 1..15 | |
| | mol_type = protein | |
| | organism = Gallus gallus | |
| SEQUENCE: 126 | | |
| LIQILADQSL PPEVR | | 15 |
| | | |
| SEQ ID NO: 127 | moltype = AA  length = 16 | |
| FEATURE | Location/Qualifiers | |
| source | 1..16 | |
| | mol_type = protein | |
| | organism = Gallus gallus | |
| SEQUENCE: 127 | | |
| LKQSDSGTLI TDVSSR | | 16 |
| | | |
| SEQ ID NO: 128 | moltype = AA  length = 15 | |
| FEATURE | Location/Qualifiers | |
| source | 1..15 | |
| | mol_type = protein | |
| | organism = Gallus gallus | |
| SEQUENCE: 128 | | |
| LLSAVSASGT TETLK | | 15 |
| | | |
| SEQ ID NO: 129 | moltype = AA  length = 10 | |
| FEATURE | Location/Qualifiers | |
| source | 1..10 | |
| | mol_type = protein | |
| | organism = Gallus gallus | |
| SEQUENCE: 129 | | |
| LPLSLPVGPR | | 10 |
| | | |
| SEQ ID NO: 130 | moltype = AA  length = 14 | |
| FEATURE | Location/Qualifiers | |
| source | 1..14 | |
| | mol_type = protein | |
| | organism = Gallus gallus | |
| SEQUENCE: 130 | | |
| LSAVSASGTT ETLK | | 14 |

-continued

```
SEQ ID NO: 131          moltype = AA  length = 11
FEATURE                 Location/Qualifiers
source                  1..11
                        mol_type = protein
                        organism = Gallus gallus
SEQUENCE: 131
NDDLNYIQTL L                                                        11

SEQ ID NO: 132          moltype = AA  length = 9
FEATURE                 Location/Qualifiers
source                  1..9
                        mol_type = protein
                        organism = Gallus gallus
SEQUENCE: 132
NIGELGVEK                                                          9

SEQ ID NO: 133          moltype = AA  length = 11
FEATURE                 Location/Qualifiers
source                  1..11
                        mol_type = protein
                        organism = Gallus gallus
SEQUENCE: 133
NIPFAEYPTY K                                                       11

SEQ ID NO: 134          moltype = AA  length = 11
FEATURE                 Location/Qualifiers
source                  1..11
                        mol_type = protein
                        organism = Gallus gallus
SEQUENCE: 134
PALALITTIA N                                                       11

SEQ ID NO: 135          moltype = AA  length = 9
FEATURE                 Location/Qualifiers
source                  1..9
                        mol_type = protein
                        organism = Gallus gallus
SEQUENCE: 135
QQLTLVEVR                                                          9

SEQ ID NO: 136          moltype = AA  length = 14
FEATURE                 Location/Qualifiers
source                  1..14
                        mol_type = protein
                        organism = Gallus gallus
SEQUENCE: 136
QSDSGTLITD VSSR                                                    14

SEQ ID NO: 137          moltype = AA  length = 14
FEATURE                 Location/Qualifiers
source                  1..14
                        mol_type = protein
                        organism = Gallus gallus
SEQUENCE: 137
SAGSVADLVE VGIR                                                    14

SEQ ID NO: 138          moltype = AA  length = 13
FEATURE                 Location/Qualifiers
source                  1..13
                        mol_type = protein
                        organism = Gallus gallus
SEQUENCE: 138
SAVSASGTTE TLK                                                     13

SEQ ID NO: 139          moltype = AA  length = 8
FEATURE                 Location/Qualifiers
source                  1..8
                        mol_type = protein
                        organism = Gallus gallus
SEQUENCE: 139
SDLKPSLY                                                           8

SEQ ID NO: 140          moltype = AA  length = 18
FEATURE                 Location/Qualifiers
source                  1..18
                        mol_type = protein
                        organism = Gallus gallus
SEQUENCE: 140
TGGLQLVVYA DTDSVRPR                                                18
```

```
SEQ ID NO: 141          moltype = AA   length = 15
FEATURE                 Location/Qualifiers
source                  1..15
                        mol_type = protein
                        organism = Gallus gallus
SEQUENCE: 141
TPVLAAFLHG ISNNK                                                       15

SEQ ID NO: 142          moltype = AA   length = 20
FEATURE                 Location/Qualifiers
source                  1..20
                        mol_type = protein
                        organism = Gallus gallus
SEQUENCE: 142
TVQGYLIQIL ADQSLPPEVR                                                  20

SEQ ID NO: 143          moltype = AA   length = 10
FEATURE                 Location/Qualifiers
source                  1..10
                        mol_type = protein
                        organism = Gallus gallus
SEQUENCE: 143
TVQLAGVDSK                                                             10

SEQ ID NO: 144          moltype = AA   length = 8
FEATURE                 Location/Qualifiers
source                  1..8
                        mol_type = protein
                        organism = Gallus gallus
SEQUENCE: 144
TVVEPADR                                                                8

SEQ ID NO: 145          moltype = AA   length = 10
FEATURE                 Location/Qualifiers
source                  1..10
                        mol_type = protein
                        organism = Gallus gallus
SEQUENCE: 145
VEIQGEVQTR                                                             10

SEQ ID NO: 146          moltype = AA   length = 14
FEATURE                 Location/Qualifiers
source                  1..14
                        mol_type = protein
                        organism = Gallus gallus
SEQUENCE: 146
VGATGEIFVV NSPR                                                        14

SEQ ID NO: 147          moltype = AA   length = 11
FEATURE                 Location/Qualifiers
source                  1..11
                        mol_type = protein
                        organism = Gallus gallus
SEQUENCE: 147
VSASGTTETL K                                                           11

SEQ ID NO: 148          moltype = AA   length = 9
FEATURE                 Location/Qualifiers
source                  1..9
                        mol_type = protein
                        organism = Gallus gallus
SEQUENCE: 148
VSTELVTGR                                                               9

SEQ ID NO: 149          moltype = AA   length = 16
FEATURE                 Location/Qualifiers
source                  1..16
                        mol_type = protein
                        organism = Gallus gallus
SEQUENCE: 149
WLLSAVSASG TTETLK                                                      16

SEQ ID NO: 150          moltype = AA   length = 8
FEATURE                 Location/Qualifiers
source                  1..8
                        mol_type = protein
                        organism = Gallus gallus
SEQUENCE: 150
```

```
YVIQEDRK                                                                  8

SEQ ID NO: 151        moltype = AA  length = 7875
FEATURE               Location/Qualifiers
source                1..7875
                      mol_type = protein
                      organism = Gallus gallus
SEQUENCE: 151
ATGGGCCCTG TGCGGCTCTT GCTGCTCTTG CTGCTGCTCA GCAGTGGTGT TCTCACACAG   60
GAAGGAACAC CTGAAAATGG AAACCCAGGA TGTTCAAAAG ATGCGGCCCG ATTTAAAAGC   120
CTTAGAAAAT ATGTTTACTT ATATGAAGCA GAAACATCAA GTGGGATCAC GGGAACAGCA   180
GATTCTCGAA GCGGTTCAAA GATCACCTGT AAAGTTGAGT TGGAGGTACC ACAGCTGTGC   240
CAGTTCATCC TGAGGACAAT GCATTGCTCC CTAAGGGAGA CATTTGGTGT TGACAGTGAG   300
AGAAGAGCCA TGCTGAGGAA GTCAAAGAAC TCTGATGACT TTGCAAATGC CATGTCCAAA   360
CATGAGCTAA GATTCAGCAC TCAGGATGGA ACAAAAGTTA AACTATATCC AGAGAAGGAT   420
GAACCTCTGA ATGTCCTCAA TCTCAAGAGA GGAATTATCT CAGCTCTCCT TGCACCAACA   480
GAAACAGAGG AAAACATAAA AACAATTTCC ATGGATACTG TATATGGAAA GTGTGACAGT   540
GAGGTTGAGT TCAAATCCAG AAGAGGAAGT GTTGCAGAAG ATATTTCAAT TAACAGGAAC   600
CTGAAAGCCT GTGACAACTT CAGTCCAATC AGAGATTATG TCAGCCCTGT TGCCATTGTA   660
AAAGGACTAA ACATCCCACT ATCTACCCTT CTGAGTAGCA CTCAATCCTG TCACTACAGT   720
ATTGATGCAA AGAAAAAGCA TATCAGAGAT GTTGTCTGCA GTGAAAAACA CCTGTTTCTG   780
CCTTCCTCAT ACAAAAATCA GTATGGTATG ATGACAGAAG TCAACCAGAC ACTGAAGCTT   840
GAAGATAATC AGAGGATGAA TAACAGAAAT CCTGATGGGA ATGAACTGGA AGAGAAAGGA   900
CTTGCACTGG AAAGCACAGA TGCTAAATTT TCCAGGCAGG GTGATGCTGT TTTGAAAATT   960
CTTCAGGAGC TGCAGAAACT TACTGCCTCC CAGCAGAACC AGCAGAGAGC AAAACTCTTT   1020
TACAAATTTG TTTCTGGACT TAGAAGTTTG CACAACAGCA CTCTTGGCTC TCTTGTACCA   1080
AAGATGATGG AAACTTCAAG TTCCATCACG ATTCAGGCCC TGATTCAGTG TGGGACTCCA   1140
GAGTGTTACA GTGCAGTCCT TCAGATACTG AGAACTGGAA ACGTAAATCC ACTTGTGGTA   1200
GACCTGGTCA CGTATACCCT GGGACTCTTG CCTTCTCCTA CTCCAAAGAG AATCCGGGAA   1260
ATTCTTAACA TGGCCCAGTA TCAGCCAAGC AGAGCTTCCT TTTATGGCTT GAGTCATGCT   1320
GTTACCAAGT CTATAATGA AGAGATGATT GTAACAGAGG AAATAACAGA TGTTGCTGAC   1380
TTCATGGTAT CACTGCTCGG CACTGACTGT TCTGGAGATG CTGAACTTAC ATATCTCACA   1440
CTTCGGGCTA TTGGAAACAT GGGTGCAGTA ATGGAGAAAG CTAAACCCAG CCTGAAAGCT   1500
TCTCTTAAAA CATGTATCAG AAATCAAGCT GCATCAGTTT CAGTTCAAAA AGCAGCCATA   1560
CAGGCATTCC GGAAAATGAC CATTACAAGA GAGGATCGTT CAGCACTTCT GAAAGAATTC   1620
CAGGAAGGGG ATGCACCTAC AGATAAACGT CTAGCAACCT ATCTCATACT GATGAAGAAT   1680
CCTTCCCCAG CTGATCTCGC AAAGATTATG AGAATCCTCA CAAGGGAGAA GAACGAGCAA   1740
GTGAAAAGCT TTGTCGCTTC ACACATTGCC AACATCCTAG ACTCTGGCTC AGTAGGCATT   1800
GAAGATCTAA AAAGCCATGT TGAAGAAGCA CTGAAAGGAA ATGAGGTTCC AACAGCCAAA   1860
GATTTCAGAA AATTCTCACA AAATTATCAA GTTTCCAAAA GAGTTTCTGT ACCTGGCCTC   1920
AATCCCATCT CTGCCAAAGT AGAAGGAAAT GTGATATTTG ATCCAAGCAG CTATGTTCCT   1980
AAAGAAACTA TGCTGAAAAC CACCCTGAAC TTGTATGGTT TTGGCCCAAG TGATATCTTT   2040
GAGCTTGGCT TGGATGGAAA GGGATTTGAA CCAACACTGG AAGCTTTGTT TGGAGAGAAG   2100
GGATTTTTCC CAGATACTGC AAGCAAGGCC CTGTATTGGG TTGATGGCAA AGTGCCAGAG   2160
CAGGTTTCCA AGGCTCTCTT TGACTACTTT GGTTACTCCC ACGATGGCAA GCAGGATCAG   2220
GAGATCACTA AAGCAGTAAT TCTTAACCTT GAAAAACTGA TAAAAGAATT GAGCAAGAAG   2280
GAAGCTCCTG AAGGAAGGGC ATTTCTGCGA ATCCTGGGAG AAGAGCTTGG GTACATGAAA   2340
CTCAGTGATT TCAAATTGCT GGGAAGCGTG GCTCTAGAGT GCATTAAAAC TCTTGAGAGA   2400
ATTCCTGAAA TAATTGCACA AGCCATCTCC AAAGGTGTTG ACAAGGACTT ATTTGTCCAC   2460
TATATGTTTA TGGACAATGA GTTTGAACTC CCAACTGGAG CAGGTTTGCA ACTGAAGTTT   2520
GCCTTGTCTG GAATAGTGAC ACCTGGGGCC AAAGTAGCTG TGAAACTTCA TCAAAAAAGT   2580
ATGCAAGCAG AACTCATTGC TAAACCTTCA GTAGCAGTTG AGTTTGTAAC ACATCTAGGA   2640
ATAAACATGC CTGAATTTGC TAGAAGTGGT GTGGAGATGA ATTCCAATAT ATTCCATGAG   2700
TCTGGAATTG AAGCACATGT TAGTGTGAAA GCTGGACAGC TGAAATTCAG CATTCCTGCC   2760
CCGAAGACCC CAACAAAACT CCTCAGTATC AGCAACAAC TTCATTTGGT GTCTCCAGCC   2820
AAAACTGAAG AGATTCCACC TCTGATTGAG AACCGAGAAT CTCAACTTC GTGCAAGCCT   2880
TTCATTTCTG TCTAAATTT CTGCACTAAA TTATTGTACT CTAATGCCAG TTCCATGGAG   2940
GCAGCTCCAT ATTATCCCTT GACTGGAGAA ACCAGATTTG AAGTTGAAAT AGTGTCCACA   3000
GGGGAAGTGA AAGAATACTC TGCAAGTGCA AACTATGATC TGCAGAGAGA GGGAACTGAC   3060
CTGGTAGACA CATTAAAGTT TGCGGTACGA GCAGAAGGTG TAAAGCAGCA TGAAGCCACA   3120
CTAACCTTTA AGTACAATAG AGACAGGAAG ATTCTGACCA GCGACGTCTC CATTCCAGAT   3180
GTTGATGTTG ACTTTGGTAC TAACTTCAGA ATCACTGATG AATCTGTTTC TGGGAAGAAA   3240
GCATATATCT TCGTTATAGA CTTTAATAAC AAGAAGATTT CTGAAGTCAC TCTCACTGGA   3300
CAAATAAGAT ATGCTGGAAT AGAAGAAGCA ATGCTGAGAG GCACCGTTTC TATTCCTCGT   3360
CTGCAAACTG AACTTAAAAC TGAAGCACTG GTTAATTATT CACCCACCAA AGGATACCTT   3420
CAGATGAGCT CATCTGTAGG AACCCATGGG AACACAGTTT CAAAAAGAGT TCTTCTCAGA   3480
TATGATTCTG AAAAAGCTGA GCTAGAGTGG AATTCAGGTG CCACTGCTGC TGTGGGAAGA   3540
ATGTCTTCTG CCTTCCAAGT TGACTTTTCA GACTACTCAA AGACTTTAGA GAAGTATGCC   3600
AACGAACTTC TGGATCGGAA AGTCGCTCTT ACAGATATGA CAATGCGACA TATTGTATCA   3660
CAATTTATTG TGGCAACCAA CACCTGGCTA CAAAAGGCAT CAAAGATGT CCCCTATGCC   3720
CAGACTCTAC AAGCCAAACT AAGTGGACTG CAGGAACTGA ACATTCAGAA GATTAAACTG   3780
CCTGTTATCA CCATTCCTGA AGAACTTTTC TGAAAAGTGT AAGGCCGGAT CAAATATAGC   3840
TTCAATAAGA ACAGTTTTCT AATTAATATT CCATTACCAT TTGGTGGAAG ATCGTCCCAT   3900
GACATAAGAG TGCCACAGAC TGTTAAAACA CCTCGTCTAG TAATAGAGTC TATGGGAATA   3960
AACATACCAT CACAGGAATA CAGAATGCCA ACATTTACTG TTCCAGAATC CTATCCTCTT   4020
CTTGTGCCTT TATTTGGTGC TTTAGAGGCC TCCGCCAGTG TGCACAGCAA CTATTACAAC   4080
TGGACAGCAG CATACACTTT GACAAATAGC AGCACAGAGA AACAGCCAG AATTGGAACT   4140
ACTTATGCTG TGAATGCTGA TTCTGTTTTT GAGCTACTAT CCTACAACAT GAAAGGTTCC   4200
GGAGAGGCAT CTTCTAGTAG AAATGGATTC ACTTGTGCAT ATGAAAATCA TCTGAAGCAC   4260
```

```
AGACTCTTAA CTTCAGATTT TAAAATGTCT AGGACAAAGA GTTATGAACC TACATCAGTT   4320
TCAAACTGTA CCATATTTCT AATGGCATCC AGTGCTCTGG GTCCTCAGCT TTCATTTTCC   4380
AGTGATGTTG TTTCTGAAAA GACAAATAAC ATGAATATTA ATAATGTCAG GATAGAAGGG   4440
CAACTGGAAG TGGCTTCTGT GTTTGCAAGA AGTGTTTACA CTATGTCAAG CTCATACAAT   4500
GAAAAGAGAC GAGTTTTAGA AGGGAAGTCA AATCTGAGGT TGGATTCTTC TTACCTTCAA   4560
GCTACCAATC ATCTATCCGG TAGATACACT GATGGTGTAT TTTCCATTAC TTCAGCTTCT   4620
GATGTACAAA ATGGACTATT AAAGAACACA GCTTCACTGA AGTATGAAAA TAGCCAGCTG   4680
AAAATAACAT CTGAAACAAA TGGAAGGTAT CTACATCTCG CAGCTGTCAA TAAACTTGAA   4740
TTCCTTTTGT CAAAGAAGAT GGCAGCACTT CGTTCTGACT ACCAAGCCAC TTACAAGCAA   4800
ACCCAATGTT ATGCCTTGTT CGCAGGTTCT CTCAATTCCC AGGATCTTGT TTTCAACACT   4860
GATTTCTCTC TGACTGATCA AAGGAATCGA GCTGCACATA AGTCATCACT CAATGTTAAT   4920
CAGTATGGTC TAGCCAGCAG TGCAACTACA AATGTACAGT TTAGTCCACT GACAATGCAG   4980
AGTGAAATGA ATGCTAAACT TGATACCTCT GGAGGCTCTG TGTCACTGTC ATCATCTGGG   5040
CGCTATGGAA AAAACAATGC AAAATTCAAT GTAGGTGGAA GAGTGAGCTT AACGGAAATA   5100
ACGCTGGGAA GCGAATATCA GAGTACAATT CTGGGTATGG ACAATAAACA TGTCTTAAAC   5160
TTCAGAATTA ATAAAGAAGG ACTCAAGTTT TCAAATAATT TGCAAGGGTC ATTAAAAGAG   5220
ATTAAGCTGG AGTACACAAA TGACTTGAAT ATTCCTGGCT TATCCCTAAC ATTTGTTTCA   5280
AAGTTAGACA ACAGCTTCAG CTTTGACAAG TTCCACAAGC ATGTTTTTGA CCTTCAGCTG   5340
CAGCCCAGAT CACTTACAGC TAAGCTGAAC AATAATATTA AATACACCAA AACTGAAGTT   5400
TCCAACAAAG CAGAACTGCT CCTTGAGCCT CTGAAGCTGA ACTTGGGTGG CAATGTGAGA   5460
GCAGCCTATG GAACAGATGA AGTAAGACAT ACCTACGCCA TTACATATGC TGATCTAACT   5520
GCAAACTTTA AAACAGACAC AGTTGCAAAT GTCCAAGGTG CAGCAGTGAG TCACAGAGTT   5580
AATCTGAATG TGGCAGGACT GGCTTCCTCC ATTACTATGA ACACAAATTG TGATTCCAAA   5640
TCTCTCCGTT TCAGCAATGC TCTGCGTTCC ACTATGGCCC CATTCACTAT CACGGCTGAT   5700
GTTCACACCA ACGGTAATGG GAAGCTGATT GCTCTGGGTG AACATACAGG AGACCTTTAC   5760
AGCAAAATCC TGTTCAAAGC AGAACCTCTT GCTTTCACTT TCTCCCATGA TTACAGAGGA   5820
TCTACCAGTC ATAGCTTCAA GTCTATGAGA AGATACTCTA CCAGCTTGA TAACAAATTT   5880
CATATGCTTT TTACTCCATC AGAGCAGTCG AGTGCTTGGA AATTGAAAAG TCAGCTAAAC   5940
AACAACATAT ATTCACAAGA TATCAATGCT TACAATGATG CAGAAAAGAT TGGTGTGGAA   6000
CTTAGTGGAA GAGCTTTAGC AGATCTCTCT GTGGTGGATA CAGCAATCAG ACTACCATTC   6060
ATGTCTGAAG AAGTTAATGT AATTGATGTA TTAGGCCTCA GGGACAGTGT GTCAGAGCTC   6120
CAAGAATTCA GCATCTCTGG CTCTGTGAAG TATGACAAAA ATAAAGATAT GCATGTTATT   6180
AACCTACCAT TCTTGGAACA CTTTCCAGTC TACTTTGAAC AAATCAGAGG TGCCATTCTA   6240
TCCACACTGC AGGCTGTACA GAATTACCTG AAAAACATTG ACGTAGATCA ATATATGAAA   6300
AAATACAAGG CAACTTTAGA TGAATTCCCA CAGCACCTTA ATGATTACAT GGACAAATTA   6360
GATCTGAAAG GCAGAGCTAG CACCCATAAAA ACTAATTTGA TTGCTTTCAC GAAGGACTAT   6420
AGAATAACAT CTGATGATCT CGAAATTATT CTGGAAAAAG CCCTGGATAA TCTTCAAGAA   6480
ATACTGCTCC AGCTTCAAGT TTATCTTGTG CAAATAGAGC AGTACATCAA AGAGAATTAC   6540
GATCAGTTTG ACATTAATGC ACTTATTGCA CAACTTCTTG ACAAAATAGT TGAAAAAATG   6600
ACAGCTCTAG ATGAAAAATA TAAGATAAGA GTGACTGTAG TTGACACTAT TCAGAAGTTA   6660
CAATTTTTTT TAAATCAATA TTACCCCAGC AACATTGGAA GCAACACTAT GACTTGGATT   6720
AAAAATATAG ATGATGAGTA TAGGATCACA GGTAGAATAA AGGAGAACCT AGAACAGCTC   6780
AAGATTCAGA TTCAGAACAT TGATATCAGA AGCTTTGCAG AAAATTTGAA AAGGAAGATT   6840
AAAATAATTG ATGTTAAACA ACTATTAGAA AAATTAAAGC GTTCATTACC AATTAAAAAA   6900
ATGAAGGAAG TTCTTGAACA AATCAAAGAC TTTATTCTGA GTTGGATGGA GGAGTACGAA   6960
GTGTCTGAGA AGATCAGTGC TTTCCGAGGT CATATGCATA AACTGATTGT AAAAATATGAA   7020
ATTGATAAGC ATGTGTATTT TTTATTGGAC AGAATGATAG ACTACTTAA CCAGTACAGA   7080
ATAAGAGAAA CGGTACGGAA AATGACGACC TACCTAAGAA AAATTGACGT GAAGACATGC   7140
TTTGACAAAA TTGTGTCTTT AATTGATGAT GCTGTGAAGA AAGTGCAAAC CTTTGATTAT   7200
GAAATGATGA TAAAGAAACT CAACAAATTC CTTGACATGA TTATAAAGAA ACTCAAATCT   7260
TTTGACTATA ACCAGTTTGT TGATGACACA AATAACAAAA TCCAAGAAAT TATACAGAAA   7320
ATAAATGAGG AACTCAGAAA TCTAGAACTG CCACAGAAAG CAGAAGCATT GAAACAGTAT   7380
ATGAGAGATT TTAATGCTGT AGTTTCAAAA TACGTAGAAC AACTAAGGGA CACCAAGCTT   7440
GTCGCTAAA TTAACTGGCT CAAGGAGCTC ATCGACTCAA CAACATTTAC TAATCTGAAA   7500
GCCAAAGTAA ATGAGCATCT GGAAGGTCTG CGAGAGAGAA TTTCTGACAT GGATATCGCC   7560
AAGGAATTTG AATGGTATCT TCAAAAGATA AGCCAGTTCT ACAATTCTGT TGTCATATAC   7620
ATTTCTGAAC AGTGGAACAT AGCTTTTAAA AAAATCGTTA CTTTGGCTGA GAAGTATGAC   7680
CTAAAAAATT GGGCTGAAAA TTTAAACCAG TTCATTGAAA CAGGATTTAA AGTCCCTGAA   7740
ATAAGAACAG TTATAGTCAC TATACCTGCC TTTGAATTCA GTCTTCGAAG TCTTCGGGAA   7800
GCAACTTTCC GAACACCGGA CTTCATTGTT CCACTGACTG ATCTGAAAAT CCCCTCCTAT   7860
GAAATAAATA TTAGG                                                     7875
```

```
SEQ ID NO: 152          moltype = AA  length = 2625
FEATURE                 Location/Qualifiers
source                  1..2625
                        mol_type = protein
                        organism = Gallus gallus
SEQUENCE: 152
MGPVRLLLLL LLLSSGVLTQ EGTPENGNPG CSKDAARFKS LRKYVYLYEA ETSSGITGTA   60
DSRSGSKITC KVELEVPQLC QFILRTMHCS LRETFGVDSE RRAMLRKSKN SDDFANAMSK   120
HELRFSTQDG TKVKLYPEKD EPLNVLNLKR GIISALLAPT ETEENIKTIS MDTVYGKCDS   180
EVEFKSRRGS VAEDISINRN LKACDNFSPI RDYVSPVAIV KGLNIPLSTL LSSTQSCHYS   240
IDAKKKHIRD VVCSEKHLFL PSSYKNQYGM MTEVNQTLKL EDNQRMNNRN PDGDELEEKG   300
LALESTDAKF SRQGDAVLKI LQELQKLTAS QQNQQRAKLF YKFVSGLRSL HNSTLGSLVP   360
KMMETSSSIT IQALIQCGTP ECYSAVLQIL RTGNVNPLVV DLVTYTLGLL PSPTPKRIRE   420
ILNMAQYQPS RASFYGLSHA VTKFYNEKMI VTEEITDVAD FMVSLLGTDC SGDAELTYLT   480
LRAIGNMGAV MEKAKPSLKA SLKTCIRNQA ASLSVQKAAI QAFRKMTITE EDRSALLKEF   540
QEGDAPTDKR LATYLILMKN PSPADLAKIM RILTREKNEQ VKSFVASHIA NILDSDEVGI   600
EDLKSHVEEA LKGNEVPTAK DFRKFSQNYQ VSKRVSVPGL NPISAKVEGN VIFDPSSYVP   660
```

```
KETMLKTTLN LYGFGPSDIF ELGLDGKGFE PTLEALFGEK GFFPDTASKA LYWVDGKVPE    720
QVSKALFDYF GYSHDGKQDQ EITKAVILNL EKLIKELSKK EAPEGRAFLR ILGEELGYMK    780
LSDFKLLGSV ALECIKTLQR IPEIIAQAIS KGVDKDLFVH YMFMDNEFEL PTGAGLQLKF    840
ALSGIVTPGA KVAVKLHQKS MQAELIAKPS VAVEFVTHLG INMPEFARSG VEMNSNIFHE    900
SGIEAHVSVK AGQLKFSIPA PKTPTKLLSI SNTLHLVSPA KTEEIPPLIE NREFSTSCKP    960
FISGLNFCTK LLYSNASSME AAPYYPLTGE TRFEVEIVST GEVKEYSASA NYDLQREGTD   1020
LVDTLKFAVQ AEGVKQHEAT LTFKYNRDRK ILTSDVSIPD VDVDFGTNFR ITDESVSGKK   1080
AYIFVIDFNN KKISEVTLTG QIRYAGIEEA MLRGTVSIPR LQTELKTEAL VNYSPTKGYL   1140
QMSSSVGTHG NTVSKRVLLR YDSEKAELEW NSGATAAVGR MSSAFQVDFS DYSKTLEKYA   1200
NELLDRKVAL TDMTMRHIVS QFIVATNTWL QKASKDVPYA QTLQAKLSGL QELNIQKIKL   1260
PVITIPEELF LKSEGRIKYS FNKNSFLINI PLPFGGRSSH DIRVPQTVKT PRLVIESMGI   1320
NIPSQEYRMP TFTVPESYPL LVPLFGALEA SASVHSNYYN WTAAYTLTNS STEKTARIGT   1380
TYAVNADSVF ELLSYNMKGS GEASSSRNGF TCAYENHLKH RLLTSDFKMS RTKSYEPTSV   1440
SNCTIFLMAS SALGPQLSFS SDVVSEKTNN MNINNVRIEG QLEVASVFAR SVYTMSSSYN   1500
EKRRVLEGKS NLRLDSSYLQ ATNHLSGRYT DGVFSITSAS DVQNGLLKNT ASLKYENSQL   1560
KITSETNGRY LHLAAVNKLE FLLSKKMAAL RSEYQATYKQ TQCYALFAGS LNSQDLVFNT   1620
DFSLTDQRNR AAHKSSLNVN QYGLASSATT NVQFSPLTMQ SEMNAKLDTS GGSVSLSSSG   1680
RYGKNNAKFN VGGRVSLTEI TLGSEYQSTI LGMDNKHVLN FRINKEGLKF SNNLQGSLKE   1740
IKLEYTNDLN IPGLSLTFVS KLDNSFSFDK FHKHVFDLQL QPRSLTAKLN NNIKYTKTEV   1800
SNKAELLLEP LKLNLGGNVR AAYGTDEVRH TYAITYADLT ANFKTDTVAN VQGAAVSHRV   1860
NLNVAGLASS ITMNTNCDSK SLRFSNALRS TMAPFTITAD VHTNGNGKLI ALGEHTGDLY   1920
SKILFKAEPL AFTFSHDYRG STSHSFKSMR RYSTQLDNKF HMLFTPSEQS SAWKLKSQLN   1980
NNIYSQDINA YNDAEKIGVE LSGRALADLS VVDTAIRLPF MSEEVNVIDV LGLRDSVSEP   2040
QEFSISGSVK YDKNKDMHVI NLPFLEHFPV YFEQIRGAIL STLQAVQNYL KNIDVDQYMK   2100
KYKATLDEFP QHLNDYMDKL DLKGRASTIK TNLIAFTKDY RITSDDLEII LEKALDNLQE   2160
ILLQLQVYLV QIEQYIKENY DQFDINALIA QLLDKIVEKM TALDEKYKIR VTVVDTIQKL   2220
QFFLNQYYPS NIGSNTMTWI KNIDDEYRIT GRIKENLEQL KIQIQNIDIR SFAENLKRKI   2280
KIIDVKQLLE KLKRSLPIKK MKEVLEQIKD FILSWMEEYE VSEKISAFRG HMHKLIVKYE   2340
IDKHVYFLLD RMIELLNQYR IRETVRKMTT YLRKIDVKTC FDKIVSLIDD AVKKVQTFDY   2400
EMMIKKLNKF LDMIIKKLKS FDYNQFVDDT NNKIQEIIQK INEELRNLEL PQKAEALKQY   2460
MRDFNAVVSK YVEQLRDTKL VAIINWLKEL IDSTTFTNLK AKVNEHLEGL RERISDMDIA   2520
KEFEWYLQKI SQFYNSVVIY ISEQWNIAFK KIVTLAEKYD LKNWAENLNQ FIETGFKVPE   2580
IRTVIVTIPA FEFSLRSLRE ATFRTPDFIV PLTDLKIPSY EINIR                  2625
```

```
SEQ ID NO: 153              moltype = AA   length = 9
FEATURE                     Location/Qualifiers
source                      1..9
                            mol_type = protein
                            organism = Gallus gallus
SEQUENCE: 153
AAYGTDEVR                                                             9

SEQ ID NO: 154              moltype = AA   length = 15
FEATURE                     Location/Qualifiers
source                      1..15
                            mol_type = protein
                            organism = Gallus gallus
SEQUENCE: 154
AELEWNSGAT AAVGR                                                      15

SEQ ID NO: 155              moltype = AA   length = 9
FEATURE                     Location/Qualifiers
source                      1..9
                            mol_type = protein
                            organism = Gallus gallus
SEQUENCE: 155
AELLLEPLK                                                             9

SEQ ID NO: 156              moltype = AA   length = 8
FEATURE                     Location/Qualifiers
source                      1..8
                            mol_type = protein
                            organism = Gallus gallus
SEQUENCE: 156
AEPLAFTF                                                              8

SEQ ID NO: 157              moltype = AA   length = 12
FEATURE                     Location/Qualifiers
source                      1..12
                            mol_type = protein
                            organism = Gallus gallus
SEQUENCE: 157
AITYADLTAN FK                                                         12

SEQ ID NO: 158              moltype = AA   length = 13
FEATURE                     Location/Qualifiers
source                      1..13
                            mol_type = protein
                            organism = Gallus gallus
```

-continued

```
SEQUENCE: 158
ALADLSVVDT AIR                                                    13

SEQ ID NO: 159         moltype = AA   length = 11
FEATURE                Location/Qualifiers
source                 1..11
                       mol_type = protein
                       organism = Gallus gallus SEQUENCE: 159
ALSGIVTPGA K                                                     11

SEQ ID NO: 160         moltype = AA   length = 12
FEATURE                Location/Qualifiers
source                 1..12
                       mol_type = protein
                       organism = Gallus gallus SEQUENCE: 160
ASFYGLSHAV TK                                                    12

SEQ ID NO: 161         moltype = AA   length = 8
FEATURE                Location/Qualifiers
source                 1..8
                       mol_type = protein
                       organism = Gallus gallus SEQUENCE: 161
ATLDEFPQ                                                          8

SEQ ID NO: 162         moltype = AA   length = 8
FEATURE                Location/Qualifiers
source                 1..8
                       mol_type = protein
                       organism = Gallus gallus SEQUENCE: 162
AVILNLEK                                                          8

SEQ ID NO: 163         moltype = AA   length = 11
FEATURE                Location/Qualifiers
source                 1..11
                       mol_type = protein
                       organism = Gallus gallus SEQUENCE: 163
AYTFVIDFNN K                                                     11

SEQ ID NO: 164         moltype = AA   length = 10
FEATURE                Location/Qualifiers
source                 1..10
                       mol_type = protein
                       organism = Gallus gallus SEQUENCE: 164
DEPLNVLNLK                                                       10

SEQ ID NO: 165         moltype = AA   length = 8
FEATURE                Location/Qualifiers
source                 1..8
                       mol_type = protein
                       organism = Gallus gallus SEQUENCE: 165
DFNAVVSK                                                          8

SEQ ID NO: 166         moltype = AA   length = 7
FEATURE                Location/Qualifiers
source                 1..7
                       mol_type = protein
                       organism = Gallus gallus SEQUENCE: 166
DLQLQPR                                                           7

SEQ ID NO: 167         moltype = AA   length = 16
FEATURE                Location/Qualifiers
source                 1..16
                       mol_type = protein
                       organism = Gallus gallus SEQUENCE: 167
DSVSEPQEFS ISGSVK                                                16

SEQ ID NO: 168         moltype = AA   length = 11
FEATURE                Location/Qualifiers
source                 1..11
                       mol_type = protein
```

-continued

```
                                organism = Gallus gallus
SEQUENCE: 168
DVPYAQTLQA K                                                              11

SEQ ID NO: 169         moltype = AA   length = 10
FEATURE                Location/Qualifiers
source                 1..10
                       mol_type = protein
                       organism = Gallus gallus
SEQUENCE: 169
DYVSPVAIVK                                                                10

SEQ ID NO: 170         moltype = AA   length = 11
FEATURE                Location/Qualifiers
source                 1..11
                       mol_type = protein
                       organism = Gallus gallus
SEQUENCE: 170
EFQEGDAPTD K                                                              11

SEQ ID NO: 171         moltype = AA   length = 10
FEATURE                Location/Qualifiers
source                 1..10
                       mol_type = protein
                       organism = Gallus gallus
SEQUENCE: 171
EGTDLVDTLK                                                                10

SEQ ID NO: 172         moltype = AA   length = 14
FEATURE                Location/Qualifiers
source                 1..14
                       mol_type = protein
                       organism = Gallus gallus
SEQUENCE: 172
ELEWNSGATA AVGR                                                           14

SEQ ID NO: 173         moltype = AA   length = 9
FEATURE                Location/Qualifiers
source                 1..9
                       mol_type = protein
                       organism = Gallus gallus
SEQUENCE: 173
ETFGVDSER                                                                 9

SEQ ID NO: 174         moltype = AA   length = 12
FEATURE                Location/Qualifiers
source                 1..12
                       mol_type = protein
                       organism = Gallus gallus
SEQUENCE: 174
EYSASANYDL QR                                                             12

SEQ ID NO: 175         moltype = AA   length = 12
FEATURE                Location/Qualifiers
source                 1..12
                       mol_type = protein
                       organism = Gallus gallus
SEQUENCE: 175
FALSGIVTPG AK                                                             12

SEQ ID NO: 176         moltype = AA   length = 9
FEATURE                Location/Qualifiers
source                 1..9
                       mol_type = protein
                       organism = Gallus gallus
SEQUENCE: 176
FAVQAEGVK                                                                 9

SEQ ID NO: 177         moltype = AA   length = 12
FEATURE                Location/Qualifiers
source                 1..12
                       mol_type = protein
                       organism = Gallus gallus
SEQUENCE: 177
FEVEIVSTGE VK                                                             12

SEQ ID NO: 178         moltype = AA   length = 10
FEATURE                Location/Qualifiers
source                 1..10
```

```
                         mol_type = protein
                         organism = Gallus gallus
SEQUENCE: 178
FSNNLQGSLK                                                                    10

SEQ ID NO: 179           moltype = AA   length = 9
FEATURE                  Location/Qualifiers
source                   1..9
                         mol_type = protein
                         organism = Gallus gallus
SEQUENCE: 179
FSQNYQVSK                                                                     9

SEQ ID NO: 180           moltype = AA   length = 13
FEATURE                  Location/Qualifiers
source                   1..13
                         mol_type = protein
                         organism = Gallus gallus
SEQUENCE: 180
GFEPTLEALF GEK                                                                13

SEQ ID NO: 181           moltype = AA   length = 9
FEATURE                  Location/Qualifiers
source                   1..9
                         mol_type = protein
                         organism = Gallus gallus
SEQUENCE: 181
GFFPDTASK                                                                     9

SEQ ID NO: 182           moltype = AA   length = 17
FEATURE                  Location/Qualifiers
source                   1..17
                         mol_type = protein
                         organism = Gallus gallus
SEQUENCE: 182
GIISALLAPT ETEENIK                                                            17

SEQ ID NO: 183           moltype = AA   length = 10
FEATURE                  Location/Qualifiers
source                   1..10
                         mol_type = protein
                         organism = Gallus gallus
SEQUENCE: 183
GLALESTDAK                                                                    10

SEQ ID NO: 184           moltype = AA   length = 11
FEATURE                  Location/Qualifiers
source                   1..11
                         mol_type = protein
                         organism = Gallus gallus
SEQUENCE: 184
GSVAEDISIN R                                                                  11

SEQ ID NO: 185           moltype = AA   length = 13
FEATURE                  Location/Qualifiers
source                   1..13
                         mol_type = protein
                         organism = Gallus gallus
SEQUENCE: 185
IEGQLEVASV FAR                                                                13

SEQ ID NO: 186           moltype = AA   length = 8
FEATURE                  Location/Qualifiers
source                   1..8
                         mol_type = protein
                         organism = Gallus gallus
SEQUENCE: 186
IGVELSGR                                                                      8

SEQ ID NO: 187           moltype = AA   length = 15
FEATURE                  Location/Qualifiers
source                   1..15
                         mol_type = protein
                         organism = Gallus gallus
SEQUENCE: 187
IKLPVITIPE ELFLK                                                              15

SEQ ID NO: 188           moltype = AA   length = 7
FEATURE                  Location/Qualifiers
```

-continued

```
source                    1..7
                          mol_type = protein
                          organism = Gallus gallus
SEQUENCE: 188
ILQELQK                                                                            7

SEQ ID NO: 189            moltype = AA   length = 20
FEATURE                   Location/Qualifiers
source                    1..20
                          mol_type = protein
                          organism = Gallus gallus
SEQUENCE: 189
ILTSDVSIPD VDVDFGTNFR                                                              20

SEQ ID NO: 190            moltype = AA   length = 11
FEATURE                   Location/Qualifiers
source                    1..11
                          mol_type = protein
                          organism = Gallus gallus
SEQUENCE: 190
IPEIIAQAIS K                                                                       11

SEQ ID NO: 191            moltype = AA   length = 9
FEATURE                   Location/Qualifiers
source                    1..9
                          mol_type = protein
                          organism = Gallus gallus
SEQUENCE: 191
IPSYEINIR                                                                          9

SEQ ID NO: 192            moltype = AA   length = 11
FEATURE                   Location/Qualifiers
source                    1..11
                          mol_type = protein
                          organism = Gallus gallus
SEQUENCE: 192
ISEVTLTGQI R                                                                       11

SEQ ID NO: 193            moltype = AA   length = 9
FEATURE                   Location/Qualifiers
source                    1..9
                          mol_type = protein
                          organism = Gallus gallus
SEQUENCE: 193
ITDESVSGK                                                                          9

SEQ ID NO: 194            moltype = AA   length = 10
FEATURE                   Location/Qualifiers
source                    1..10
                          mol_type = protein
                          organism = Gallus gallus
SEQUENCE: 194
KFSQNYQVSK                                                                         10

SEQ ID NO: 195            moltype = AA   length = 12
FEATURE                   Location/Qualifiers
source                    1..12
                          mol_type = protein
                          organism = Gallus gallus
SEQUENCE: 195
KISEVTLTGQ IR                                                                      12

SEQ ID NO: 196            moltype = AA   length = 11
FEATURE                   Location/Qualifiers
source                    1..11
                          mol_type = protein
                          organism = Gallus gallus
SEQUENCE: 196
LAPTETEENI K                                                                       11

SEQ ID NO: 197            moltype = AA   length = 9
FEATURE                   Location/Qualifiers
source                    1..9
                          mol_type = protein
                          organism = Gallus gallus
SEQUENCE: 197
LDNSFSFDK                                                                          9

SEQ ID NO: 198            moltype = AA   length = 15
```

-continued

```
FEATURE              Location/Qualifiers
source               1..15
                     mol_type = protein
                     organism = Gallus gallus
SEQUENCE: 198
LDSSYLQATN HLSGR                                                    15

SEQ ID NO: 199       moltype = AA  length = 15
FEATURE              Location/Qualifiers
source               1..15
                     mol_type = protein
                     organism = Gallus gallus
SEQUENCE: 199
LDTSGGSVSL SSSGR                                                    15

SEQ ID NO: 200       moltype = AA  length = 19
FEATURE              Location/Qualifiers
source               1..19
                     mol_type = protein
                     organism = Gallus gallus
SEQUENCE: 200
LEYTNDLNIP GLSLTFVSK                                                19

SEQ ID NO: 201       moltype = AA  length = 7
FEATURE              Location/Qualifiers
source               1..7
                     mol_type = protein
                     organism = Gallus gallus
SEQUENCE: 201
LLTSDFK                                                             7

SEQ ID NO: 202       moltype = AA  length = 8
FEATURE              Location/Qualifiers
source               1..8
                     mol_type = protein
                     organism = Gallus gallus
SEQUENCE: 202
LNLGGNVR                                                            8

SEQ ID NO: 203       moltype = AA  length = 13
FEATURE              Location/Qualifiers
source               1..13
                     mol_type = protein
                     organism = Gallus gallus
SEQUENCE: 203
LPVITIPEEL FLK                                                      13

SEQ ID NO: 204       moltype = AA  length = 11
FEATURE              Location/Qualifiers
source               1..11
                     mol_type = protein
                     organism = Gallus gallus
SEQUENCE: 204
LSFSSDVVSE K                                                        11

SEQ ID NO: 205       moltype = AA  length = 11
FEATURE              Location/Qualifiers
source               1..11
                     mol_type = protein
                     organism = Gallus gallus
SEQUENCE: 205
LSGLQELNIQ K                                                        11

SEQ ID NO: 206       moltype = AA  length = 17
FEATURE              Location/Qualifiers
source               1..17
                     mol_type = protein
                     organism = Gallus gallus
SEQUENCE: 206
LYGFGPSDIF ELGLDGK                                                  17

SEQ ID NO: 207       moltype = AA  length = 15
FEATURE              Location/Qualifiers
source               1..15
                     mol_type = protein
                     organism = Gallus gallus
SEQUENCE: 207
LYPEKDEPLN VLNLK                                                    15
```

-continued

```
SEQ ID NO: 208            moltype = AA   length = 7
FEATURE                   Location/Qualifiers
source                    1..7
                          mol_type = protein
                          organism = Gallus gallus
SEQUENCE: 208
NIDDEYR                                                             7

SEQ ID NO: 209            moltype = AA   length = 10
FEATURE                   Location/Qualifiers
source                    1..10
                          mol_type = protein
                          organism = Gallus gallus
SEQUENCE: 209
NPDGDELEEK                                                          10

SEQ ID NO: 210            moltype = AA   length = 9
FEATURE                   Location/Qualifiers
source                    1..9
                          mol_type = protein
                          organism = Gallus gallus
SEQUENCE: 210
NPSPADLAK                                                           9

SEQ ID NO: 211            moltype = AA   length = 10
FEATURE                   Location/Qualifiers
source                    1..10
                          mol_type = protein
                          organism = Gallus gallus
SEQUENCE: 211
NQAASLSVQK                                                          10

SEQ ID NO: 212            moltype = AA   length = 14
FEATURE                   Location/Qualifiers
source                    1..14
                          mol_type = protein
                          organism = Gallus gallus
SEQUENCE: 212
NSFLINIPLP FGGR                                                     14

SEQ ID NO: 213            moltype = AA   length = 9
FEATURE                   Location/Qualifiers
source                    1..9
                          mol_type = protein
                          organism = Gallus gallus
SEQUENCE: 213
QVDFSDYSK                                                           9

SEQ ID NO: 214            moltype = AA   length = 12
FEATURE                   Location/Qualifiers
source                    1..12
                          mol_type = protein
                          organism = Gallus gallus
SEQUENCE: 214
RGSVAEDISI NR                                                       12

SEQ ID NO: 215            moltype = AA   length = 13
FEATURE                   Location/Qualifiers
source                    1..13
                          mol_type = protein
                          organism = Gallus gallus
SEQUENCE: 215
RVSVPGLNPI SAK                                                      13

SEQ ID NO: 216            moltype = AA   length = 10
FEATURE                   Location/Qualifiers
source                    1..10
                          mol_type = protein
                          organism = Gallus gallus
SEQUENCE: 216
SASANYDLQR                                                          10

SEQ ID NO: 217            moltype = AA   length = 8
FEATURE                   Location/Qualifiers
source                    1..8
                          mol_type = protein
                          organism = Gallus gallus
SEQUENCE: 217
SEYQATYK                                                            8
```

-continued

```
SEQ ID NO: 218            moltype = AA   length = 9
FEATURE                   Location/Qualifiers
source                    1..9
                          mol_type = protein
                          organism = Gallus gallus
SEQUENCE: 218
SFVASHIAN                                                          9

SEQ ID NO: 219            moltype = AA   length = 9
FEATURE                   Location/Qualifiers
source                    1..9
                          mol_type = protein
                          organism = Gallus gallus
SEQUENCE: 219
SGIVTPGAK                                                          9

SEQ ID NO: 220            moltype = AA   length = 12
FEATURE                   Location/Qualifiers
source                    1..12
                          mol_type = protein
                          organism = Gallus gallus
SEQUENCE: 220
SQDINAYNDA EK                                                      12

SEQ ID NO: 221            moltype = AA   length = 20
FEATURE                   Location/Qualifiers
source                    1..20
                          mol_type = protein
                          organism = Gallus gallus
SEQUENCE: 221
SQLNNNIYSQ DINAYNDAEK                                              20

SEQ ID NO: 222            moltype = AA   length = 15
FEATURE                   Location/Qualifiers
source                    1..15
                          mol_type = protein
                          organism = Gallus gallus
SEQUENCE: 222
TDTVANVQGA AVSHR                                                   15

SEQ ID NO: 223            moltype = AA   length = 11
FEATURE                   Location/Qualifiers
source                    1..11
                          mol_type = protein
                          organism = Gallus gallus
SEQUENCE: 223
TEALVNYSPT K                                                       11

SEQ ID NO: 224            moltype = AA   length = 11
FEATURE                   Location/Qualifiers
source                    1..11
                          mol_type = protein
                          organism = Gallus gallus
SEQUENCE: 224
TEEIPPLIEN R                                                       11

SEQ ID NO: 225            moltype = AA   length = 14
FEATURE                   Location/Qualifiers
source                    1..14
                          mol_type = protein
                          organism = Gallus gallus
SEQUENCE: 225
TGNVNPLVVD LVTY                                                    14

SEQ ID NO: 226            moltype = AA   length = 25
FEATURE                   Location/Qualifiers
source                    1..25
                          mol_type = protein
                          organism = Gallus gallus
SEQUENCE: 226
TGNVNPLVVD LVTYTLGLLP SPTPK                                        25

SEQ ID NO: 227            moltype = AA   length = 12
FEATURE                   Location/Qualifiers
source                    1..12
                          mol_type = protein
                          organism = Gallus gallus
SEQUENCE: 227
```

-continued

```
TPDFIVPLTD LK                                                    12

SEQ ID NO: 228          moltype = AA  length = 21
FEATURE                 Location/Qualifiers
source                  1..21
                        mol_type = protein
                        organism = Gallus gallus
SEQUENCE: 228
TTLNLYGFGP SDIFELGLDG K                                          21

SEQ ID NO: 229          moltype = AA  length = 15
FEATURE                 Location/Qualifiers
source                  1..15
                        mol_type = protein
                        organism = Gallus gallus
SEQUENCE: 229
VEGNVIFDPS SYVPK                                                 15

SEQ ID NO: 230          moltype = AA  length = 9
FEATURE                 Location/Qualifiers
source                  1..9
                        mol_type = protein
                        organism = Gallus gallus
SEQUENCE: 230
VFDLQLQPR                                                        9

SEQ ID NO: 231          moltype = AA  length = 10
FEATURE                 Location/Qualifiers
source                  1..10
                        mol_type = protein
                        organism = Gallus gallus
SEQUENCE: 231
VNLNVAGLAS                                                       10

SEQ ID NO: 232          moltype = AA  length = 12
FEATURE                 Location/Qualifiers
source                  1..12
                        mol_type = protein
                        organism = Gallus gallus
SEQUENCE: 232
VSVPGLNPIS AK                                                    12

SEQ ID NO: 233          moltype = AA  length = 9
FEATURE                 Location/Qualifiers
source                  1..9
                        mol_type = protein
                        organism = Gallus gallus
SEQUENCE: 233
VTVVDTIQK                                                        9

SEQ ID NO: 234          moltype = AA  length = 8
FEATURE                 Location/Qualifiers
source                  1..8
                        mol_type = protein
                        organism = Gallus gallus
SEQUENCE: 234
YANELLDR                                                         8

SEQ ID NO: 235          moltype = AA  length = 8
FEATURE                 Location/Qualifiers
source                  1..8
                        mol_type = protein
                        organism = Gallus gallus
SEQUENCE: 235
YSTQLDNK                                                         8

SEQ ID NO: 236          moltype = DNA  length = 927
FEATURE                 Location/Qualifiers
source                  1..927
                        mol_type = other DNA
                        organism = Gallus gallus
SEQUENCE: 236
atgggccctg tgcggctctt gctgctcttg ctgctgctca gcagtggtgt tctcacacag  60
gaaggaacac ctgaaaatgg aaacccagga tgttcaaaag atgcggcccg atttaaaagc  120
cttagaaaat atgtttactt atatgaagca gaaacatcaa gtgggatcac gggaacagca  180
gattctcgaa gcggttcaaa gatcacctgt aaagttgagt tggaggtacc acagctgtgc  240
cagttcatcc tgaggacaat gcattgctcc ctaagggaga catttggtgt tgacagtgag  300
agaagagcca tgctgaggaa gtcaaagaac tctgatgact ttgcaaatgc catgtccaaa  360
catgagctaa gattcagcac tcaggatgga acaaaagtta aactatatcc agagaaggat  420
```

```
gaacctctga atgtcctcaa tctcaagaga ggaattatct cagctctcct tgcaccaaca   480
gaaacagagg aaaacataaa aacaatttcc atggatactg tatatggaaa gtgtgacagt   540
gaggttgagt tcaaatccag aagaggaagt gttgcagaag atatttcaat taacaggaac   600
ctgaaagcct gtgacaactt cagtccaatc agagattatg tcagccctgt tgccattgta   660
aaaggactaa acatcccact atctaccctt ctgagtagca ctcaatcctg tcactacagt   720
attgatgcaa agaaaaagca tatcagagat gttgtctgca gtgaaaaaca cctgtttctg   780
ccttcctcat acaaaaatca gtatggtatg atgacagaag tcaaccagac actgaagctt   840
gaagataatc agaggatgaa taacagaaat cctgatggag atgaactgga agagaaagga   900
cttgcactgg aaagcacaga tgctaaa                                       927
```

```
SEQ ID NO: 237        moltype = AA   length = 309
FEATURE               Location/Qualifiers
source                1..309
                      mol_type = protein
                      organism = Gallus gallus
SEQUENCE: 237
MGPVRLLLLL LLLSSGVLTQ EGTPENGNPG CSKDAARFKS LRKYVYLYEA ETSSGITGTA   60
DSRSGSKITC KVELEVPQLC QFILRTMHCS LRETFGVDSE RRAMLRKSKN SDDFANAMSK  120
HELRFSTQDG TKVKLYPEKD EPLNVLNLKR GIISALLAPT ETEENIKTIS MDTVYGKCDS  180
EVEFKSRRGS VAEDISINRN LKACDNFSPI RDYVSPVAIV KGLNIPLSTL LSSTQSCHYS  240
IDAKKKHIRD VVCSEKHLFL PSSYKNQYGM MTEVNQTLKL EDNQRMNNRN PDGDELEEKG  300
LALESTDAK                                                          309
```

```
SEQ ID NO: 238        moltype = AA   length = 13
FEATURE               Location/Qualifiers
source                1..13
                      mol_type = protein
                      organism = Gallus gallus
SEQUENCE: 238
ALLAPTETEE NIK                                                       13
```

```
SEQ ID NO: 239        moltype = AA   length = 10
FEATURE               Location/Qualifiers
source                1..10
                      mol_type = protein
                      organism = Gallus gallus
SEQUENCE: 239
DYVSPVAIVK                                                           10
```

```
SEQ ID NO: 240        moltype = AA   length = 9
FEATURE               Location/Qualifiers
source                1..9
                      mol_type = protein
                      organism = Gallus gallus
SEQUENCE: 240
ETFGVDSER                                                             9
```

```
SEQ ID NO: 241        moltype = AA   length = 17
FEATURE               Location/Qualifiers
source                1..17
                      mol_type = protein
                      organism = Gallus gallus
SEQUENCE: 241
GIISALLAPT ETEENIK                                                   17
```

```
SEQ ID NO: 242        moltype = AA   length = 11
FEATURE               Location/Qualifiers
source                1..11
                      mol_type = protein
                      organism = Gallus gallus
SEQUENCE: 242
GSVAEDISIN R                                                         11
```

```
SEQ ID NO: 243        moltype = AA   length = 9
FEATURE               Location/Qualifiers
source                1..9
                      mol_type = protein
                      organism = Gallus gallus
SEQUENCE: 243
HLFLPSSYK                                                             9
```

```
SEQ ID NO: 244        moltype = AA   length = 11
FEATURE               Location/Qualifiers
source                1..11
                      mol_type = protein
                      organism = Gallus gallus
SEQUENCE: 244
LAPTETEENI K                                                         11
```

```
SEQ ID NO: 245            moltype = AA  length = 8
FEATURE                   Location/Qualifiers
source                    1..8
                          mol_type = protein
                          organism = Gallus gallus
SEQUENCE: 245
LFLPSSYK                                                                8

SEQ ID NO: 246            moltype = AA  length = 12
FEATURE                   Location/Qualifiers
source                    1..12
                          mol_type = protein
                          organism = Gallus gallus
SEQUENCE: 246
LLAPTETEEN IK                                                          12

SEQ ID NO: 247            moltype = AA  length = 15
FEATURE                   Location/Qualifiers
source                    1..15
                          mol_type = protein
                          organism = Gallus gallus
SEQUENCE: 247
LYPEKDEPLN VLNLK                                                       15

SEQ ID NO: 248            moltype = AA  length = 18
FEATURE                   Location/Qualifiers
source                    1..18
                          mol_type = protein
                          organism = Gallus gallus
SEQUENCE: 248
RGIISALLAP TETEENIK                                                    18

SEQ ID NO: 249            moltype = AA  length = 10
FEATURE                   Location/Qualifiers
source                    1..10
                          mol_type = protein
                          organism = Gallus gallus
SEQUENCE: 249
SVAEDISINR                                                             10

SEQ ID NO: 250            moltype = DNA  length = 1041
FEATURE                   Location/Qualifiers
source                    1..1041
                          mol_type = other DNA
                          organism = Gallus gallus
SEQUENCE: 250
ctggatggct caaccagttt gacaagaaaa agaggactga agctggccac agcactgtct   60
ctgaataata acaaatttct aggaggaagt catgacaaca gtattagtct cacaaagaag  120
aacctggaag cttcaatgat aacaaatgca aaaatcaaca caccagtttt taaaatgaat  180
ttcagccaag agctttctgg aaatactaaa tctaaaccca ctatttcttc agggctaaaa  240
gtaacatatg actttactac tcctaagcat ggcatcagtg ctaagggagg agttgctcac  300
aaacttgctt tagagactct tacatcttac ctgtcagtag aaacatcaac aaaggggaat  360
atcgatggag caatttacac tggaaattca ttttctggag ctctagacca tgaagcaaac  420
acctatctgc atgctaatgg agttcggtca tctctcaagc ttgaggccaa ctccaaagta  480
gatggactct ggaacagtga aatgaaagaa atacttgcac ttgaagcatc taccagtcgt  540
gtttatgcag tctgggagca caatgggaaa aactttgcac gatacacacc tctcttcaca  600
acgacaggat ctcagaaatg caaagcaacc ttcgagctgg ctccttggac agtgtcagca  660
gatcttcaga ttcaggtcac tcagccaaat tccttcctgg acacagcatc agttaatcaa  720
gttgtcttaa tgaaagtcag tcctacagac cagaaagttg gctggaaggg tgaaggccaa  780
attcagtcat tatctctgag acatgacatg caattatcaa atgaaaaatc aaatgcaaag  840
tttgatattt ctggatcttt ggaagggtac atggacttcc tgaaaagaat taattgtgct  900
atttctaaga gagcttgtg ggatatcttg aagttggatg tcactactgt tgctgacaga   960
aagcactact taaatgcttc agcatccttc atatacagga agagtgatga tggttacttt 1020
ttccctatgc ctgtgattag g                                            1041

SEQ ID NO: 251            moltype = AA  length = 347
FEATURE                   Location/Qualifiers
source                    1..347
                          mol_type = protein
                          organism = Gallus gallus
SEQUENCE: 251
LDGSTSLTRK RGLKLATALS LNNNKFLGGS HDNSISLTKK NLEASMITNA KINTPVFKMN   60
FSQELSGNTK SKPTISSGLK VTYDFTTPKH GISAKGGVAH KLALETLTSY LSVETSTKGN  120
IDGAIYTGNS FSGALDHEAN TYLHANGVRS SLKLEANSKV DGLWNSEMKE ILAVEASTSR  180
VYAVWEHNGK NFARYTPLFT TTGSQKCKAT FELAPWTVSA DLQIQVTQPN SFLDTASVNQ  240
VVLMKVSPTD QKVGWKGEGQ IQSLSLRHDM QLSNEKSNAK FDISGSLEGY MDFLKRINCA  300
ISKKSLWDIL KLDVTTVADR KHYLNASASF IYRKSDDGYF FPMPVIR              347

SEQ ID NO: 252            moltype = AA  length = 11
```

-continued

```
FEATURE                    Location/Qualifiers
source                     1..11
                           mol_type = protein
                           organism = Gallus gallus
SEQUENCE: 252
EILAVEASTS R                                                              11

SEQ ID NO: 253             moltype = AA  length = 14
FEATURE                    Location/Qualifiers
source                     1..14
                           mol_type = protein
                           organism = Gallus gallus
SEQUENCE: 253
FLGGSHDNSI SLTK                                                          14

SEQ ID NO: 254             moltype = AA  length = 11
FEATURE                    Location/Qualifiers
source                     1..11
                           mol_type = protein
                           organism = Gallus gallus
SEQUENCE: 254
GEGQIQSLSL R                                                             11

SEQ ID NO: 255             moltype = AA  length = 7
FEATURE                    Location/Qualifiers
source                     1..7
                           mol_type = protein
                           organism = Gallus gallus
SEQUENCE: 255
INTPVFK                                                                   7

SEQ ID NO: 256             moltype = AA  length = 17
FEATURE                    Location/Qualifiers
source                     1..17
                           mol_type = protein
                           organism = Gallus gallus
SEQUENCE: 256
LALETLTSYL SVETSTK                                                       17

SEQ ID NO: 257             moltype = AA  length = 11
FEATURE                    Location/Qualifiers
source                     1..11
                           mol_type = protein
                           organism = Gallus gallus
SEQUENCE: 257
LATALSLNNN K                                                             11

SEQ ID NO: 258             moltype = AA  length = 9
FEATURE                    Location/Qualifiers
source                     1..9
                           mol_type = protein
                           organism = Gallus gallus
SEQUENCE: 258
LDGSTSLTR                                                                 9

SEQ ID NO: 259             moltype = AA  length = 8
FEATURE                    Location/Qualifiers
source                     1..8
                           mol_type = protein
                           organism = Gallus gallus
SEQUENCE: 259
PTISSGLK                                                                  8

SEQ ID NO: 260             moltype = AA  length = 12
FEATURE                    Location/Qualifiers
source                     1..12
                           mol_type = protein
                           organism = Gallus gallus
SEQUENCE: 260
YTPLFTTTGS QK                                                            12

SEQ ID NO: 261             moltype = DNA  length = 741
FEATURE                    Location/Qualifiers
source                     1..741
                           mol_type = other DNA
                           organism = Gallus gallus
SEQUENCE: 261
accccagtgt tagctgcttt tctccatggc attagtaaca ataagaagac aggaggcctc   60
cagcttgtgg tatatgctga taccgactcg gtcaggccgc gggtgcaggt atttgtgaca  120
```

```
aacctcacag attcgagcaa gtggaagctc tgcgcagatg cttcggtccg caatgctcac   180
aaggcagtgg cctacgtgaa atggggctgg gactgccggg actacaaggt ttctactgag   240
ctggtaactg ggcggtttgc tgggcaccct gctgcacaag tgaagctgga gtggcccaag   300
gttccttcga atgtcagatc agtggttgaa tggtttacg agtttgtccc tggggctgca     360
tttatgctgg gtttctctga gagaatggac aagaatcctt ctcgacaagc caggatggtt   420
gtggctctaa cttctccgag gacatgtgat gttgttgtca agctgcctga tataatcctc   480
tatcaaaaag ccgtgaggct tcctctatca ctccctgtgg gtccaaggat cccagcttca   540
gagctgcagc ctccaatctg gaacgtctt gctgaagccc cctctgccgt gctcgagaat    600
ttgaaagctc gctgctcagt ttcgtacaac aagatcaaaa cctttaatga agtcaagttc   660
aactactcga tgcccgcaaa ctgctatcac atcttggttc aggattgcag ctctgaactt   720
aagttcctgg tgatgatgaa a                                              741
```

```
SEQ ID NO: 262            moltype = AA  length = 247
FEATURE                   Location/Qualifiers
source                    1..247
                          mol_type = protein
                          organism = Gallus gallus
SEQUENCE: 262
TPVLAAFLHG ISNNKKTGGL QLVVYADTDS VRPRVQVFVT NLTDSSKWKL CADASVRNAH   60
KAVAYVKWGW DCRDYKVSTE LVTGRFAGHP AAQVKLEWPK VPSNVRSVVE WFYEFVPGAA   120
FMLGFSERMD KNPSRQARMV VALTSPRTCD VVVKLPDIIL YQKAVRLPLS LPVGPRIPAS   180
ELQPPIWNVF AEAPSAVLEN LKARCSVSYN KIKTFNEVKF NYSMPANCYH ILVQDCSSEL   240
KFLVMMK                                                              247
```

```
SEQ ID NO: 263            moltype = AA  length = 10
FEATURE                   Location/Qualifiers
source                    1..10
                          mol_type = protein
                          organism = Gallus gallus
SEQUENCE: 263
FAGHPAAQVK                                                           10
```

```
SEQ ID NO: 264            moltype = AA  length = 19
FEATURE                   Location/Qualifiers
source                    1..19
                          mol_type = protein
                          organism = Gallus gallus
SEQUENCE: 264
KTGGLQLVVY ADTDSVRPR                                                 19
```

```
SEQ ID NO: 265            moltype = AA  length = 10
FEATURE                   Location/Qualifiers
source                    1..10
                          mol_type = protein
                          organism = Gallus gallus
SEQUENCE: 265
LPLSLPVGPR                                                           10
```

```
SEQ ID NO: 266            moltype = AA  length = 9
FEATURE                   Location/Qualifiers
source                    1..9
                          mol_type = protein
                          organism = Gallus gallus
SEQUENCE: 266
TGGLQLVVY                                                            9
```

```
SEQ ID NO: 267            moltype = AA  length = 9
FEATURE                   Location/Qualifiers
source                    1..9
                          mol_type = protein
                          organism = Gallus gallus
SEQUENCE: 267
ADTDSVRPR                                                            9
```

```
SEQ ID NO: 268            moltype = AA  length = 15
FEATURE                   Location/Qualifiers
source                    1..15
                          mol_type = protein
                          organism = Gallus gallus
SEQUENCE: 268
TPVLAAFLHG ISNNK                                                     15
```

```
SEQ ID NO: 269            moltype = AA  length = 13
FEATURE                   Location/Qualifiers
source                    1..13
                          mol_type = protein
                          organism = Gallus gallus
SEQUENCE: 269
VQVFVTNLTD SSK                                                       13
```

-continued

```
SEQ ID NO: 270          moltype = AA  length = 9
FEATURE                 Location/Qualifiers
source                  1..9
                        mol_type = protein
                        organism = Gallus gallus
SEQUENCE: 270
VSTELVTGR                                                                9

SEQ ID NO: 271          moltype = AA  length = 8
FEATURE                 Location/Qualifiers
source                  1..8
                        mol_type = protein
                        organism = Gallus gallus
SEQUENCE: 271
VVALTSPR                                                                 8
```

The invention claimed is:

1. A method for detecting binding between an egg yolk antigen and an antibody present in a sample from a human subject that specifically binds to the egg yolk antigen, wherein the method comprises contacting an antibody in a sample with the egg yolk antigen provided in a kit, wherein the egg yolk antigen is defined in (1) or (2):

(1) (1A) a protein comprising a C-terminal portion of Vitellogenin-3, which is a protein comprising SEQ ID NO: 2; or (1B) a protein comprising at least one amino acid sequence selected from the group consisting of SEQ ID NOs: 2-11;

(2) (2A) a protein comprising a C-terminal portion of Vitellogenin-3, which is a protein comprising SEQ ID NO: 13; or (2B) a protein comprising at least one amino acid sequence selected from the group consisting of SEQ ID NOs: 9-11, 13, 14, and 16;

wherein the egg yolk antigen specifically binds to IgE antibody from a patient having allergy to egg yolk, and wherein the egg yolk antigen is immobilized to a carrier or a surface.

2. A method for diagnosing an allergy to an egg yolk antigen in a subject, wherein the egg yolk antigen is:

(1) (1A) a protein comprising a C-terminal portion of Vitellogenin-3, which is a protein comprising SEQ ID NO: 2;

(1B) a protein comprising at least one amino acid sequence selected from the group consisting of SEQ ID NOs: 2-11;

(2) (2A) a protein comprising a C-terminal portion of Vitellogenin-3, which is a protein comprising SEQ ID NO: 13; or (2B) a protein comprising at least one amino acid sequence selected from the group consisting of SEQ ID NOs: 9-11, 13, 14, and 16;

and wherein the method comprises detecting binding between said egg yolk antigen and an antibody present in a sample obtained from the subject by the method according to claim 1.

3. A method for detecting binding between an egg yolk antigen and an antibody present in a sample that specifically binds to the egg yolk antigen, wherein the method comprises contacting an antibody in a sample with the egg yolk antigen provided in a kit, wherein the egg yolk antigen is:

(1) (1A) a protein comprising a C-terminal portion of Vitellogenin-3, which is:

a protein comprising SEQ ID NO: 2; or (1B) a protein comprising at least one amino acid sequence selected from the group consisting of SEQ ID NOs: 2-11;

(2) (2A) a protein comprising a C-terminal portion of Vitellogenin-3, which is:

a protein comprising SEQ ID NO: 13; or (2B) a protein comprising at least one amino acid sequence selected from the group consisting of SEQ ID NOs: 9-11, 13, 14, and 16;

wherein the egg yolk antigen specifically binds to IgE antibody from a patient having allergy to egg yolk, and wherein the kit further comprises a reagent that detects binding between said egg yolk antigen and said antibody.

4. The method of claim 3, wherein the reagent comprises an enzymatically labelled secondary antibody against said antibody that specifically binds to said egg yolk antigen.

5. The method of claim 4, wherein the kit further comprises an enzyme substrate for an enzyme in the enzymatically labelled secondary antibody.

6. The method of claim 3, wherein the reagent comprises a fluorescently labelled secondary antibody against the antibody that specifically binds to said egg yolk antigen.

7. A method for diagnosing an allergy to an egg yolk antigen in a subject, wherein the egg yolk antigen is:

(1) (1A) a protein comprising a C-terminal portion of Vitellogenin-3, which is a protein comprising SEQ ID NO: 2;

(1B) a protein comprising at least one amino acid sequence selected from the group consisting of SEQ ID NOs: 2-11;

(2) (2A) a protein comprising a C-terminal portion of Vitellogenin-3, which is a protein comprising SEQ ID NO: 13; or (2B) a protein comprising at least one amino acid sequence selected from the group consisting of SEQ ID NOs: 9-11, 13, 14, and 16;

and wherein the method comprises detecting binding between said egg yolk antigen and an antibody present in a sample obtained from the subject by the method according to claim 3.

* * * * *